US010207250B2

(12) United States Patent
Ikeuchi et al.

(10) Patent No.: US 10,207,250 B2
(45) Date of Patent: Feb. 19, 2019

(54) POLY(METH)ACRYLIC ACID (SALT)-BASED PARTICULATE ABSORBENT

(71) Applicant: NIPPON SHOKUBAI CO., LTD., Osaka-shi, Osaka (JP)

(72) Inventors: Yoshitaka Ikeuchi, Himeji (JP); Yoshifumi Adachi, Himeji (JP)

(73) Assignee: NIPPON SHOKUBAI CO., LTD., Osaka-Shi, Osaka (JP)

( * ) Notice: Subject to any disclaimer, the term of this patent is extended or adjusted under 35 U.S.C. 154(b) by 0 days.

(21) Appl. No.: 15/122,095

(22) PCT Filed: Mar. 2, 2015

(86) PCT No.: PCT/JP2015/056110
§ 371 (c)(1),
(2) Date: Aug. 26, 2016

(87) PCT Pub. No.: WO2015/129917
PCT Pub. Date: Sep. 3, 2015

(65) Prior Publication Data
US 2017/0014801 A1 Jan. 19, 2017

(30) Foreign Application Priority Data

Feb. 28, 2014 (JP) .................. 2014-039599

(51) Int. Cl.
*B01J 20/26* (2006.01)
*B01J 20/28* (2006.01)
*A61L 15/18* (2006.01)
*A61L 15/24* (2006.01)
*A61L 15/42* (2006.01)
*A61L 15/60* (2006.01)
*B01J 20/30* (2006.01)

(52) U.S. Cl.
CPC ............ *B01J 20/261* (2013.01); *A61L 15/18* (2013.01); *A61L 15/24* (2013.01); *A61L 15/425* (2013.01); *A61L 15/60* (2013.01); *B01J 20/267* (2013.01); *B01J 20/28004* (2013.01); *B01J 20/28011* (2013.01); *B01J 20/28016* (2013.01); *B01J 20/28026* (2013.01); *B01J 20/28045* (2013.01); *B01J 20/3028* (2013.01); *B01J 20/3085* (2013.01); *B01J 2220/68* (2013.01)

(58) Field of Classification Search
CPC ........... B01J 20/26; B01J 20/261; A61L 15/18
USPC ....................................................... 502/402
See application file for complete search history.

(56) References Cited

U.S. PATENT DOCUMENTS

| 4,703,067 | A | 10/1987 | Mikita et al. |
|---|---|---|---|
| 5,002,986 | A | 3/1991 | Fujiura et al. |
| 5,124,188 | A | 6/1992 | Roe et al. |
| 5,154,713 | A | 10/1992 | Lind |
| 5,180,798 | A | 1/1993 | Nakamura et al. |
| 5,314,420 | A | 5/1994 | Smith et al. |
| 5,451,613 | A | 9/1995 | Smith et al. |
| 5,462,972 | A | 10/1995 | Smith et al. |
| 5,601,542 | A | 2/1997 | Melius et al. |
| 5,712,316 | A | 1/1998 | Dahmen et al. |
| 5,797,893 | A | 8/1998 | Wada et al. |
| 5,830,543 | A | 11/1998 | Miyake et al. |
| 5,856,370 | A | 1/1999 | Chmelir |
| 5,985,944 | A | 11/1999 | Ishizaki et al. |
| 6,071,976 | A | 6/2000 | Dairoku et al. |
| 6,107,358 | A | 8/2000 | Harada et al. |
| 6,133,193 | A | 10/2000 | Kajikawa et al. |
| 6,136,873 | A | 10/2000 | Hähnle et al. |
| 6,297,335 | B1 | 10/2001 | Funk et al. |
| 6,750,262 | B1 | 6/2004 | Hähnle et al. |
| 6,939,914 | B2 | 9/2005 | Qin et al. |
| 7,108,916 | B2 | 9/2006 | Ehrnsperger et al. |
| 7,153,910 | B2 | 12/2006 | Dairoku et al. |
| 7,473,470 | B2 | 1/2009 | Ishizaki et al. |
| 2004/0077796 | A1 | 4/2004 | Daniel et al. |
| 2006/0204755 | A1 | 9/2006 | Torii et al. |
| 2007/0015860 | A1 | 1/2007 | Frank |
| 2007/0225422 | A1 | 9/2007 | Sakamoto et al. |
| 2009/0298685 | A1 | 12/2009 | Torii et al. |
| 2010/0268181 | A1 | 10/2010 | Ziemer et al. |
| 2011/0313113 | A1 | 12/2011 | Sakamoto et al. |

(Continued)

FOREIGN PATENT DOCUMENTS

| EP | 1592750 A | 8/2004 |
|---|---|---|
| EP | 1521601 A | 5/2008 |

(Continued)

OTHER PUBLICATIONS

Official Notice of Reasons for Refusal dated May 30, 2017 which issued in the corresponding Japanese Patent Application No. 2016-505362, including English translation.

(Continued)

*Primary Examiner* — Edward M Johnson
(74) *Attorney, Agent, or Firm* — Dickinson Wright PLLC

(57) ABSTRACT

A low cost, a disposable diaper is provided that presents no difficulties in disposable diaper manufacture in humid climates, and that has a minimal amount of flowback, and rapid absorption time. A particulate water-absorbing agent is provided having as the principal component a poly (meth) acrylic acid (salt)-based water absorbing resin, wherein the water-absorbing agent has a particle size distribution of a weight average particle diameter of 300 to 500 μm, a blocking ratio after moisture absorption when left for one hour at 25° C. and 90% relative humidity of 20% or less, a surface tension of 60 mN/m or more, and a gel capillary absorption (GCA) of 28.0 g/g or more.

15 Claims, 10 Drawing Sheets

(56) References Cited

U.S. PATENT DOCUMENTS

| | | |
|---|---|---|
| 2012/0184670 A1 | 7/2012 | Kobayashi et al. |
| 2012/0258851 A1 | 10/2012 | Nakatsuru et al. |
| 2013/0026412 A1 | 1/2013 | Machida et al. |
| 2013/0101851 A1 | 4/2013 | Takaai et al. |
| 2013/0102750 A1 | 4/2013 | Watanabe et al. |
| 2013/0130017 A1 | 5/2013 | Takatori et al. |
| 2014/0042364 A1 | 2/2014 | Nogi et al. |
| 2014/0193641 A1 | 7/2014 | Torii et al. |

FOREIGN PATENT DOCUMENTS

| | | |
|---|---|---|
| JP | H1-318021 A | 12/1989 |
| JP | H15-82250 A | 3/2003 |
| JP | 3942660 B | 4/2007 |
| JP | 2008-142714 A | 6/2008 |
| WO | WO 91/15368 A1 | 10/1991 |
| WO | WO 92/18171 A1 | 10/1992 |
| WO | WO 94/022502 A1 | 10/1994 |
| WO | WO 95/02002 A1 | 1/1995 |
| WO | WO 96/017884 A1 | 6/1996 |
| WO | WO 97/017397 A1 | 5/1997 |
| WO | WO 2000/010619 A1 | 3/2000 |
| WO | WO 00/052087 A1 | 9/2000 |
| WO | WO 2002/060983 A1 | 8/2002 |
| WO | WO 2005/012406 A1 | 2/2005 |
| WO | WO 2005/063313 A1 | 7/2005 |
| WO | WO 2006/078046 A1 | 7/2006 |
| WO | WO 2007/116777 A1 | 10/2007 |
| WO | WO 2009/062902 | 5/2009 |
| WO | WO 2010/095427 A1 | 8/2010 |
| WO | WO 2011/040472 A1 | 4/2011 |
| WO | WO 2011/078298 A1 | 6/2011 |
| WO | WO 2011/126079 A1 | 10/2011 |
| WO | WO 2011/136301 A1 | 11/2011 |
| WO | WO 2012/002455 A1 | 1/2012 |
| WO | WO 2012/102406 A1 | 8/2012 |
| WO | WO 2013/002387 A1 | 1/2013 |
| WO | WO 2014/021388 A1 | 2/2014 |

OTHER PUBLICATIONS

Notification Concerning Transmittal of International Preliminary Report on Patentability and Written Opinion dated Sep. 6, 2016, which issued in the counterpart PCT Application No. PCT/JP2015/056110, including English translation.

Modern Superabsorbent Polymer Technology(1998), edited by Fre3dric L. Bucholz and Ndrew T. Graham, Viley-VCH, 52 pages.

International Search Report dated Mar. 31, 2015 in PCT Application No. PCT/JP2015/056110.

European Search Report dated Oct. 2, 2017 which issued in the corresponding Patent Application No. 15756085.5.

Chinese Office Action issued in related CN Application No. 201580010989.7, dated Feb. 24, 2018, with English translation.

300-500μm          45μm OR LESS

POLY(METH)ACRYLIC ACID (SALT)-BASED PARTICULATE ABSORBENT

TECHNICAL FIELD

The present invention relates to a particulate water-absorbing agent containing a poly (meth)acrylic acid (salt)-based water-absorbing resin as a main component. More specifically, the present invention relates to a particulate water-absorbing agent having an excellent handleability in a process of producing disposable diapers or the like and a capability of improving the performance of an absorbent article such as a disposable diaper.

BACKGROUND ART

A water-absorbing resin (SAP/Super Absorbent Polymer), which is a water-swellable and water-insoluble polymeric gelling agent, exhibits an excellent characteristic for absorbing body fluids. For this reason, a water-absorbing agent containing a water-absorbing resin as a main component is often used for absorbent articles such as a disposable diaper or a sanitary napkin, an agricultural water-retaining agent, an industrial water sealant, or the like. Many kinds of monomers and hydrophilic polymers have been proposed as a raw material of such a water-absorbing resin contained in an absorbent agent. However, a poly (meth)acrylic acid (salt)-based water-absorbing resin using (meth)acrylic acid and/or a salt thereof as a main component is often used in industry from the viewpoint of price and performance.

Such a water-absorbing resin is produced through a polymerization step, a drying step, an optional step of removing a non-dried product, a crushing step, a classification step, a surface crosslinking step and the like (Non-Patent Literature 1).

For disposable diapers, which are a primary application for a water-absorbing agent, remedies for urine leakage and skin rash are in need. As a method for examining these problems, a method for measuring a re-wet amount from a disposable diaper under pressure and a method for measuring liquid absorption time of a disposable diaper under pressure have been proposed.

It is estimated that, when urine is hardly incorporated into a disposable diaper while the body weight of a wearer of a disposable diaper is applied, or when a water-absorbing agent absorbs urine slowly even if urine is incorporated into the disposable diaper, urine leakage or skin rash occurs. Then, it is considered that improvement in absorbability of a water-absorbing agent under pressure and improvement in water absorbent speed of the water-absorbing agent lead to reduction in the re-wet amount of a disposable diaper and the liquid absorption time, and further lead to reduction in urine leakage and skin rash.

Conventionally, in order to reduce the re-wet amount of a disposable diaper and to reduce the liquid absorption time of the disposable diaper, many techniques for improving absorption characteristics under pressure have been proposed.

Specific examples of the proposition include a technique for using a water-absorbing agent having a large sum of absorption capacities under four different kinds of loads (PAI) for a disposable diaper (Patent Literature 1), a technique for improving diffusivity of a liquid not only in a vertical direction but also a horizontal direction in a SAP layer under pressure (Patent Literatures 2 and 3), a technique for improving fluid retention capacity under pressure while the SAP amount per unit area is large (Patent Literatures 4 and 5), and a technique for improving fluid retention capacity under pressure measured while there is a difference in height between a glass filter in contact with a water-absorbing agent and a liquid surface on the liquid supply side (Patent Literature 6).

Each technique of these Patent Literatures 1 to 6 has a long measurement time, and evaluates the fluid retention capacity under pressure in a saturation state. Improvement of these problems makes it possible to reduce the re-wet amount of a disposable diaper to some degree and to shorten the liquid absorption speed. However, the effect is still insufficient, and a new evaluation parameter has been demanded.

In order to improve the time required for a water-absorbing agent to absorb urine (absorbing time), many techniques to improve the particle shape have been proposed so far.

Specifically, a technique for improving a water absorbent speed by improving a specific surface area is known. Examples thereof include a technique for controlling the particle diameter finely (Patent Literature 7), a technique for performing surface crosslinking after controlling a particle diameter finely and finally performing granulation with a small amount of water (Patent Literature 8), a technique for crushing a polymerization gel with a specific energy to form particles having a granulated form (Patent Literatures 9 and 10), a technique for granulating water-absorbing resin fine particles having a large surface area using a binder (Patent Literatures 11 to 16), a technique for mixing water-absorbing resin fine particles having a large surface area with water or hot water at a high speed for granulation (Patent Literatures 17 and 18), a technique for performing polymerization in multiple steps to obtain granulated spherical particles when producing a water-absorbing resin by a reverse phase suspension polymerization method (Patent Literatures 19 and 20), a technique for lyophilizing a hydrogel to make the hydrogel porous (Patent Literature 21), a technique for performing foaming polymerization using a carbonate (Patent Literatures 22 to 29), a technique for foaming using an organic solvent (Patent Literatures 30 and 31), a technique for foaming by introducing an inert gas into an aqueous monomer solution (Patent Literatures 32 to 36), a technique of polymerization while a gas generated by raising the temperature of an aqueous monomer solution in the presence of a surfactant is dispersed in the aqueous monomer solution (Patent Literatures 37 and 38), a technique for using an azo compound (Patent Literatures 39, 40, and 41), a technique for using insoluble inorganic powder or water-insoluble particles (Patent Literatures 42 and 43), and a technique for polymerizing a slurry without stirring, in which a fine precipitate of sodium (meth)acrylate salt containing microbubbles of an inert gas and having a concentration of 45 to 60% by weight is dispersed (Patent Literature 44). Further, examples thereof include a technique for foaming and crosslinking after polymerization (Patent Literature 45) and a technique for foaming by adjusting the wind velocity or the like during drying (Patent Literature 46).

When the particle diameter is simply reduced as in the Patent Literature 7, an effect for improving the water absorbent speed can be observed. However, deterioration of handleability due to the increase of fine powder, particularly deterioration of handleability under moisture absorption, is observed significantly. In recent years, with spread of disposable diapers, it has become essential to produce disposable diapers in a humid area, and such deterioration of handleability has been considered to be unacceptable. Further, in a water-absorbing agent having a small particle diameter, the following problems have been observed. That is, when an absorbent material is formed by laminating pulp and a water-absorbing agent, the amount of the water-absorbing agent falling off from the absorbent material is increased, the working environment is deteriorated, and the liquid absorption time of a disposable diaper becomes longer.

When the water absorbent speed is improved by a granulation method as in the techniques of the Patent Literatures 8 to 18, an effect for improving the water absorbent speed can be observed to some extent. However, many techniques are not highly effective, that is, the granulated particles have low strength, and the granulated particles easily return to the original fine powder in a dry or swollen state. Further, it has been similarly observed that handleability is deteriorated particularly under moisture absorption by the increase of the surface area of a water-absorbing agent due to granulation.

Moreover, as in the techniques of the Patent Literatures 19 and 20, when granulated particles are formed by a reverse phase suspension polymerization method, an effect for improving the performance of a disposable diaper is insufficient. For example, there are problems of a complicated process and a residual organic solvent, as well as the problem that the re-wet amount is increased due to reduction in a surface tension.

In the methods for improving the water absorbent speed by a foaming method described in the Patent Literatures 21 to 46, an improvement effect can be observed to some degree, but many techniques do not exhibit a sufficient effect at all, and make cost higher due to the use an expensive raw material or a special apparatus. Further, there is a problem that a surfactant used to disperse bubbles reduces the surface tension and increases the re-wet amount. Moreover, since a water-absorbing agent subjected to foaming increases the surface area and fine powder similarly to the case of granulation, it has been similarly observed that handleability is deteriorated particularly under moisture absorption.

According to the related art, as a technique for imparting fluidity under moisture absorption (technique for suppressing blocking after moisture absorption), many techniques have been already proposed. Specific examples thereof include a technique for adding water-insoluble inorganic fine particles (Patent Literatures 47 and 52), a technique for adding a polyvalent metal salt of an organic acid having seven or more carbon atoms in a molecule thereof (Patent Literature 48), a technique for associating a water-insoluble metal phosphate on the surface (Patent Literature 49), a technique for treating with a specific silicone surfactant (Patent Literature 50), and a technique for mixing clay into a water-absorbing resin (Patent Literature 51).

However, it has been known that, only by applying the techniques of the Patent Literatures 47 to 52 for imparting fluidity under moisture absorption to the techniques of the Patent Literatures 1 to 46, the re-wet amount is increased and a problem such as occurrence of urine leakage or skin rash increases, while handleability can be improved.

CITATION LIST

Patent Literatures

Patent Literature 1: U.S. Pat. No. 5,601,542
Patent Literature 2: U.S. Pat. No. 5,760,080
Patent Literature 3: U.S. Pat. No. 5,797,893
Patent Literature 4: U.S. Pat. No. 6,297,335
Patent Literature 5: WO 2011/040472 A
Patent Literature 6: U.S. Pat. No. 7,108,916
Patent Literature 7: WO 92/18171 A
Patent Literature 8: U.S. Pat. No. 7,473,470
Patent Literature 9: WO 2011/126079 A
Patent Literature 10: WO 2013/002387 A
Patent Literature 11: U.S. Pat. No. 6,133,193
Patent Literature 12: WO 2005/012406 A
Patent Literature 13: U.S. Pat. No. 5,002,986
Patent Literature 14: U.S. Pat. No. 5,124,188
Patent Literature 15: U.S. Pat. No. 416,457
Patent Literature 16: WO 2006/078046 A
Patent Literature 17: U.S. Pat. No. 6,071,976
Patent Literature 18: U.S. Pat. No. 7,153,910
Patent Literature 19: U.S. Pat. No. 5,180,798
Patent Literature 20: US 2013/0130017 A
Patent Literature 21: U.S. Pat. No. 6,939,914
Patent Literature 22: WO 91/15368 A
Patent Literature 23: U.S. Pat. No. 5,154,713
Patent Literature 24: U.S. Pat. No. 5,314,420
Patent Literature 25: U.S. Pat. No. 5,399,591
Patent Literature 26: U.S. Pat. No. 5,451,613
Patent Literature 27: U.S. Pat. No. 5,462,972
Patent Literature 28: WO 95/02002 A
Patent Literature 29: WO 2005/063313 A
Patent Literature 30: WO 94/022502 A
Patent Literature 31: U.S. Pat. No. 4,703,067
Patent Literature 32: WO 97/017397 A
Patent Literature 33: WO 00/052087 A
Patent Literature 34: U.S. Pat. No. 6,107,358
Patent Literature 35: WO 2012/002455 A
Patent Literature 36: WO 2010/095427 A
Patent Literature 37: WO 2011/078298 A
Patent Literature 38: JP 3942660 B1
Patent Literature 39: U.S. Pat. No. 5,856,370
Patent Literature 40: U.S. Pat. No. 5,985,944
Patent Literature 41: WO 96/017884 A
Patent Literature 42: WO 2009/062902 A
Patent Literature 43: US 2007/0225422 A
Patent Literature 44: JP 1-318021 A
Patent Literature 45: EP 1521601 B
Patent Literature 46: WO 2011/136301 A
Patent Literature 47: WO 2007/116777 A
Patent Literature 48: EP 1592750 A
Patent Literature 49: WO 2002/060983 A
Patent Literature 50: JP 15-82250 A
Patent Literature 51: WO 2000/010619 A
Patent Literature 52: WO 2013/002387 A Non-Patent Literature Non-Patent Literature 1: Modern Superabsorbent Polymer Technology (1998)

SUMMARY OF INVENTION

Technical Problem

It is to provide a disposable diaper having no trouble when produced in a humid area, a small return amount, and a short liquid absorption time at low cost.

Solution to Problem

In order to solve the above problem, the present inventors made intensive studies. As a result, the present inventors considered that the reason why the evaluation methods represented by the Patent Literatures 1 to 6 were not necessarily correlated with the re-wet amount of a disposable diaper is that the measurement time is as long as 30 minutes to 1 hour (or several hours) and the evaluation is performed with the fluid retention capacity almost saturated. Then, the present inventors made consideration again by focusing on the pattern of discharging urine in a disposable diaper. That is, human urine is discharged in a unit of several tens ml at an interval of several hours. A disposable diaper is required to absorb discharged urine several times. Therefore, the present inventors considered that, if a water-absorbing agent absorbs the liquid quickly at every micturition and can have such a strong suction force capable of absorbing liquid in a pulp, the amount of urine remaining in the pulp becomes reduced, the time during which the skin is in contact with urine becomes shorter, and therefore rash hardly occurs and leakage can be reduced.

Then, as described in detail in Examples and FIG. 11, the ability of a water-absorbing agent to absorb liquid in a short time (10 minutes) while there was a difference in height by 10 cm between the liquid surface of 0.90% by weight of aqueous sodium chloride solution and a glass filter was evaluated as gel capillary absorption (GCA). The present inventors thereby found that, by controlling the GCA to a specific value or more, the liquid absorption speed of a disposable diaper can be maintained and the re-wet amount of the disposable diaper can be reduced to a level lower than that in the related art even when a treatment for imparting fluidity under moisture absorption is performed, and have completed the present invention.

That is, in order to solve the above problem, the particulate water-absorbing agent according to the present invention is characterized by containing a poly (meth)acrylic acid (salt)-based water-absorbing resin as a main component, having a particle size distribution of a weight average particle diameter of 300 to 500 µm, having a blocking ratio after moisture absorption when left for one hour at 25° C. and 90% relative humidity of 0 to 20%, having a surface tension of 60 mN/m or more, and having GCA of 28.0 g/g or more.

In order to solve the above problem, the first method for producing a particulate water-absorbing agent according to the present invention includes: (a1) a granulation step for granulating a poly (meth)acrylic acid (salt)-based water-absorbing resin having an average particle diameter of 10 to 180 µm to obtain granules; (b) a surface crosslinking step for surface crosslinking the granules; (c) a sizing step for making a proportion of particles having a particle diameter of 150 to 850 µm (specified by standard sieves) to be 95 to 100% by weight per 100% by weight of all the particles in the granules before and/or after the surface crosslinking step; and (d) a mixing step for mixing in water-insoluble inorganic fine particles, and the foregoing steps (a1) to (d) are performed sequentially, or at least one or more of the steps (a1) to (d) is performed simultaneously.

Furthermore, in order to solve the above problem, the second method for producing a particulate water-absorbing agent according to the present invention includes: (a2) an aqueous monomer solution preparation step for obtaining an aqueous sodium acrylate solution, in which bubbles have been dispersed previously prior to polymerization; (a3) a polymerization step for polymerizing the aqueous solution to obtain a foamed polymer of a poly (meth)acrylic acid (salt)-based water-absorbing resin; (b) a surface crosslinking step for surface crosslinking the foamed polymer; (c) a sizing step for making a proportion of particles having a particle diameter of 150 to 850 µm (specified by standard sieves) to be 95 to 100% by weight per 100% by weight of all the particles in the particles of the foamed polymer before and/or after the surface crosslinking step; and (d) a mixing step for mixing in water-insoluble inorganic fine particles, and the foregoing steps (a2) to (d) are performed sequentially, or the steps (c) and (d) are performed simultaneously.

Advantageous Effect of the Invention

According to the present invention, a disposable diaper having less trouble in its production process in a humid area where demand for disposable diapers is significantly increasing recently, and having improved performance compared to a conventional disposable diaper can be produced.

DESCRIPTION OF EMBODIMENTS

Figure 1:
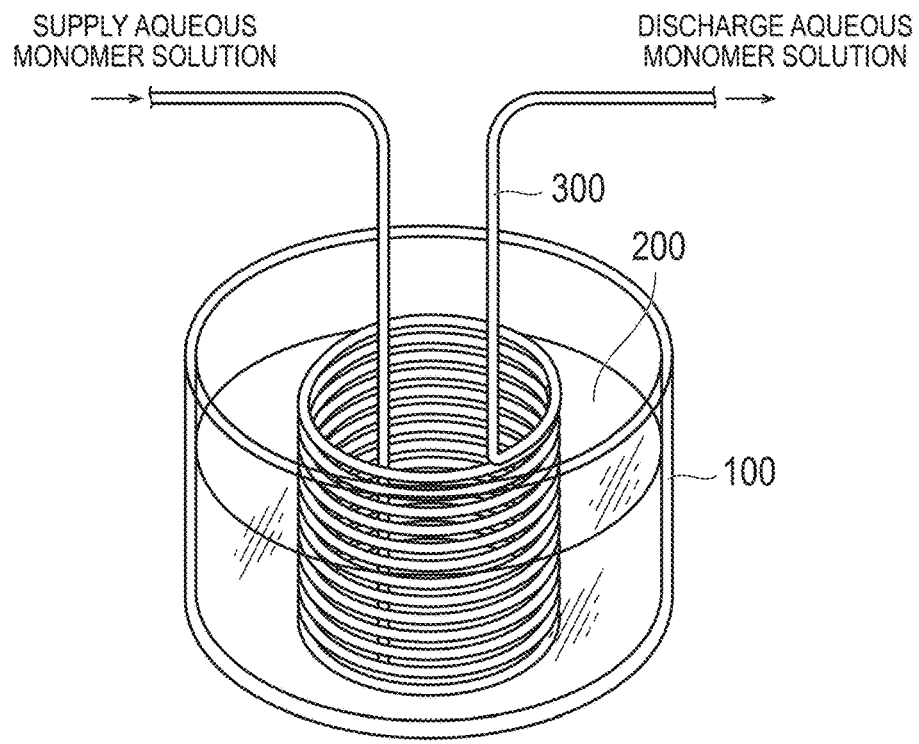
FIG. 1 is a perspective view illustrating an apparatus used for, as a method for incorporating bubbles, to which the method according to the present invention is applied, a continuous temperature-elevating method by heating an acrylic acid (salt)-based aqueous monomer solution.
Figure 2:
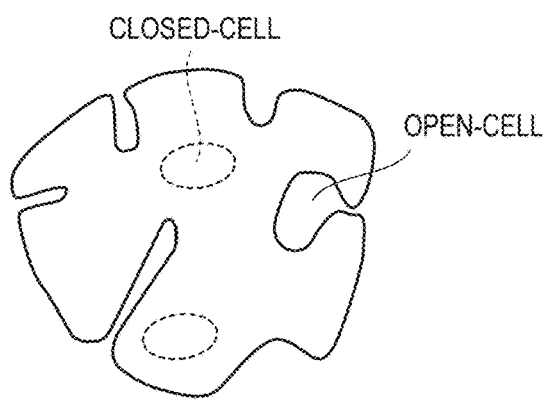
FIG. 2 is a cross sectional view schematically illustrating a closed cell and an open cell in a water-absorbing resin particle.
Figure 3:
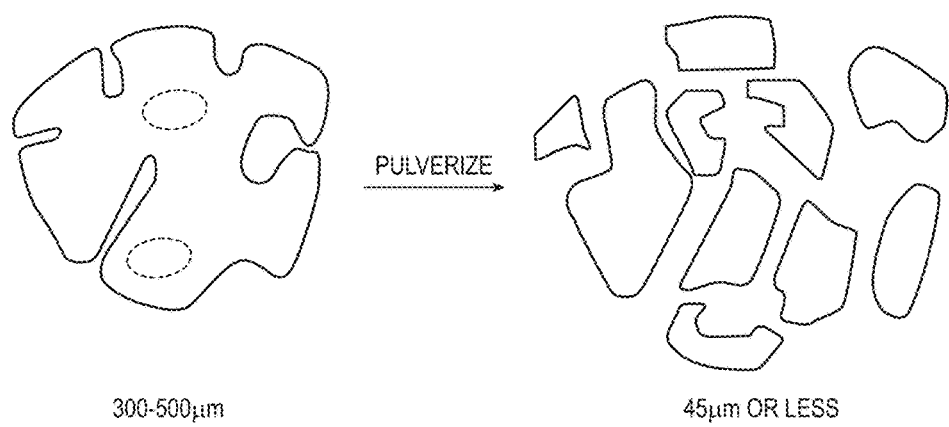
FIG. 3 is a cross sectional view schematically illustrating an operation of pulverizing water-absorbing resin particles (for example, in which the ratio of particles having a particle diameter of 850 to 150 µm is 95% by weight or more) to less than 45 µm for measuring an internal cell rate of the present invention. By pulverizing the water-absorbing resin particles to substantially break closed cells or make the closed cells open and then dry density measurement is performed with helium gas, the true density and the internal cell rate of the water-absorbing resin particles can be measured.

Hereinafter, the particulate water-absorbing agent according to the present invention and a method for producing the same will be described in detail. However, the scope of the present invention is not limited thereto, but can be modified appropriately to be performed within a range not impairing the gist of the present invention.

Specifically, the present invention is not limited to the following embodiments, but can be modified variously within the range indicated by claims. Embodiments obtained by appropriately combining technical means disclosed in different embodiments are also included in the technical scope of the present invention.

[1] Definition of Terms (1-1) Water-Absorbing Agent

In the present invention, the term "water-absorbing agent" is a gelling agent of an aqueous liquid containing a water-absorbing resin as a main component (preferably 60% by weight or more, more preferably 80% by weight or more, or 90% by weight or more relative to the total weight). As another optional component, the water-absorbing agent may contain water, inorganic fine particles, a moisture absorption blocking inhibitor, a cationic polymer compound, a water-soluble polyvalent metal cation-containing compound, a surfactant, a dust inhibitor, a coloring preventing agent, a urine resistance improver, a deodorant, a perfume, an anti-microbial agent, a foaming agent, a pigment, a dye, a fertilizer, an oxidizing agent, a reducing agent, and the like in an amount of 0 to 10% by weight, preferably 0.1 to 1% by weight for each.

(1-2) "Water-Absorbing Resin"

The water-absorbing resin in the present invention means a water-swellable and water-insoluble polymeric gelling agent. The term "water-swellable" means that fluid retention capacity without pressure (CRC) specified by ERT441.2-02 is 5 [g/g] or more, and "water-insoluble" means that Ext (soluble content) specified by ERT470.2-02 is from 0 to 50% by weight.

Further, the whole (100% by weight) of the water-absorbing resin is not necessarily a polymer. The water-absorbing resin may contain an additive or the like within a range maintaining the above-mentioned properties. In the present invention, a water-absorbing resin composition containing a small amount of an additive is also collectively referred to as a water-absorbing resin. The water-absorbing resin preferably has a powdery shape, and particularly preferably has a powdery shape having a particle size described below. In the meantime, in the present invention, the water-absorbing resin is also referred to as water-absorbing resin powder or water-absorbing resin particles.

(1-3) "Poly (Meth)Acrylic Acid (Salt)-Based Water-Absorbing Resin"

The term "poly (meth)acrylic acid (salt)-based water-absorbing resin" in the present invention means a polymer optionally containing a graft component and mainly containing a (meth)acrylic acid and/or a salt thereof (hereinafter, referred to as a (meth)acrylic acid (salt)) as a repeating unit.

Specifically, the poly (meth)acrylic acid (salt)-based water-absorbing resin means a water-absorbing resin containing a (meth)acrylic acid (salt) in an amount of 50 to 100% by mol, preferably 70 to 100% by mol, more preferably 90 to 100% by mol, and particularly preferably substantially 100% by mol per the total monomers used in polymerization (excluding a crosslinking agent). Further, in the present invention, a polymer having a poly (meth)acrylic acid salt type (neutralized) is also collectively referred to as a poly (meth)acrylic acid (salt)-based water-absorbing resin.

(1-4) "EDANA" and "ERT"

"EDANA" is an abbreviation for European Disposables and Nonwovens Associations. "ERT" is an abbreviation for EDANA Recommended Test Methods, which are methods of measuring a water-absorbing resin under the European standard (essentially the world standard). In the meantime, in the present invention, unless otherwise specified, physical properties of a water-absorbing agent (or a water-absorbing resin) are measured in conformity with the original document of ERT (publicly-known document: revised in 2002).

(a) "CRC" (ERT441.2-02)

"CRC" is an abbreviation of centrifuge retention capacity, and means fluid retention capacity without pressure (hereinafter, also referred to as "fluid retention capacity"). Specifically, "CRC" means fluid retention capacity (unit; [g/g]) obtained after 0.200 g of a water-absorbing agent (or a water-absorbing resin) in nonwoven fabric is freely swelled in 0.90% by weight of aqueous sodium chloride solution in a largely excessive amount for 30 minutes and then is further drained by a centrifuge.

(b) "AAP" (ERT442.2-02)

"AAP" is an abbreviation of absorption against pressure and means fluid retention capacity under pressure. Specifically, "AAP" means fluid retention capacity (unit; [g/g]) obtained after 0.900 g of a water-absorbing agent (or a water-absorbing resin) is swelled in 0.90% by weight of aqueous sodium chloride solution under load of 2.06 kPa (0.3 psi) for one hour. Absorption against pressure is expressed as Absorption Under Pressure in ERT442.2-02, but these are substantially the same.

(c) "PSD" (ERT420.2-02)

"PSD" is an abbreviation of Particle Size Distribution, and means a particle size distribution measured by sieve classification. In the meantime, the weight average particle diameter (D50) and a particle diameter distribution width are measured by the same method as "(1) Average Particle Diameter and Distribution of Particle Diameter" described in US Patent Publication No. 2006/0204755.

(d) "Ext" (ERT470.2-02)

"Ext" is an abbreviation of Extractables, and means a soluble content (amount of water-soluble component). Specifically, "Ext" is the amount of dissolved polymer (unit; % by weight) after 1.000 g of a water-absorbing agent (or a water-absorbing resin) is added to 200 ml of 0.90% by weight of aqueous sodium chloride solution and the resulting mixture is stirred for 16 hours. The amount of dissolved polymer is measured by pH titration.

(1-5) Others

As used herein, the phrase "X to Y" indicating a range means "X or more and Y or less". Further, "t (ton)" as a unit of weight means "metric ton". Moreover, unless otherwise specified, "ppm" means "weight ppm". Further, "Weight" and "mass", "% by weight" and "% by mass", and "part by weight" and "part by mass" are assumed to be synonyms, respectively. "-acid (salt)" means "-acid and/or a salt thereof" and "(meth)acrylic" means "acrylic and/or methacrylic". Furthermore, unless otherwise specified, physical properties and the like are measured at room temperature (20 to 25° C.) at a relative humidity of 40 to 50% RH.

[2] Method for Producing Particulate Water-Absorbing Agent

As described above, the first method for producing a particulate water-absorbing agent according to the present invention (production method 1) includes: (a1) a granulation step for granulating a poly (meth)acrylic acid (salt)-based water-absorbing resin having an average particle diameter of 10 to 180 μm to obtain granules; (b) a surface crosslinking step for surface crosslinking the granules; (c) a sizing step for making a proportion of particles having a particle diameter of 150 to 850 μm (specified by standard sieves) to be 95 to 100% by weight per 100% by weight of all the particles in the granules before and/or after the surface crosslinking step; and (d) a mixing step for mixing in water-insoluble inorganic fine particles, and the foregoing steps (a1) to (d) are performed sequentially, or at least one or more of the steps (a1) to (d) is performed simultaneously.

Further, as described above in a similar manner, the second method for producing a particulate water-absorbing agent according to the present invention (production method 2) includes: (a2) an aqueous monomer solution preparation step for obtaining an aqueous sodium acrylate solution, in which bubbles have been dispersed previously prior to polymerization; (a3) a polymerization step for polymerizing the aqueous solution to obtain a foamed polymer of a poly (meth)acrylic acid (salt)-based water-absorbing resin; (b) a surface crosslinking step for surface crosslinking the foamed polymer; (c) a sizing step for making a proportion of particles having a particle diameter of 150 to 850 μm (specified by standard sieves) to be 95 to 100% by weight per 100% by weight of all the particles in the particles of the foamed polymer before and/or after the surface crosslinking step; and (d) a mixing step for mixing in water-insoluble inorganic fine particles, and the foregoing steps (a2) to (d) are performed sequentially, or the steps (c) and (d) are performed simultaneously.

In the meantime, in the production methods 1 and 2 mentioned above, the term "sequentially" means that the steps (a1) to (d) (production method 1) and the steps (a2) to (d) (production method 2) are performed in this order. That is, for example, in the production method 1, it is meant that the step (b) is performed after termination of the step (a1), the step (c) is performed after termination of the step (b), and the step (d) is performed after termination of the step (c). In the meantime, a step other than the steps (a1) to (d) (production method 1) or the steps (a2) to (d) (production method 2) may be sandwiched therebetween.

Further, in the production method 1 mentioned above, the phrase "simultaneously performing at least apart" means to simultaneously perform, for example, the steps (a1) and (b), the steps (b) and (c), the steps (c) and (d) or the like. Particularly, it is preferable that the steps (c) and (d), or the steps (b) and (d) are performed simultaneously.

The period of time between the above steps is appropriately determined so as to include transportation time or storage time, and is preferably zero second or more and two hours or less, and more preferably one second or more and one hour or less.

Hereinafter, the method for producing a particulate water-absorbing agent according to the present invention will be described mainly in a temporal order. However, each of the production methods 1 and 2 is only required to include the above-mentioned essential steps, and may further include another step within a range not departing from the gist of each of the production methods.

(2-1) Method for Introducing Foamed Structure into Water-Absorbing Resin Particles by Incorporating Bubbles Thereinto Before or During Polymerization Step of a (Meth) Acrylic Acid (Salt)-Based Aqueous Monomer Solution (2-1-1) Preparation Step of (Meth)Acrylic Acid (Salt)-Based Aqueous Monomer Solution As used herein, "(meth)acrylic acid (salt)-based aqueous monomer solution" is an aqueous monomer solution containing a (meth)acrylic acid (salt) as a main component, and optionally containing a component constituting a water-absorbing resin, such as a crosslinking agent, a graft component, or a minor component (chelating agent, surfactant, dispersant, or the like). In other words, "(meth)acrylic acid (salt)-based aqueous monomer solution" means a solution subjected to polymerization as it is after being added with a polymerization initiator.

The above-mentioned (meth)acrylic acid (salt) may be unneutralized or a salt type (fully neutralized or partially neutralized). Further, the aqueous monomer solution may have a concentration larger than a saturation concentration. Even a supersaturated aqueous solution of a (meth)acrylic acid (salt) or a slurry aqueous solution thereof (aqueous dispersion) is assumed to be the (meth)acrylic acid (salt)-based aqueous monomer solution of the present invention. In the meantime, from the viewpoint of physical properties of the resulting water-absorbing resin, it is preferable to use a (meth)acrylic acid (salt)-based aqueous monomer solution having a concentration equal to or lower than the saturation concentration.

Furthermore, as a solvent for dissolving a monomer, water is preferable. A (meth)acrylic acid (salt)-based monomer is handled as an aqueous solution. Here, "aqueous solution" is not limited to a case where 100% by weight of the solvent is water. A water-soluble organic solvent (for example, alcohol or the like) may be used together with water in an amount of 0 to 30% by weight, preferably 0 to 5% by weight per 100% by weight of the total amount of the solvent. In the present invention, these solutions are assumed to be aqueous solutions.

As used herein, "(meth)acrylic acid (salt)-based aqueous monomer solution during preparation" described below means an aqueous solution of the above-mentioned (meth) acrylic acid (salt) before all the components are mixed with the aqueous monomer solution containing the (meth)acrylic acid (salt) as a main component. Specifically, an aqueous (meth)acrylic acid solution or a fully neutralized or partially neutralized aqueous (meth)acrylic acid (salt) solution corresponds thereto.

By further neutralizing the (meth)acrylic acid (salt)-based aqueous monomer solution during preparation or mixing water as a solvent or the above minor component or the like to the (meth)acrylic acid (salt)-based aqueous monomer solution, a final (meth)acrylic acid (salt)-based aqueous monomer solution is obtained. This final (meth)acrylic acid (salt)-based aqueous monomer solution before being put into a polymerization apparatus or before the polymerization is initiated after being put into the polymerization apparatus is referred to as "(meth)acrylic acid (salt)-based aqueous monomer solution after preparation before a polymerization step".

(Monomer)

For the water-absorbing resin of the present invention, a monomer containing a (meth)acrylic acid (salt) as a main component is used. The "main component" means that a (meth)acrylic acid (salt) is contained in an amount of usually 50% by mol or more, preferably 70% by mol or more, more preferably 80% by mol or more, still more preferably 90% by mol or more, and particularly preferably 95% by mol or more (the upper limit is 100% by mol) per the total amount of monomers (excluding an internal crosslinking agent). In the meantime, in the present invention, the poly (meth) acrylic acid (salt) is not limited to an unneutralized poly (meth)acrylic acid (salt) (rate of neutralization is zero % by mol), but encompasses a partially neutralized or fully neutralized (rate of neutralization is 100% by mol) poly (meth) acrylic acid (salt).

As long as a (meth)acrylic acid (salt) is contained as a main component, a monomer to become a water-absorbing resin by polymerization may be contained in addition thereto. Example thereof include an anionic unsaturated monomer (salt) such as (anhydrous) maleic acid, itaconic acid, cinnamic acid, vinyl sulfonic acid, allyl toluenesulfonic acid, vinyl toluene sulfonic acid, styrene sulfonic acid, 2-(meth)acrylamide-2-methyl propanesulfonic acid, 2-(meth)acryloyl ethanesulfonic acid, 2-(meth)acryloyl propane sulfonic acid, 2-hydroxyethyl (meth)acryloyl phosphate and the like; a mercapto group-containing unsaturated monomer; a phenolic hydroxy group-containing unsaturated monomer; an amide group-containing unsaturated monomer such as (meth)acrylamide, N-ethyl (meth)acrylamide, or N,N-dimethyl (meth)acrylamide and the like; and an amino group-containing unsaturated monomer such as N,N-dimethyl aminoethyl (meth)acrylate, N,N-dimethyl aminopropyl (meth)acrylate, N,N-dimethylaminopropyl (meth)acrylamide and the like. Further, the water-absorbing resin may contain the above-mentioned other monomers as a copolymer component.

In the present invention, the rate of neutralization of a (meth)acrylic acid (salt)-based monomer or a hydrogel-forming crosslinked polymer after polymerization is not particularly limited, but is preferably from 40 to 90% by mol, more preferably from 50 to 80% by mol, and still more preferably from 60 to 75% by mol from the viewpoint of physical properties of the resulting water-absorbing resin particles or a reactivity of a surface crosslinking agent. In this regard, however, when the rate of neutralization is low, the water absorbent speed tends to be lowered (for example, the water absorption time by Vortex method is increased). On the contrary, when the rate of neutralization is high, the reactivity between the poly (meth)acrylic acid (salt)-based water-absorbing resin and the surface crosslinking agent (particularly, dehydration-reactive surface crosslinking agent described below) tends to be lowered, the productivity tends to be reduced, or the fluid retention capacity under pressure (for example, AAP) tends to be reduced. Therefore, the rate of neutralization is preferably within the above-mentioned range.

The neutralization may be conducted to a hydrogel after polymerization, as well as to the monomer and/or the aqueous monomer solution before polymerization, and both of these may be adopted together. When neutralization is performed multiple times, it is preferable that, by taking the addition amounts of all the basic compounds in consideration, the rate of neutralization is adjusted within the above-mentioned range.

Further, from the viewpoint of the fluid retention capacity without pressure (CRC) or the water absorbent speed of a water-absorbing resin obtained as a final product, a part or the whole of the (meth)acrylic acid (salt)-based monomer or a hydrogel-forming crosslinked polymer may be a salt type. A monovalent salt such as a sodium salt, a lithium salt, a potassium salt, an ammonium salt, or an amine is preferable. Among these salts, an alkali metal salt is more preferable, and a sodium salt and/or a potassium salt are still more preferable. A sodium salt is particularly preferable from the viewpoint of cost and physical properties.

(Polymerization Inhibitor)

The (meth)acrylic acid (salt)-based monomer of the present invention contains a polymerization inhibitor. The polymerization inhibitor is not particularly limited, but examples thereof include an N-oxyl compound, a manganese compound, and a substituted phenol compound disclosed in WO 2008/096713 A. Among these compounds, a substituted phenol is preferable and a methoxyphenol is particularly preferable.

Examples of the methoxyphenol include o, m, p-methoxyphenols and a methoxyphenol having one or more substituents such as a methyl group, a t-butyl group, or a hydroxy group. In the present invention, p-methoxyphenol is particularly preferable.

A methoxyphenol content in the (meth)acrylic acid (salt)-based monomer is preferably from 10 to 200 ppm by weight, more preferably from 5 to 160 ppm by weight, still more preferably from 10 to 160 ppm by weight, still more preferably from 10 to 100 ppm by weight, still more preferably from 10 to 80 ppm by weight, and most preferably from 10 to 70 ppm by weight. The methoxyphenol content of more than the above-mentioned range is not preferable since the color hue of the resulting water-absorbing resin may be deteriorated (coloration such as turning yellow). Further, the above-mentioned content of less than 5 ppm by weight is not preferable since, when p-methoxyphenol is removed by purification such as distillation, there is a higher risk to cause polymerization before intentionally starting polymerization.

(Internal Crosslinking Agent)

In the present invention, in the above-mentioned polymerization, an internal crosslinking agent is used, if necessary. As the internal crosslinking agent, a publicly-known internal crosslinking agent can be used. Examples thereof include N,N'-methylene bis(meth)acrylamide, (poly) ethylene glycol di(meth)acrylate, (poly) propylene glycol di(meth)acrylate, trimethylolpropane tri(meth)acrylate, glycerin tri(meth)acrylate, glycerin acrylate methacrylate, ethylene oxide modified trimethylolpropane tri(meth)acrylate, pentaerythritol hexa(meth)acrylate, triallyl cyanurate, triallyl isocyanurate, triallyl phosphate, triallylamine, poly (meth)allyloxy alkane, (poly) ethylene glycol diglycidyl ether, glycerol diglycidyl ether, ethylene glycol, polyethylene glycol, propylene glycol, glycerin, 1,4-butanediol, pentaerythritol, ethylenediamine, ethylene carbonate, propylene carbonate, polyethylene imine, glycidyl (meth)acrylate and the like. One or more kinds of these compounds can be used considering the reactivity. Among these, it is preferable to use a compound having two or more polymerizable unsaturated groups.

The amount of the internal crosslinking agent used can be determined appropriately depending on the desired properties of a water-absorbing resin, but is preferably from 0.001 to 5% by mol, more preferably from 0.005 to 2% by mol, and still more preferably from 0.01 to 1% by mol per 100% by mol of the (meth)acrylic acid (salt)-based monomer. The used amount of 0.001% by mol or more does not make a soluble content of the resulting water-absorbing resin too large, and can secure absorption amount under pressure sufficiently. On the other hand, the used amount of 5% by mol or less does not make a crosslinking density of the resulting water-absorbing resin too high, and can secure absorption amount sufficiently. In order to introduce a crosslinking structure into a polymer using the internal crosslinking agent, the internal crosslinking agent is only required to be added to a reaction system before, during, or after polymerization, or after neutralization of the monomer. The internal crosslinking agent may be added to a reaction system at once or in a divided manner.

(Surfactant and Dispersant)

In the production method 1 or 2 (particularly, in the production method 2) of the present invention, it is preferable to add a surfactant and/or a dispersant to a (meth)acrylic acid (salt)-based aqueous monomer solution during preparation or after preparation before a polymerization step such that generated bubbles are suspended stably. Further, by appropriately designing the kind, the addition amount and the like of the surfactant and/or the dispersant, a water-absorbing resin having desired properties can be obtained. The surfactant is preferably a non-polymer compound and the dispersant is preferably a polymer compound.

The addition amount of the surfactant and/or the dispersant is designed appropriately depending on the kind thereof, and specific numerical values thereof will be described below. The surfactant and/or the dispersant are added to a (meth)acrylic acid (salt)-based aqueous monomer solution such that the surface tension of the resulting water-absorbing resin is preferably 60 [mN/m] or more, and more preferably within the range described in "(3-5) Surface tension" below. The surface tension of less than 60 [mN/m] is not preferable since the re-wet amount tends to be increased when a disposable diaper is used. In the meantime, in order to prevent reduction in the surface tension, it is preferable to use a surfactant having a reactivity or a polymerizability with a water-absorbing resin or a (meth) acrylic acid (salt)-based monomer, for example, a surfactant having an unsaturated polymerizable group (particularly, α, β-unsaturated double bond) or a reactive group (a hydroxy group or an amino group). Further, the use of a hydrophilic surfactant (HLB: from 1 to 18, particularly from 8 to 15) having a high solubility in water is also preferable.

(Surfactant)

In the present invention, a surfactant which can be used is not particularly limited. However, examples thereof include surfactants disclosed in WO 97/017397 A and U.S. Pat. No. 6,107,358, that is, a nonionic surfactant, an anionic surfactant, a cationic surfactant, and an amphoteric surfactant. These surfactants may have a polymerizability or a reactivity with a (meth)acrylic acid (salt)-based monomer or a water-absorbing resin particle. That is, the surfactant is only required to have a polymerizable functional group such as a vinyl group, an allyl group, or an allyloxy group, or a reactive group such as a glycidyl group having a reactivity with a functional group of a water-absorbing resin.

Examples of the nonionic surfactant include a polyoxyalkylene alkyl ether such as polyoxyethylene lauryl ether, polyoxyethylene cetyl ether, polyoxyethylene stearyl ether, or polyoxyethylene oleyl ether; a polyoxyalkylene alkyl phenyl ether such as polyoxyethylene octyl phenyl ether or polyoxyethylene nonylphenyl ether; a polyoxyalkylene alkyl amino ether such as polyoxyethylene lauryl amino ether or polyoxyethylene stearyl amino ether; a sorbitan fatty acid ester such as sorbitan monolaurate, sorbitan monopalmitate, sorbitan monostearate, or sorbitan monooleate; a polyoxyalkylene sorbitan fatty acid ester such as polyoxyethylene sorbitan monolaurate, polyoxyethylene sorbitan monopalmitate, polyoxyethylene sorbitan monostearate, or polyoxyethylene sorbitan monooleate; a polyalkylene glycol fatty acid ester such as polyethylene glycol monolaurate, polyethylene glycol monooleate, polyethylene glycol monostearate, polyethylene glycol dilaurate, or polyethylene glycol distearate; and a glycerol fatty acid ester such as lauric acid monoglyceride, stearic acid monoglyceride, or oleic acid monoglyceride.

Examples of the anionic surfactant include a sulfate such as polyoxyethylene lauryl ether sodium sulfate, polyoxyethylene octyl phenyl ether sodium sulfate, polyoxyethylene nonylphenyl ether sodium sulfate, triethanolamine lauryl sulfate, sodium lauryl sulfate, potassium lauryl sulfate, or ammonium lauryl sulfate; a sulfonate such as sodium dodecyl benzene sulfonate, sodium alkyl naphthalene sulfonate, or sodium dialkyl sulfosuccinate; and a phosphate such as potassium alkyl phosphate.

Examples of the cationic surfactant include a quaternary ammonium salt such as lauryl trimethyl ammonium chloride, stearyl trimethyl ammonium chloride, cetyl trimethyl ammonium chloride, or stearyl trimethyl ammonium chloride.

Further, in addition to the above surfactants, examples thereof include a silicone surfactant. In addition to an anionic, nonionic, or cationic silicone surfactant, the silicone surfactant includes a polyoxyalkylene-modified silicone surfactant. Specific examples thereof include polyoxyethylene-modified dimethylpolysiloxane, polyoxyethylene-polyoxypropylene block or random copolymer-modified dimethyl polysiloxane, dimethyl polysiloxane modified with polyoxyethylene having an alkyl group having 1 to 12 carbon atoms at a terminal, dimethylpolysiloxane modified with a polyoxyethylene-polyoxypropylene block or random copolymer having 1 to 12 carbon atoms at a terminal, and a polyoxyalkylene-modified product of a dimethylpolysiloxane derivative having an amino group, an epoxy group, or the like at a terminal of dimethylpolysiloxane and/or in a molecule thereof. Among these compounds, polyoxyethylene-modified dimethyl polysiloxane, and polyoxyethylene-polyoxypropylene block or random copolymer-modified dimethyl polysiloxane are preferable. Polyoxyethylene-modified dimethyl polysiloxane is more preferable due to industrial availability at low cost.

Only one kind of the surfactant may be used, or two or more kinds thereof may be used together. The surfactant may be used together with a dispersant (particularly, a polymer dispersant) described below. Among these surfactants, from the viewpoint of an effect, an anionic surfactant, a nonionic surfactant, or a silicone surfactant is preferably used, and a nonionic surfactant or a silicone surfactant is more preferably used.

The addition amount of the surfactant is determined appropriately depending on the kind or target properties (particularly, the water absorbent speed or the surface tension), but is preferably more than 0 and 2 parts by weight or less, more preferably more than 0 and 0.03 parts by weight or less, still more preferably more than 0 and 0.015 parts by weight or less, particularly preferably more than 0 and 0.01 parts by weight or less, and most preferably more than 0 and 0.008 parts by weight or less per 100 parts by weight of the monomer used. The addition amount of the surfactant is similarly applied to that for the water-absorbing resin particle. Furthermore, if necessary, the addition amount of the surfactant can be applied to that for a water-absorbing agent obtained after being coated with a surfactant described in "(2-4) Step for adding additive" below. The addition amount within the above range is preferable because it is easy to control foaming during a polymerization reaction. Further, the addition amount within the above range is preferable because a risk of lowering the surface tension of a water-absorbing resin particle excessively can be reduced and the increase in the re-wet amount at the time when the water-absorbing agent is used for a disposable diaper or the like can be suppressed.

Addition of a very small amount of a surfactant improves transportability and damage resistance of the resulting water-absorbing resin particle, and improves properties of the water-absorbing resin particle after surface crosslinking or after powder transportation as a result. Therefore, the addition amount is preferably larger than 0 ppm by weight, particularly preferably 0.1 ppm by weight or more, more preferably 1 ppm by weight or more, still more preferably 5 ppm by weight or more, and still more preferably 10 ppm by weight or more.

(Dispersant)

A dispersant is a compound which stably disperses bubbles generated in a (meth)acrylic acid (salt)-based aqueous monomer solution during preparation or after preparation before a polymerization step. The dispersant used in the present invention is not particularly limited. A water-absorbing polymer dispersant or a water-absorbing and hydrophilic polymer dispersant is preferable, and a water-soluble polymer dispersant is more preferable. The weight average molecular weight thereof is determined appropriately depending on the kind of the dispersant, and is preferably from 500 to 10000000, more preferably from 5000 to 5000000, and particularly preferably from 10000 to 3000000.

The kind of the dispersant is not particularly limited. Examples thereof include a hydrophilic polymer such as starch, a starch derivative, cellulose, a cellulose derivative, polyvinyl alcohol (PVA), carboxymethylcellulose (sodium), hydroxyethylcellulose, poly (meth)acrylic acid (salt), or a poly (meth)acrylic acid (salt) crosslinked body. Among these compounds, a water-soluble polymer dispersant selected from starch, cellulose, and PVA is preferable from the viewpoint of an effect of the present invention.

The amount of the dispersant used is preferably more than 0 part by weight and 50 parts by weight or less, more preferably from 0.01 to 20 parts by weight, still more preferably from 0.05 to 10 parts by weight, and particularly preferably from 0.1 to 5 parts by weight per 100 parts by weight of the (meth)acrylic acid (salt)-based monomer.

The specified amount of the dispersant used is similarly applied to the resulting water-absorbing resin particles. The addition amount of the dispersant within the above range is preferable because it is easy to control foaming during a polymerization reaction. Further, it is also preferable because a risk of excessively lowering the fluid retention capacity or the like of the water-absorbing resin particles can be reduced and therefore the increase of the re-wet amount can be suppressed when the particles are used for a disposable diaper or the like.

(2-1-2) Step for Generating and Dispersing Bubbles (Particularly, (a2) Step for Obtaining Aqueous Sodium Acrylate Solution Having Bubbles Dispersed Therein in Advance of Polymerization (Monomer Preparation Step)) (Control of Cell Rate)

In the present invention, water-absorbing resin particles containing internal cells are preferably used for surface crosslinking. In a preferable method for controlling bubbles, polymerization is performed by incorporating a predetermined amount of bubbles during polymerization, and the internal cell rate of the resulting water-absorbing resin (specified in WO 2011/078298 A (Patent Literature 37)) is preferably 0.5% or more, more preferably from 1.0 to 8.0%, still more preferably from 2.8 to 6.6%, still more preferably from 3.0 to 6.5%, still more preferably from 3.5 to 6.5%, still more preferably from 3.8 to 6.5%, and most preferably from 4.0 to 6.5%.

The internal cell rate of equal to or more than the lower limit of the above range is preferable because a sufficient effect for improving the water absorbent speed can be obtained. On the other hand, the internal cell rate of equal to or more less than the upper limit of the above range is preferable because a risk of excessively lowering the bulk density of the water-absorbing resin particles can be reduced, and deterioration of properties such as damage resistance, GCA, fluid retention capacity under pressure (AAP) and the like can be prevented. In the production method of the present invention, said internal cell rate can be controlled appropriately based upon the bubble content during polymerization, the drying temperature (more expansion at a higher temperature), or the like.

As a method for incorporating bubbles, it is only required to incorporate bubbles into an aqueous monomer solution during polymerization. A solid foaming agent such as a carbonate or a water-soluble azo compound (for example, water-soluble azo polymerization initiator), a liquid foaming agent such as a hydrophobic or hydrophilic organic solvent, and a gas foaming agent such as various bubbles (dispersing a compound in a gas state at a normal temperature in a monomer) are used appropriately. It is preferable to disperse a gas in the monomer and it is more preferable to apply the method for producing a poly (meth)acrylic acid (salt)-based water-absorbing resin of Patent Literature 37 (WO 2011/078298 A). At this time, the volume of the aqueous monomer solution is expanded by the addition of a foaming agent or the introduction of a gas. The expansion rate thereof is preferably 5 times or less, more preferably 3 times or less, still more preferably 2 times or less, still more preferably 1.1 times or less, still more preferably 1.05 times or less, and still more preferably 1.02 times or less as an upper limit relative to the volume without addition of a foaming agent or introduction of a gas. The expansion rate is preferably more than 1 time and particularly preferably 1.01 times or more as a lower limit. A method for polymerization while a large amount of bubbles are dispersed was conventionally known. However, in the present invention, polymerization is performed while bubbles are not excessively dispersed, and therefore the reduction in the bulk specific gravity is small. In the meantime, the expansion rate can be easily measured by comparing the volumes of aqueous monomer solutions having the same temperature and the same weight by using a measuring cylinder, a measuring flask, or the like.

When the internal cell rate is controlled in the present invention, as an example of the controlling method, the method of Patent Literature 37 will be described below. The disclosed contents are incorporated by reference, and are included in the disclosed contents of the present application. The entire description in Patent Literature 37 can be used as the description and method of the present invention, but the present invention is not limited to the method.

Hereinafter, a preferable method for controlling the bubble content will be described.

(Preferable Method for Controlling the Bubble Content)

In the present invention, in order to increase GCA, increase the water absorbent speed, or improve the fluid retention capacity under pressure, cells are preferably introduced into a water-absorbing resin, and various kinds of foaming polymerizations or the like can be applied. As a preferable method, for example, the method described in Patent Literature 37 is used.

The production method of Patent Literature 37, which can be used for controlling the bubble content, includes a step for generating and incorporating bubbles by lowering the solubility of a dissolved gas in a (meth)acrylic acid (salt)-based aqueous monomer solution in the presence of a surfactant and/or a dispersant in a method for producing a poly (meth)acrylic acid (salt)-based water-absorbing resin, including a step for polymerizing the (meth)acrylic acid (salt)-based aqueous monomer solution containing bubbles, an optional step for refining gel of a hydrogel-forming crosslinked polymer during or after polymerization, and a step for drying a hydrogel-forming crosslinked polymer.

Here, the surfactant is only required to be added before the step for generating and incorporating bubbles. Therefore, the surfactant may be added after the polymerization step, but it is preferable to add the surfactant before the polymerization step.

The production method of the present invention preferably includes a step for generating and incorporating bubbles by lowering the solubility of a dissolved gas in a (meth)acrylic acid (salt)-based aqueous monomer solution containing a surfactant and/or a dispersant during or after preparation before a polymerization step. The step for generating and incorporating bubbles is only required to be performed before the polymerization step is completed, and therefore may be performed after the polymerization step is initiated, but is preferably performed before the polymerization step. Further, in order to dissolve a gas in an aqueous solution, a gas (for example, an inert gas) may be introduced into the aqueous solution in advance, or it is not necessary to do so. As a specific method for lowering the solubility of a dissolved gas, at least one of the following methods (a) and (b) is used. Examples thereof include a method performed by raising the temperature of a (meth)acrylic acid (salt)-based aqueous monomer solution and a method performed by mixing a water-soluble organic substance with a (meth)acrylic acid (salt)-based aqueous monomer solution.

Method (a): Method by Raising the Temperature of (Meth)Acrylic Acid (Salt)-Based Aqueous Monomer Solution Examples of a method for dispersing bubbles in a (meth)acrylic acid (salt)-based aqueous monomer solution include a method for raising the temperature of a (meth)acrylic acid (salt)-based aqueous monomer solution prepared by mixing a monomer and/or a salt thereof, and an internal crosslinking agent and water, if necessary, and a method for lowering the solubility of a gas in an aqueous solution by raising the temperature at a preparation stage of a (meth)acrylic acid (salt)-based aqueous monomer solution.

When raising the temperature of the (meth)acrylic acid (salt)-based aqueous monomer solution after preparation, a method for making the aqueous monomer solution pass through a heat exchanger formed of a pipe or a container, and a method of irradiation with an ultraviolet ray can be used. The temperature of the aqueous monomer solution the temperature of which has been raised is preferably high such that the solubility of a gas is lowered. Specifically, the temperature is preferably from 40° C. to the boiling point of the aqueous monomer solution, more preferably from 50 to 100° C., still more preferably from 60 to 98° C., and most preferably from 70 to 95° C. The temperature rising width is preferably +5° C. or more, more preferably from +10 to +100° C., still more preferably from +20 to +90° C., and particularly preferably from +30 to +80° C. from the viewpoint of a generation amount of bubbles.

When the temperature rising width is +5° C. or more, stability of bubbles before polymerization is secured. On the other hand, when the temperature rising width is +100° C. or less, the generation amount of bubbles before polymerization is secured sufficiently, and therefore the water absorbent speed can be improved sufficiently. From the viewpoint of the water absorbent speed or other properties, the temperature of the aqueous monomer solution before the temperature is raised is preferably from 0 to 60° C., and more preferably from 20 to 50° C. The time required for raising the temperature is preferably 60 seconds or less, more preferably 30 seconds or less, and still more preferably seconds or less. The aqueous monomer solution is preferably heated rapidly in order to generate bubbles as many as possible.

Figure 4:
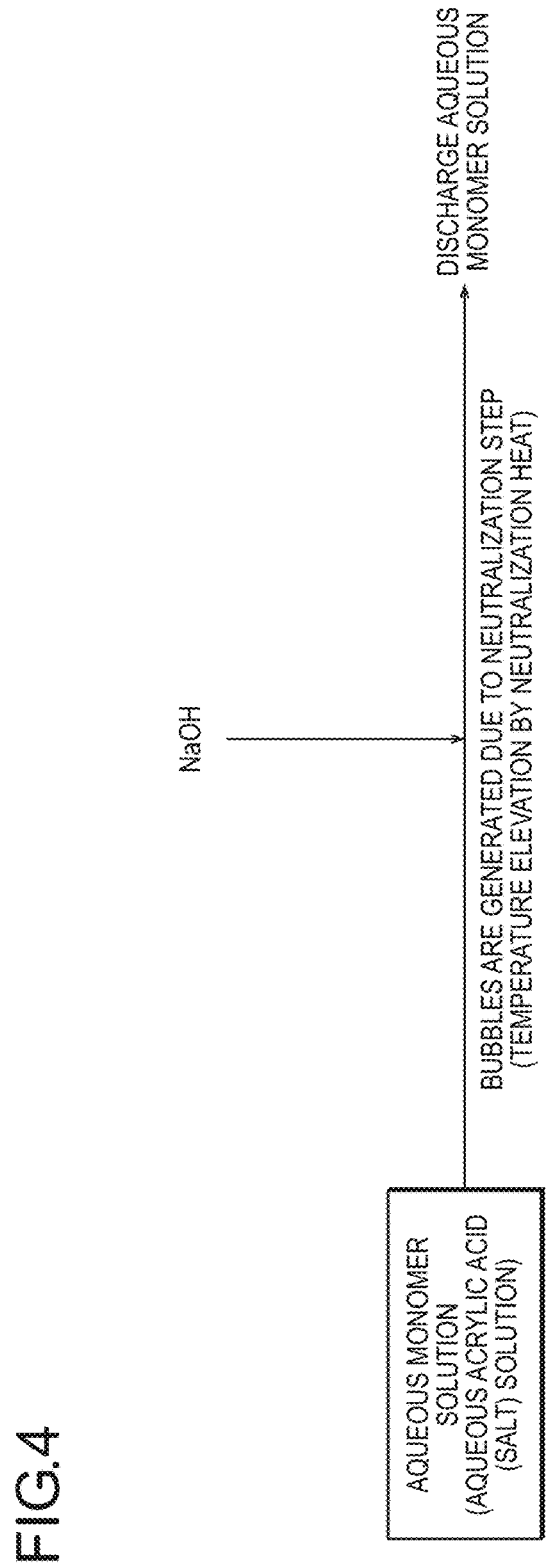
FIG. 4 is a flow diagram schematically illustrating an embodiment in which, as a method for incorporating bubbles, to which the method according to the present invention is applied, the temperature of an acrylic acid (salt)-based aqueous monomer solution is elevated with neutralization heat and bubbles are incorporated.
Figure 5:
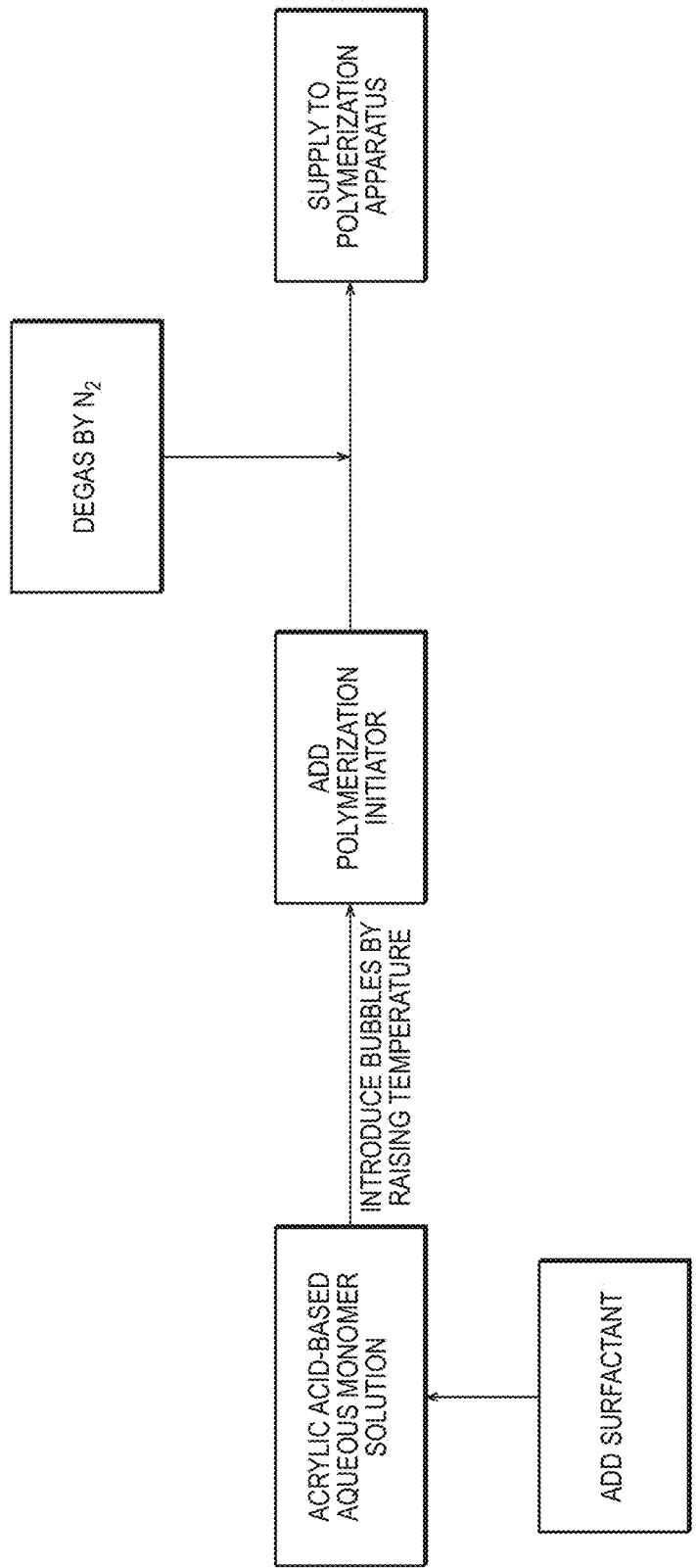
FIG. 5 is a flow diagram schematically illustrating an embodiment in which, as a method for incorporating bubbles, to which the production method according to the present invention is applied, in the generation of bubbles by elevation of the temperature of an acrylic acid-based aqueous monomer solution, deoxidation is performed with an inert gas (for example, nitrogen) before polymerization of the aqueous monomer solution.
Figure 6:
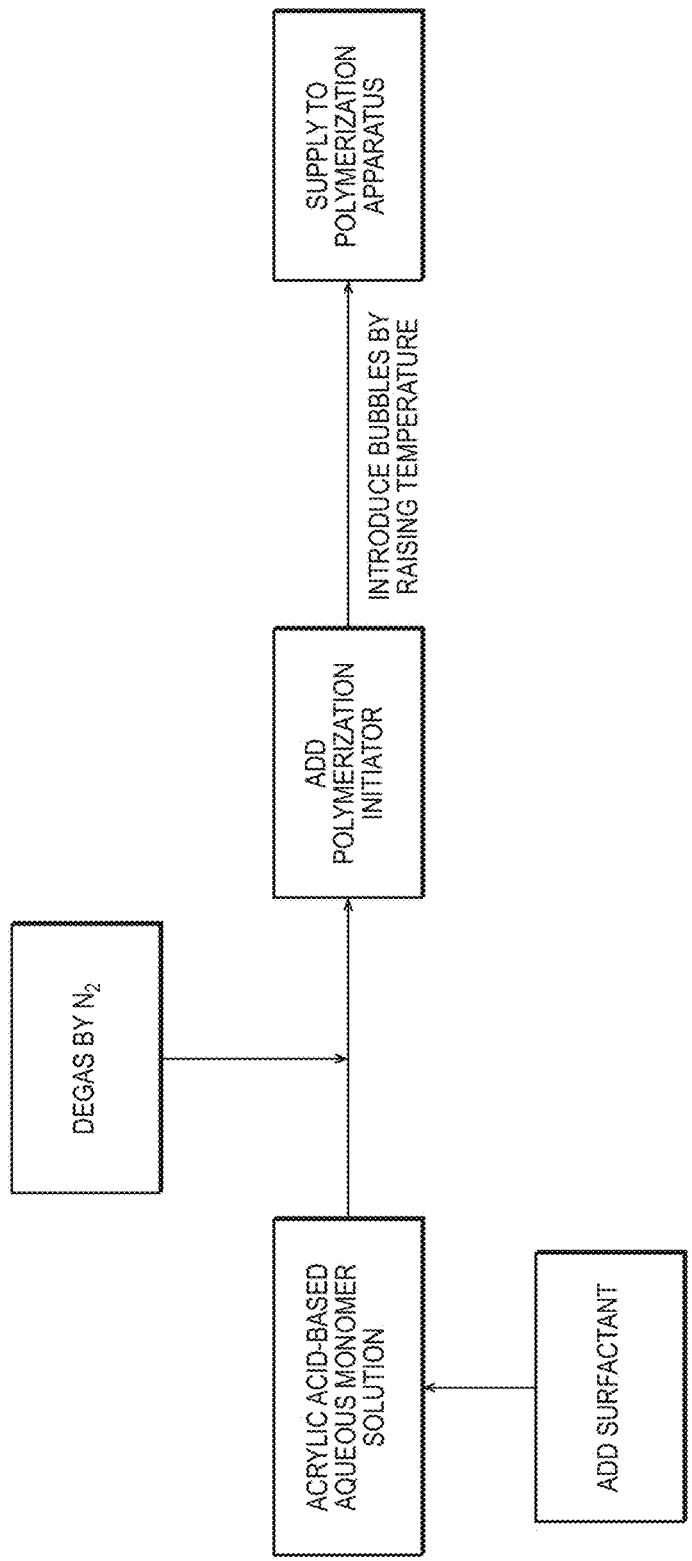
FIG. 6 is a flow diagram schematically illustrating an embodiment in which, as a method for incorporating bubbles, to which the production method according to the present invention is applied, bubbles are incorporated by elevation of the temperature of an acrylic acid (salt)-based aqueous monomer solution and then an inert gas (for example, nitrogen) is further introduced to perform deoxidation before polymerization.
Figure 7:
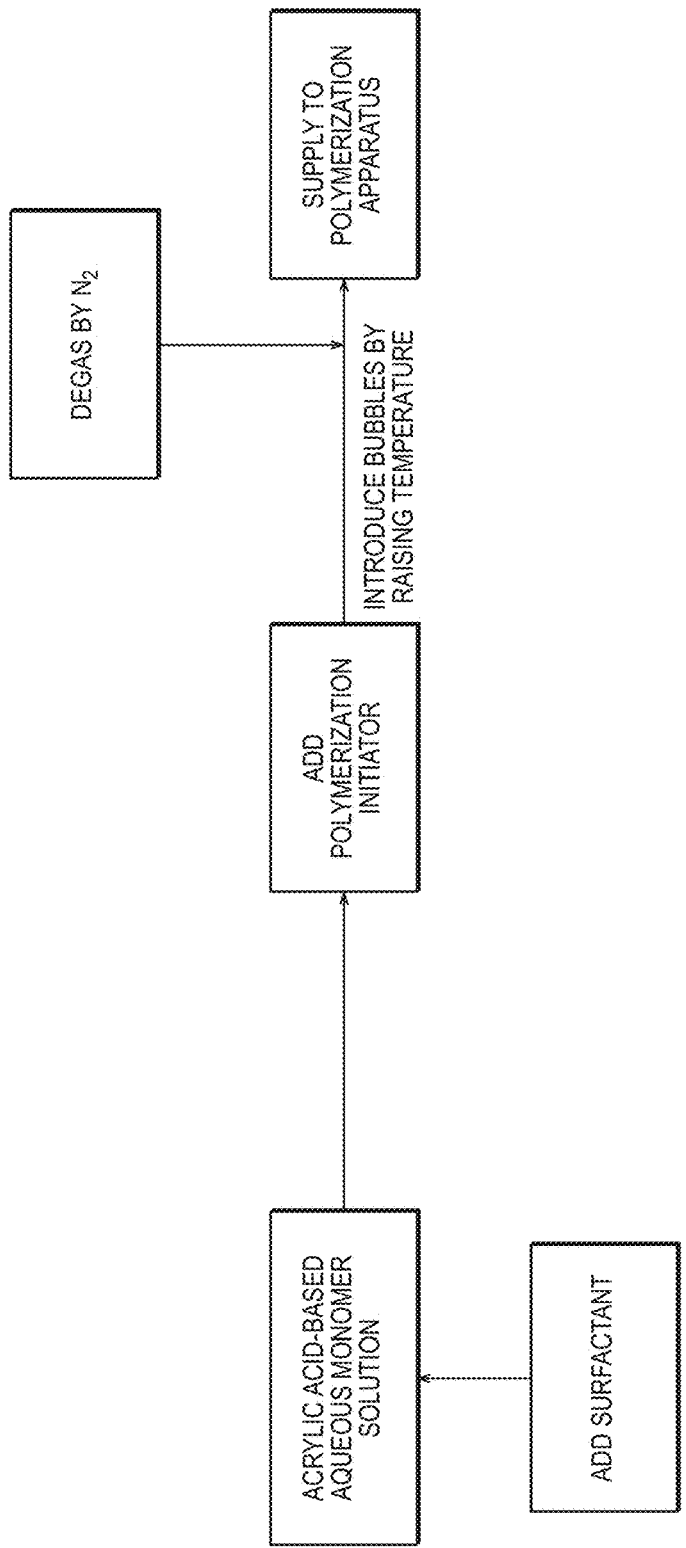
FIG. 7 is a flow diagram schematically illustrating an embodiment in which, as a method for incorporating cells, to which the production method according to the present invention is applied, in the generation of bubbles by elevation of the temperature of an acrylic acid-based aqueous monomer solution, deoxidation is performed with an inert gas (for example, nitrogen) before polymerization of the aqueous monomer solution.
Figure 8:
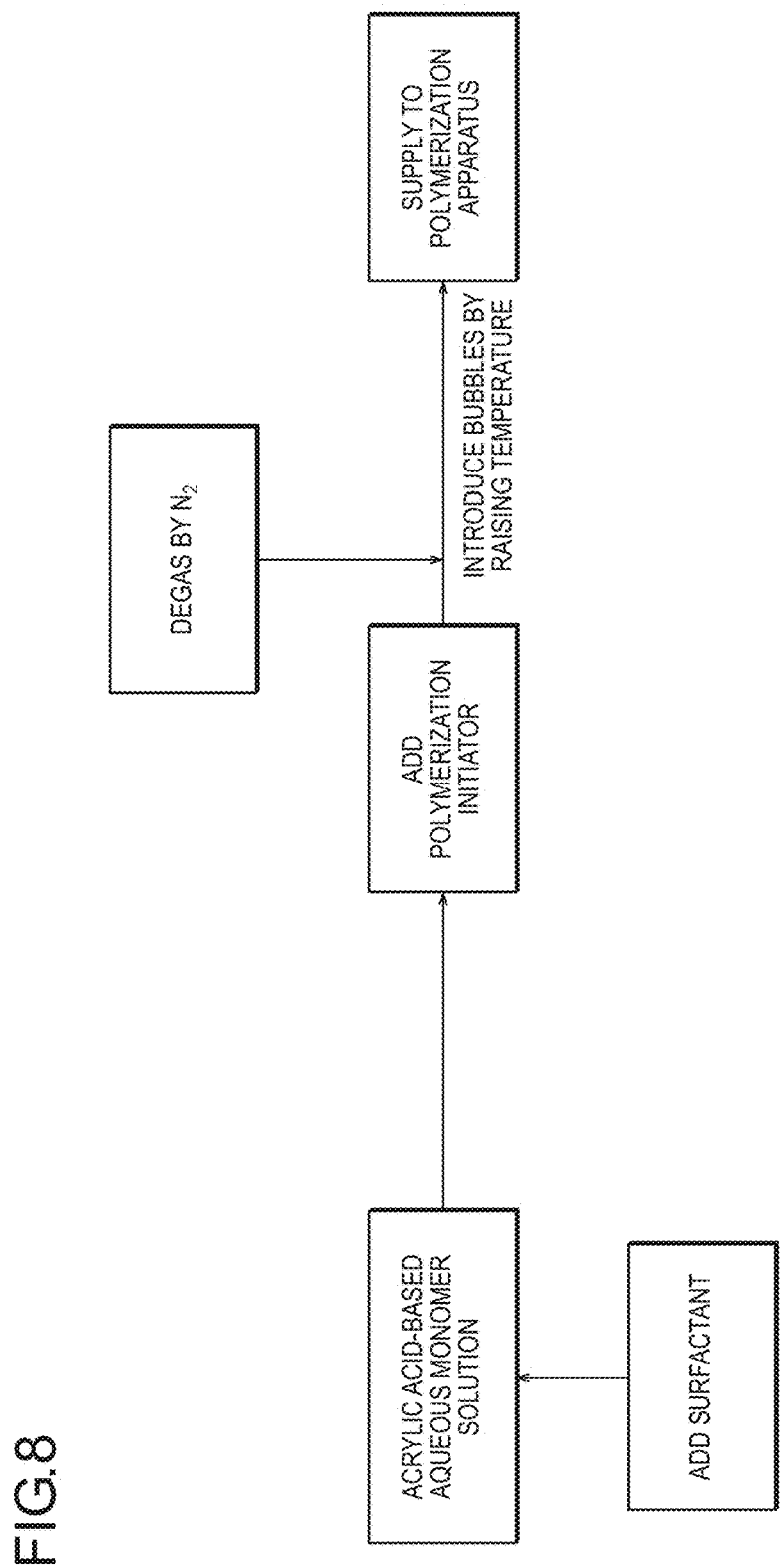
FIG. 8 is a flow diagram schematically illustrating an embodiment in which, as a method for incorporating cells, to which the production method according to the present invention is applied, in the generation of bubbles by elevation of the temperature of an acrylic acid-based aqueous monomer solution, deoxidation is performed with an inert gas (for example, nitrogen) before polymerization of the aqueous monomer solution.
Figure 9:
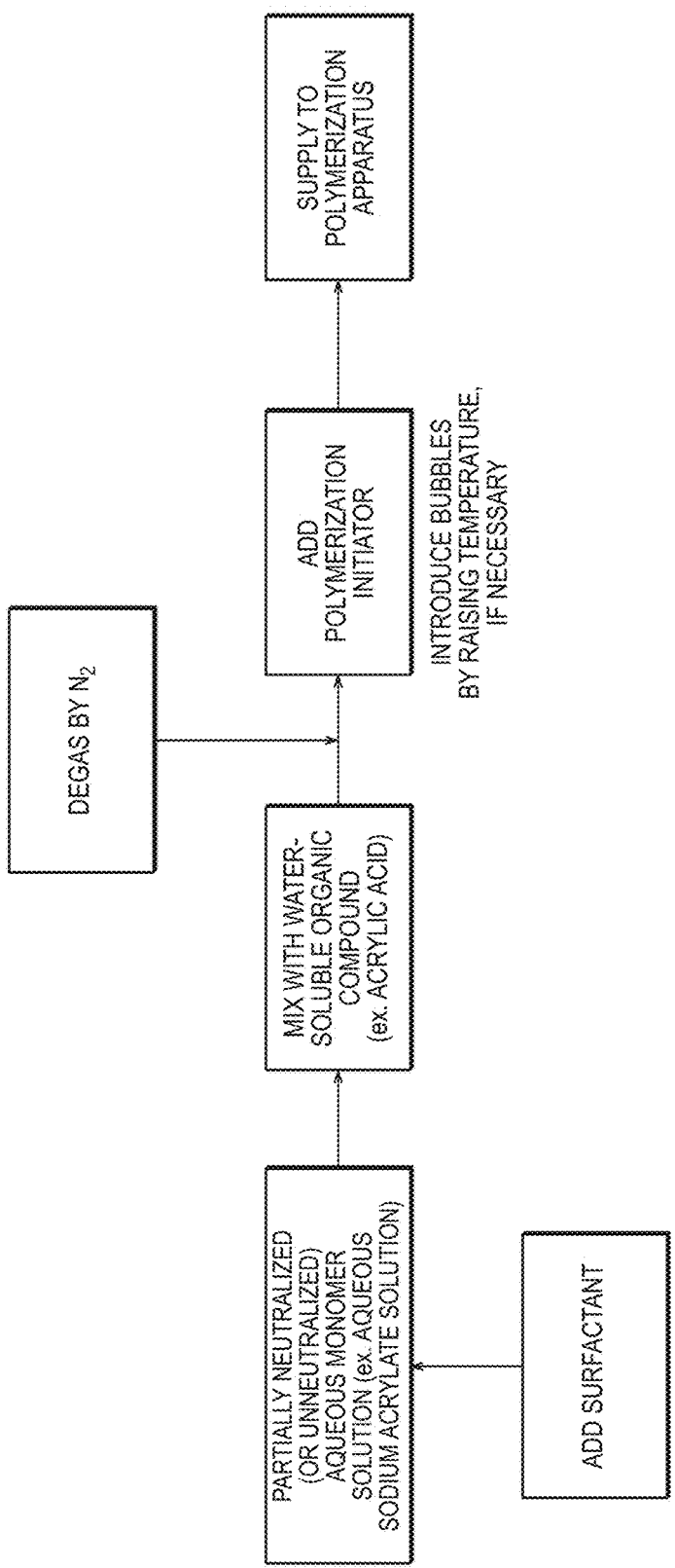
FIG. 9 is a flow diagram schematically illustrating, as a method for incorporating bubbles, to which the production method according to the present invention is applied, reduction in solubility of a gas and generation of bubbles by mixing of a water-soluble organic compound into an acrylic acid-based aqueous monomer solution.
Figure 10:
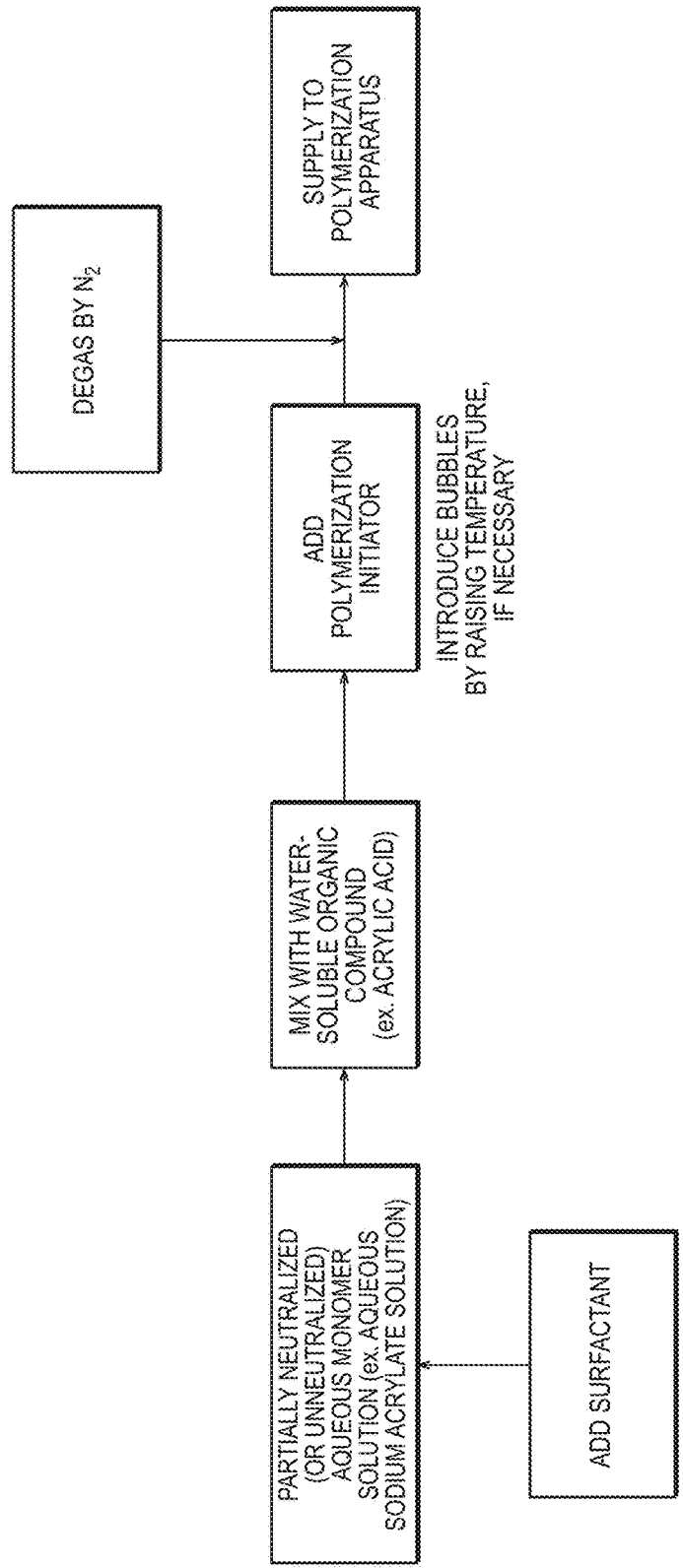
FIG. 10 is a flow diagram schematically illustrating, as a method for incorporating bubbles, to which the production method according to the present invention is applied, reduction in solubility of a gas and generation of bubbles by mixing of a water-soluble organic compound into an acrylic acid-based aqueous monomer solution.

From the viewpoint of easiness of a step and an effect, the temperature is preferably raised by using neutralization heat of (meth)acrylic acid or an aqueous solution thereof containing a surfactant. FIG. 4 is a flow diagram schematically illustrating typical rising of the temperature with neutralization heat and generation of bubbles.

The neutralization heat of (meth)acrylic acid is 13.9 [kcal/mol] (25° C.). The specific heat of water is 1 [cal/° C./g] (25° C.). The specific heat of (meth)acrylic acid is 0.66 [cal/° C./g] (25° C.). An aqueous (meth)acrylic acid solution is preferably heated with this neutralization heat of (meth)acrylic acid. The temperature rising width can be estimated from the neutralization heat and the specific heat.

When the temperature is raised with the neutralization heat of (meth)acrylic acid of 13.9 [kcal/mol] (25° C.), in order to control the width of rising of the temperature, heating or cooling may be performed appropriately during a neutralization reaction, and a reaction system may be thermally insulated during the neutralization reaction.

When the temperature is raised at the stage of preparation of a (meth)acrylic acid (salt)-based aqueous monomer solution, a step for increasing the rate of neutralization of a monomer (neutralization step) may be performed continuously or in a batch. The neutralization step may be performed in one stage or multiple stages (for example, two stages) to a predetermined rate of neutralization. In the neutralization in two stages, base is introduced in two stages as described in Examples below.

In the above method of the present invention, the solubility of a gas is lowered by such an elevation of the temperature, and bubbles are generated in a (meth)acrylic acid aqueous monomer solution. Bubbles generated by such a mechanism (not particularly limiting the present invention) are very fine compared to those obtained by a conventional foaming method. It is presumed that the problem of the present invention will be solved by further stabilizing the bubbles by further using a surfactant and/or a dispersant.

Further, as a method for raising the temperature other than the method for raising the temperature using neutralization heat, a method for raising the temperature by heating a (meth)acrylic acid (salt)-based aqueous monomer solution.

The (meth)acrylic acid (salt)-based aqueous monomer solution is only required to be heated through a jacket or the like.

FIG. 1 illustrates an apparatus (perspective view) in a continuous temperature-rising method by heating a (meth) acrylic acid (salt)-based aqueous monomer solution, to which the method of the present invention can be applied. The apparatus illustrated in FIG. 1 can be used in one method for generating bubbles by raising the temperature of a (meth)acrylic acid (salt)-based aqueous monomer solution. In the apparatus illustrated in FIG. 1, a thermostat bath 100 for raising the temperature of an aqueous monomer solution contains oil 200, and a stainless coil 300 is immersed in the thermostat bath 100. An aqueous monomer solution is supplied through the inside of the stainless coil 300 in the direction indicated by the arrow in the Figure, and is heated by passing though the heated oil 200.

FIGS. 5 to 8 are flow diagrams schematically illustrating embodiments in which the solubility of a gas is lowered by temperature elevation and bubbles are generated, included in the embodiments of the present invention. These methods for raising the temperature may be used together, or another method may be used. In addition, during polymerization, a step for degassing dissolved oxygen (for example, a step for replacement with an inert gas) may be provided, if necessary. Polymerization can be thereby accelerated, physical properties can be improved, and more bubbles can be dispersed in a monomer. In this case, the introduction amount of an inert gas is not particularly limited. The amount of dissolved oxygen in the aqueous monomer solution is preferably 4 mg/l or less, more preferably 2 mg/l or less, and still more preferably 1 mg/l or less. The lower limit of the amount of dissolved oxygen is 0 mg/l, but may be about 0.1 mg/l from the viewpoint of balance with cost of the inert gas.

Method (b): Method for Mixing Water-Soluble Organic Substance into Aqueous Monomer Solution in Preparation of (Meth)Acrylic Acid (Salt)-Based Aqueous Monomer Solution Examples of a method for dispersing bubbles in a (meth) acrylic acid (salt)-based aqueous monomer solution include a method for lowering the solubility of a gas, in preparation by mixing a monomer and/or a salt thereof, and an internal crosslinking agent and water, if necessary, by mixing a water-soluble organic substance having a gas not dissolved or hardly dissolved therein, or a water-soluble organic substance having a smaller amount of gas dissolved therein than the (meth)acrylic acid (salt)-based aqueous monomer solution or water as a mixing object. As the water-soluble organic substance, an organic substance having a solubility of oxygen of preferably 0.02 [ml/ml] or less, more preferably 0.01 [ml/ml] or less, and particularly preferably 0.005 [ml/ml] or less is used. For example, by mixing a monomer (for example, (meth)acrylic acid) not containing a gas into a (meth)acrylic acid (salt)-based aqueous monomer solution containing a gas (having a gas dissolved therein), a gas which cannot be dissolved in the aqueous monomer solution after mixing is generated, and the gas can be dispersed in the aqueous monomer solution as fine bubbles.

(Dissolved Gas)

The number average diameter (volume average particle diameter) of bubbles introduced into a (meth)acrylic acid (salt)-based aqueous monomer solution by the method (a) or (b) is preferably 500 μm or less, more preferably from 50 nm (more preferably 10 μm) to 500 μm, and still more preferably 100 nm (more preferably 10 μm) to 100 μm.

The average diameter of bubbles equal to or more then the lower limit value of the above range makes the surface area large, and makes it possible to secure the water absorbent speed sufficiently. The average diameter equal to or less then the upper limit value of the above range secures the strength of the resulting water-absorbing resin sufficiently.

The solubility of a gas in water is determined depending on the kind of the gas or the temperature. For example, in water at 25° C., the solubility of carbonic acid gas (carbon dioxide) is 1.05 [ml/ml], the solubility of oxygen is 0.0285 [ml/ml], the solubility of nitrogen is 0.0147 [ml/ml]. The solubilities of these gases are lowered by the temperature elevation or mixing of a water-soluble organic substance (preferably (meth)acrylic acid). It is only required to disperse bubbles generated by lowering the solubility in a (meth)acrylic acid aqueous monomer solution with a surfactant or a dispersant. The amount of bubbles is determined appropriately depending on the kind of the gas and the method for lowering the solubility (a degree of temperature elevation or the mixing rate of a water-soluble organic substance). Bubbles are preferably dispersed in a (meth) acrylic acid (salt)-based aqueous monomer solution such that the volume of an aqueous monomer solution becomes preferably from 1.01 to 1.1 times, and more preferably from 1.02 to 1.08 times due to the generated bubbles.

(Gas)

In the production method according to the present invention, bubbles are dispersed by lowering the solubility of a gas dissolved in a (meth)acrylic acid (salt)-based aqueous monomer solution. The bubbles may be dispersed by introducing a gas from the outside separately. That is, it is only required to disperse the bubbles in a (meth)acrylic acid (salt)-based aqueous monomer solution with the bubbles dispersed by lowering the solubility and, if necessary, the bubbles dispersed with a gas further introduced from the outside. In this case, examples of the gas forming the bubbles dispersed in a (meth)acrylic acid (salt)-based aqueous monomer solution include oxygen, air, nitrogen, carbonic acid gas (carbon dioxide), ozone, and a mixture thereof. An inert gas such as nitrogen or carbonic acid gas (carbon dioxide) is preferably used. More preferably, air and nitrogen is particularly preferable from the viewpoint of polymerizability and cost. The pressure during or after introduction of a gas is determined appropriately as a normal pressure, an increased pressure, or a reduced pressure. As a preferable method for introducing a gas from the outside, the method described in Patent Literature 37 can be exemplified.

Specifically, as a method for introducing a gas into a (meth)acrylic acid (salt)-based aqueous monomer solution, a publicly known method such as a static mixer method, a cavitation method, or a Venturi method can be used appropriately. These methods may be used together. Furthermore, introduction of microbubbles (or nanobubbles), which can increase the introduction amount of a gas is preferable.

(2-1-3) Polymerization Step (Particularly, (a3) Polymerization Step for Obtaining Foamed Polymer of Poly (Meth) Acrylic Acid (Salt)-Based Water-Absorbing Resin by Polymerizing Aqueous Sodium Acrylate Solution Having Bubbles Dispersed Therein in Advance of Polymerization)

(Polymerization Method)

Examples of a polymerization method for obtaining the water-absorbing resin of the present invention by the first or second production method include spray polymerization, droplet polymerization, bulk polymerization, precipitation polymerization, aqueous solution polymerization, and reverse phase suspension polymerization. In order to solve the problem of the present invention, the aqueous solution polymerization or the reverse phase suspension polymerization, which uses an aqueous solution of a monomer, is preferable.

In the aqueous solution polymerization, an aqueous monomer solution is polymerized without using a dispersion solvent, and the method is disclosed, for example, in U.S. Pat. No. 4,625,001, U.S. Pat. No. 4,873,299, U.S. Pat. No. 4,286,082, U.S. Pat. No. 4,973,632, U.S. Pat. No. 4,985,518, U.S. Pat. No. 5,124,416, U.S. Pat. No. 5,250,640, U.S. Pat. No. 5,264,495, U.S. Pat. No. 5,145,906, U.S. Pat. No. 5,380,808, EP 0811636 B, EP 0955086 B, EP 0922717 B and the like.

In the reverse phase suspension polymerization, an aqueous monomer solution is polymerized by being suspended in a hydrophobic organic solvent, and the method is disclosed, for example, in U.S. Pat. No. 4,093,776, U.S. Pat. No. 4,367,323, U.S. Pat. No. 4,446,261, U.S. Pat. No. 4,683,274, and U.S. Pat. No. 5,244,735. A monomer, a polymerization initiator, and the like disclosed in these Patent Literatures can be also applied to the present invention.

The concentration of an aqueous monomer solution during polymerization is not particularly limited, but is preferably from 20% by weight to the saturation concentration, more preferably from 25 to 80% by weight, and still more preferably from 30 to 70% by weight. The concentration of 20% by weight or more makes it possible to obtain high productivity, and therefore is preferable. In the meantime, in polymerizing a monomer in the state of a slurry (water dispersion liquid of (meth)acrylate), properties are lowered, and therefore polymerization is preferably performed with a concentration equal to or lower than the saturation concentration (refer to JP 1-318021 A).

The polymerization step in the present invention can be performed at a normal pressure, a reduced pressure, or an increased pressure, but is preferably performed at a normal pressure (or in the vicinity thereof, usually ±10 mmHg). Further, in order to improve the properties by accelerating polymerization, as illustrated in FIGS. 5 to 10, during polymerization, a step for degassing dissolved oxygen (for example, a step for replacement with an inert gas) may be provided, if necessary.

The temperature at the time of initiating polymerization depends on the kind of a polymerization initiator used, and is preferably from 15 to 130° C., and more preferably from 20 to 120° C.

(Polymerization Initiator)

The polymerization initiator used in the present invention is determined appropriately depending on a polymerization form, and is not particularly limited. Examples thereof include a photodecomposition type polymerization initiator, a thermal decomposition type polymerization initiator, and a redox type polymerization initiator. These polymerization initiators initiate polymerization of the present invention.

Examples of the photodecomposition type polymerization initiator include a benzoin derivative, a benzyl derivative, an acetophenone derivative, a benzophenone derivative, and an azo compound. Examples of the thermal decomposition type polymerization initiator include a persulfate such as sodium persulfate, potassium persulfate, or ammonium persulfate; a peroxide such as hydrogen peroxide, t-butyl peroxide, or methyl ethyl ketone peroxide; and an azo compound such as 2,2'-azobis (2-amidinopropane) dihydrochloride or 2,2'-azobis [2-(2-imidazolin-2-yl) propane] dihydrochloride. Examples of the redox type polymerization initiator include a system using a reducing compound such as L-ascorbic acid or sodium bisulfite together with the above persulfate or peroxide. It is also preferable to use the above photodecomposition type polymerization initiator and thermal decomposition type polymerization initiator together. Among these polymerization initiators, an azo polymerization initiator to generate $N_2$ by pyrolysis may be used to accelerate foaming. Furthermore, an active energy ray such as an ultraviolet ray, an electron ray, a γ ray or the like may be used singly or in combination with the above polymerization initiator.

The amount of the polymerization initiator used is preferably from 0.0001 to 1% by mol, and more preferably from 0.0005 to 0.5% by mol per 100% by mol of the monomer. The used amount of 1% by mol or less suppresses deterioration of color hue of the water-absorbing resin particle, and is therefore preferable. The used amount of 0.0001% by mol or more suppresses increase of a residual monomer, and is therefore preferable.

(More Preferable Polymerization Method)

In the present invention, as a method for polymerizing a (meth)acrylic acid (salt)-based aqueous monomer solution, from the viewpoint of the properties of a water-absorbing resin (for example, water absorbent speed or liquid permeability), easiness of controlling polymerization or the like, aqueous solution polymerization is employed. Above all, kneader polymerization or belt polymerization is preferably employed, continuous aqueous solution polymerization is more preferably employed, high concentration continuous aqueous solution polymerization is still more preferably employed, and high concentration and high temperature initiation continuous aqueous solution polymerization is particularly preferably employed.

Preferable examples of the aqueous solution polymerization include continuous belt polymerization (disclosed in U.S. Pat. No. 4,893,999, U.S. Pat. No. 6,241,928, US 2005/215734 A, and the like), continuous kneader polymerization, batch kneader polymerization (disclosed in U.S. Pat. No. 6,987,151, U.S. Pat. No. 6,710,141, and the like), and the like. In such an aqueous solution polymerization, a water-absorbing resin can be produced at high productivity.

Preferable examples of the aqueous solution polymerization include high temperature initiation continuous aqueous solution polymerization in which the polymerization initiation temperature is preferably 40° C. or higher, more preferably 50° C. or higher, still more preferably 60° C. or higher, particularly preferably 70° C. or higher, and most preferably 80° C. or higher (the upper limit is the boiling point), high concentration continuous aqueous solution polymerization in which the concentration of a monomer is preferably 40% by weight or more, more preferably 45% by weight or more, and still more preferably 50% by weight or more (the upper limit is 90% by weight or less, preferably 80% by weight or less, more preferably 70% by weight or less), and high concentration and high temperature initiation continuous aqueous solution polymerization designed by combining them. Foaming is further accelerated by these polymerization methods. In order to further accelerate foaming, it is preferable that the highest temperature reached during polymerization is high. Specifically, the highest temperature reached during polymerization is preferably 100° C. or higher, more preferably from 100 to 130° C., and still more preferably from 105 to 120° C. In the meantime, the above concentration of a monomer is also applied as the solids content of a hydrogel-forming crosslinked polymer after polymerization. Further, by setting the monomer concentration within the above range, stability of fine bubbles is increased, thus the present invention is particularly advantageous.

In the polymerization mentioned above, from the viewpoint of suppressing reduction of the bubbles in an aqueous monomer solution, the polymerization initiation time (time period from the addition of a polymerization initiator to the initiation of polymerization) is preferably more than 0 and 300 seconds or less, and more preferably from 1 to 240 seconds. The polymerization initiation time of 300 seconds or less is preferable since it secures the amount of the cells introduced into a water-absorbing resin particle sufficiently, and exhibits an effect of the present invention.

In the polymerization, if necessary, a chain transfer agent such as hypophosphorous acid (salt), a chelating agent, or the like may be further added to a reaction system before or during polymerization in an amount of preferably 0 to 3% by weight, and more preferably 0.01 to 1% by weight per 100% by weight of a monomer.

(2-1-4) Gel-Crushing Step

In this step, a hydrogel-forming crosslinked polymer (hereinafter, referred to as "hydrogel") obtained through the above polymerization step and the like and containing cells therein is subjected to gel-crushing to obtain a hydrogel in the state of a particulate (hereinafter, referred to as "particulate hydrogel").

By grain refining of the hydrogel by gel-crushing, particularly by gel-crushing using kneading, GCA is improved, and further impact resistance is improved. That is, in order to solve the problem of the present invention, an aqueous solution polymerization is more preferably employed than reverse phase suspension polymerization, which does not require gel-crushing. An aqueous solution polymerization performing gel-crushing during polymerization (for example, kneader polymerization) or after polymerization (for example, belt polymerization, and kneader polymerization, if necessary) is particularly preferably employed.

A gel-crusher which can be used in the present invention is not particularly limited. Examples thereof include a gel-crusher provided with a plurality of rotary stirring blades, such as a batch type or continuous double-arm kneader, a uniaxial extruder, a biaxial extruder, and a meat chopper. Above all, a screw-type extruder having a porous plate at an end thereof is preferable, which includes a screw-type extruder disclosed in JP 2000-063527 A, for example.

In the gel-crushing step in the present invention, the temperature of the hydrogel before gel-crushing (gel temperature) is preferably from 60 to 120° C., and more preferably from 65 to 110° C. from the viewpoint of particle size control or properties. The gel temperature of 60° C. or higher can suppress the increase of hardness caused by a property of a hydrogel, and makes it easy to control the particle shape or the particle size distribution during gel-crushing. The gel temperature of 120° C. or lower can suppress the increase of softness of a hydrogel, and makes it easy to control the particle shape or the particle size distribution, too. The gel temperature can be controlled by the temperature during polymerization, heating or cooling after polymerization, or the like.

The weight average particle diameter (D50) (specified by sieve classification) of the particulate hydrogel after gel-crushing is preferably from 0.5 to 3 mm, more preferably from 0.6 to 2 mm, and still more preferably from 0.8 to 1.5 mm. A proportion of a coarse particulate hydrogel having a particle diameter of 5 mm or more is preferably 10% by weight or less, more preferably 5% by weight or less, and still more preferably 1% by weight or less per 100% by weight of the particulate hydrogel.

(2-1-5) Drying Step

In this step, a hydrogel containing cells obtained through the above polymerization step and the like is dried to obtain a dry polymer. In the meantime, when an aqueous solution polymerization is carried out in the polymerization step, before and/or after the drying of the hydrogel, gel-crushing (grain refining) is performed. Further, the dry polymer (agglomerate) obtained in the drying step may be subjected to a crushing step as it is.

The drying method in the present invention is not particularly limited, and various methods can be employed. Specific examples thereof include heat drying, hot air drying, reduced pressure drying, infrared drying, microwave drying, azeotropic dehydration drying with a hydrophobic organic solvent, and high humidity drying using high temperature steam. One kind of these can be used, or two kinds of these can be used together.

In the present invention, a hydrogel containing cells (particularly, closed cells) is obtained through the above polymerization step and the like. Foaming of the hydrogel containing cells is further accelerated during drying at a high temperature. Therefore, the drying temperature in the present invention is preferably from 100 to 300° C., and more preferably from 150 to 250° C. The drying time depends on the surface area and the moisture content of the hydrogel, the kind of a dryer, and the like, and therefore is, for example, preferably from one minute to five hours, and more preferably from five minutes to one hour. Further, the solids content of a water-absorbing resin determined from a drying loss (1 g of powder or particles is dried at 180° C. for three hours) is preferably 80% by weight or more, more preferably from 85 to 99% by weight, still more preferably from 90 to 98% by weight, and particularly preferably from 92 to 97% by weight.

(2-1-6) Crushing and Classification Step (Particularly, (c) Sizing Step for Making a Proportion of Particles Having a Particle Diameter of 150 to 850 μm (Specified by Standard Sieve) to be 95 to 100% by Weight Per 100% by Weight of all the Particles)

In this step, the dry polymer obtained in the drying step or a granule obtained by the granulation in (2-2) described below is crushed and/or classified to preferably obtain water-absorbing resin particles having a specific particle size, and this step is particularly a sizing step. This step is different from the above (2-1-4) gel-crushing step in that the object of crushing has passed through the drying step. Further, the water-absorbing resin after the crushing step is also referred to as a crushed product.

This step (sizing step) is performed before and/or after (2-4) surface crosslinking step, is preferably performed before (2-4) surface crosslinking step, and is more preferably performed at least two times before and after (2-4) surface crosslinking step.

Examples of an apparatus (crusher) used in the crushing step in the present invention include a high-speed rotary crusher such as a roll mill, a hammer mill, a screw mill and a pin mill, a vibration mill, a knuckle type crusher, and a cylindrical mixer. These apparatuses are used together, if necessary.

(Particle Size)

The weight average particle diameter (D50) of a water-absorbing resin particle before surface crosslinking is preferably from 300 to 500 μm, more preferably from 310 to 480 μm, and still more preferably from 320 to 450 μm from the viewpoint of handleability (particularly, handleability under moisture absorption), GCA, the water absorbent speed, the fluid retention capacity under pressure, or the like. Smaller content of fine particles having a particle diameter of less than 150 μm specified by standard sieve classification is better. The content is preferably from 0 to 5% by weight, more preferably from 0 to 3% by weight, and still more preferably from 0 to 1% by weight per 100% by weight of the water-absorbing resin particles. Further, smaller content of coarse particles having a particle diameter of 850 μm or more specified by standard sieve classification is better. The content is preferably from 0 to 5% by weight, more preferably from 0 to 3% by weight, and still more preferably from 0 to 1% by weight per 100% by weight of the water-absorbing resin particles from the viewpoint of the water absorbent speed or the like. Moreover, the proportion of particles having a particle diameter of 150 μm or more and less than 850 μm is preferably 90% by weight or more, more preferably 95% by weight or more, still more preferably 98% by weight or more, and particularly preferably 99% by weight or more (the upper limit is 100% by weight) per 100% by weight of the water-absorbing resin particles from the viewpoint of GCA, the water absorbent speed, the fluid retention capacity under pressure, or the like. Furthermore, the logarithmic standard deviation (σζ) in the particle size distribution is preferably from 0.20 to 0.50, more preferably from 0.25 to 0.45, and still more preferably from 0.30 to 0.40. When the content of fine particles of less than 150 μm to a small value as the above range, dusting is reduced, and flowability under moisture absorption is improved. Therefore, handling becomes easier, GCA is improved, and the fluid retention capacity under pressure is improved.

Control of the particle size can be performed during polymerization, during gel-crushing, or during crushing or classification after drying, and is particularly preferably performed during classification after drying. Further, the particle size is measured using a JIS standard sieve in conformity with the method specified by WO 2004/69915 A or EDANA-ERT420.2-02.

In order to further solve the problem of the present invention, the particle size is also applied to a particulate water-absorbing agent as the final product after the surface crosslinking.

Fine particles (for example, particles passing through a wire mesh of 150 μm) generated by the control of the particle size may be discarded or recovered according to a recovery method into an aqueous monomer solution before polymerization (WO 92/001008 A and WO 92/020723 A) or a recovery method into a hydrogel during polymerization (WO 2007/074167 A, WO 2009/109563 A, WO 2009/153196 A, and WO 2010/006937 A) as known conventionally. The fine particles are preferably subjected to a granulation treatment by (2-2) described below to obtain water-absorbing resin particles suitable for the present invention.

The shape of the water-absorbing resin particles of the present invention is not particularly limited, and examples thereof include a spherical shape, a fibrous shape, a rod shape, a nearly spherical shape, a flat shape, an irregular shape, a granulated particle shape, and a particle having a porous structure. Here, an irregularly-crushed shape obtained through a crushing step to a hydrogel or a dry polymer, or a granule thereof is preferable from the viewpoint of the water absorbent speed. In the meantime, when the particles having irregularly-crushed shape are used in admixture with other particles such as spherical particles, the particles content having irregularly-crushed shape is preferably from 70 to 100% by weight, more preferably from 85 to 100% by weight, and particularly preferably from 95 to 100% by weight.

In the present invention, the term "particles having irregularly-crushed shape" refers to particles obtained by drying a water-containing polymer obtained by aqueous solution polymerization or the like and then crushing the dried polymer, and refers to particles in which a fracture surface (smooth surface) due to crushing and an angle are observed with an electron microscope or an optical microscope.

(2-2) Method for Granulating (Meth)Acrylic Acid (Salt)-Based Water-Absorbing Resin Fine Particles to Obtain Granules of Water-Absorbing Resin Particles (Particularly, (a1) Step for Granulating Poly (Meth)Acrylic Acid (Salt)-Based Water-Absorbing Resin Having an Average Particle Diameter of 10 to 180 μm)

In the present invention, granulation means formation of a particle larger than the original particle by attaching the particles together by a physical or chemical method. The particle obtained in this way is referred to as a granule or a granulated particle.

The composition of the water-absorbing resin used in the granulation step in the present invention is not particularly limited as long as the water-absorbing resin is a poly (meth)acrylic acid (salt)-based water-absorbing resin. The water-absorbing resin is preferably a water-absorbing resin having a composition described in (2-1-1).

Further, the water-absorbing resin used in the granulation step in the present invention is preferably produced by introducing a foamed structure as described in (2-1). However, the water-absorbing resin is not limited to such a product, and a water-absorbing resin obtained by a conventionally known method may be used. Examples of the conventionally known method include aqueous solution polymerization, reverse phase suspension polymerization, spray polymerization, droplet polymerization, bulk polymerization, and precipitation polymerization.

The shape of the water-absorbing resin used in the granulation step in the present invention is not particularly limited. Examples thereof include a spherical shape, a fibrous shape, a rod shape, a nearly spherical shape, a flat shape, an irregular shape, a granulated particle shape, and a particle having a porous structure. An irregularly-crushed shape obtained through a crushing step to a hydrogel or a dry polymer is preferable from the viewpoint of the water absorbent speed.

The weight average particle diameter of the water-absorbing resin used in the granulation step in the present invention is preferably from 10 μm to 200 μm, more preferably from 15 μm to 180 μm, and still more preferably from 20 μm to 160 μm. The proportion of particles having a particle diameter of more than 200 μm is preferably 30% by weight or less, more preferably 20% by weight or less, still more preferably 15% by weight or less, and particularly preferably 10% by weight or less per 100% by weight of the water-absorbing resin particles. The weight average particle diameter equal to or less than the upper limit value of these ranges is preferable since the risk of lowering GCA or water absorbent speed is reduced. The weight average particle diameter equal to or more than the lower limit value of these ranges is also preferable since the increase in crushing cost for obtaining the fine particles or the decrease in strength of the granulated particles due to non-uniform granulation is reduced.

The water-absorbing resin used in the granulation step in the present invention may be pulverized for this granulation step, or obtained by fractionating water-absorbing resin fine particles generated in the crushing step of the water-absorbing resin by a classification operation.

In the pulverization, a crusher exemplified in (2-1-6) Crushing and classification step can be used. Further, in the fractionating, water-absorbing resin fine particles can be obtained by using a sieve having an opening of 100 μm to 300 μm. At this time, the weight average particle diameter (D50) of the water-absorbing resin fine particles is preferably 200 μm or less, and more preferably 180 μm or less.

The water-absorbing resin used in the granulation step in the present invention is preferably a non-surface crosslinked water-absorbing resin, but may be a surface crosslinked water-absorbing resin or may be a mixture of a surface crosslinked water-absorbing resin and a non-surface crosslinked water-absorbing resin. Further, the water-absorbing resin may be a mixture of water-absorbing resins having different compositions and different absorption capacities.

Furthermore, by adding a surface crosslinking agent in the granulation step, the granulation step and the surface crosslinking step may be performed simultaneously. In order to obtain the particulate water-absorbing agent of the present invention, the surface crosslinking step is preferably performed after the granulation step.

CRC of the water-absorbing resin used in the granulation step in the present invention is preferably 10 g/g or more, more preferably 15 g/g or more, still more preferably 20 g/g or more, still more preferably 25 g/g or more, and particularly preferably 28 g/g or more. The upper limit value is not particularly limited, but is preferably 100 g/g or less, more preferably 80 g/g or less, and still more preferably 60 g/g or less.

In order to obtain the water-absorbing resin granules of the present invention, various polymers such as a polyanion including a polyanion and polyethylene imine, and a nonion, a polyhydric alcohol such as glycerin, or water can be used as a granulation binder thereof. Examples of a specific method therefor include methods described in Patent Literatures 10 to 17. From the viewpoint of properties and safety, granulation is preferably performed by essentially using an aqueous liquid as a binder.

In the present invention, as an example of a method of granulation using an aqueous liquid as a binder, a method of granulation after an aqueous liquid is heated in advance, described in U.S. Pat. No. 7,153,910, will be described below. In addition, a method of granulation using water vapor described in JP 2005-54151 A, and water vapor and an aqueous liquid described in WO 2009/031701 A will be described. The disclosed contents are incorporated by reference, and are included in the disclosed contents of the present application.

Hereinafter, a preferable method of granulation will be described.

A method for obtaining water-absorbing resin granules using an aqueous liquid in the present invention is not particularly limited, and a wide range of methods including the methods of the above Patent Literatures 11 to 20 can be applied. In this case, examples thereof include a rolling granulation method, a compression granulation method, a stirring granulation method, an extrusion granulation method, a crushing granulation method, a fluidized bed granulation method, and a spray-drying granulation method. Among these granulation methods, the stirring method is most conveniently used.

As an apparatus used for performing this method, a continuous apparatus and a batch type apparatus, each of which includes a vertical apparatus and a horizontal apparatus, can be used. The vertical continuous granulator includes a spiral pin mixer manufactured by Pacific Machinery & Engineering Co., Ltd. and a flow jet mixer manufactured by Funken Powtechs, Inc. The horizontal continuous granulator includes an annular layer mixer manufactured by Dreisberke Co., Ltd. The vertical batch granulator includes a Henschel mixer manufactured by Mitsui Mining Co., Ltd. and a turbo sphere mixer manufactured by Moritz, Co., Ltd. The horizontal batch granulator includes a little ford mixer manufactured by Lodige Co., Ltd. and a multi flux mixer manufactured by Gercke Co., Ltd.

In the present invention, an aqueous liquid mixed with water-absorbing resin particles is not particularly limited. For example, water or an aqueous liquid containing a water-soluble salt or a hydrophilic organic solvent can be used. From the viewpoint of properties and the granulation strength, it is preferable that water occupies 90% by weight or more, preferably 99% by weight or more, and more preferably 99 to 100% by weight of the aqueous liquid, and the aqueous liquid particularly preferably includes only water.

The amount of the aqueous liquid used is usually 1 part by weight or more, and preferably 5 parts by weight or more per 100 parts by weight of the water-absorbing resin particles. As in the methods described in Patent Literatures 19 and 20, from the viewpoint of the granulation strength, it is preferable that the used amount is from 80 to 280 parts by weight. The used amount of the aqueous liquid of 280 parts by weight or less makes handling as a granule easy, and is advantageous in terms of drying cost. On the other hand, the used amount of the aqueous liquid of 80 parts by weight or more secures sufficient granulation strength an excellent characteristic can be exhibited in the final product. In addition, granules formed by being uniformly mixed can be obtained.

Conventionally, as a method for compounding a plurality of water-absorbing resin particles into a particle shape, the above granulation is known, and water or an aqueous liquid has been often used as a binder. However, even when a high-speed stirring type mixer (U.S. Pat. No. 5,002,986 and U.S. Pat. No. 4,734,478 described above), a specific spray continuous granulator (U.S. Pat. No. 5,369,148), a fluidized bed (EP 0318989 B), or the like is used, the addition amount of water is at most about 30 parts by weight per 100 parts by weight of the water-absorbing resin due to a problem of a mixing property of water. In contrast, by using a sufficient amount of an aqueous liquid in the present invention, sufficient granulation strength is secured, and the present invention is easily achieved.

In a method of using a mixing auxiliary agent such as an insoluble inorganic powder or a water-soluble polymer in order to improve a mixing property of water in granulation (EP 064424 B), mixing is still not uniform, and the use of the mixing auxiliary agent rather causes reduction in the granulation strength or properties. Apart from the method for mixing water-absorbing resin particles with an aqueous liquid to directly obtain particulate water-absorbing resin granules including a plurality of particles, as another method, a method for kneading a water-absorbing resin as a hydrogel and then further crushing the gel has been also proposed. For example, when a shear mixer (EP 0417761 B) or a Nauta type mixer (U.S. Pat. No. 4,950,692) is used for mixing the fine particles with an aqueous liquid, water in an amount of more than 100 parts by weight can be added and mixed due to a strong shear force thereof. However, the fine particles are integrated and not formed into a particle shape. In addition, there is a problem that kneading with a very large force deteriorates the water-absorbing resin due to the shear force.

Therefore, in order to improve the granulation strength of the water-absorbing resin granules without deteriorating the properties, it is important to set the addition amount of the aqueous liquid to the water-absorbing resin within a predetermined range and to obtain the particulate water-absorbing resin granules directly. In the meantime, the phrase "obtain a particulate water-absorbing resin granules directly" means obtaining a particulate water-absorbing resin having a specific particle size by agglomerating a plurality of particles, not by a method of obtaining an integrated gel by kneading or the like and then crushing or fragmenting the huge gel.

Among the granulation methods, particularly, when a large amount of aqueous liquid (for example, from 80 to 280 parts by weight) is mixed to further improve the granulation strength or the fluid retention capacity under pressure, as in the methods described in Patent Literatures 19 and 20, a method for heating the aqueous liquid in advance before mixing and then performing granulation is preferably used due to an excellent mixing property thereof. That is, preferable water-absorbing resin granules in the present invention include granules obtained by mixing an aqueous liquid having water-absorbing resin granules heated in advance with water-absorbing resin particles at a high speed. In the meantime, the water-absorbing resin granules in the present invention refers to granules containing a plurality of water-absorbing resin particles, and the particle diameter of the granules is 20 mm or less, preferably from 0.3 to 10 mm, and more preferably from 0.3 to 5 mm. In the present invention, the water-absorbing resin granules are a generic term for water-containing or dry granules. Water-absorbing resin granules after being dried are also referred to separately as dry water-absorbing resin granules having a moisture content of 10% by weight or less.

By using a heated aqueous liquid, mixing can be performed uniformly even without kneading water-absorbing resin particles and the aqueous liquid and even without using a mixing auxiliary agent, which causes reduction in the properties. Further, by using a heated aqueous liquid, particulate agglomerates having a proper size and having individual water-absorbing resin particles agglomerated, that is, water-absorbing resin granules suitable for the present invention is obtained.

The granules can be confirmed with an optical microscope by the fact that a plurality of individual particles are gathered and agglomerated while keeping the shapes thereof or the fact that the particles are swelled as a plurality of discontinuous particles during liquid absorption. By using the method for granulating after heating the aqueous liquid in advance before mixing as described above, it has become possible for the first time to obtain particulate water-absorbing resin granules consisting essentially of water and fine particles without using a mixing auxiliary agent conventionally used for granulation and without crushing a gel used for a purpose other than granulation. So, the method is more preferable.

The aqueous liquid used for the granulation includes, for example, water, an aqueous solution containing a hydrophilic organic solvent described below, and heated water containing a small amount of crosslinking agent. In this case, as the crosslinking agent, surface crosslinking agents of the kinds or the amounts used to be described below can be used. By using a crosslinking agent together with the aqueous liquid, water soluble component may be reduced, or the granulation strength may be further improved.

Hereinafter, further description will be given. An aqueous liquid is heated usually to 40° C. or higher, preferably to 50° C. or higher, more preferably to 60° C. or higher, and still more preferably to 70° C. or higher. Further, the upper limit is the boiling point of the aqueous liquid or lower. The boiling point may be adjusted variously by adding a salt or another solvent or changing the pressure (reducing or increasing the pressure) or the like. However, even when the temperature is higher than 100° C., there is no large change, and therefore heating is usually performed at 100° C. or lower.

The aqueous liquid supplied in the granulation step may be in the form of liquid, or it can be supplied as water vapor. Furthermore, the aqueous liquid and water vapor may be supplied in combination.

It is preferable that the heated aqueous liquid and the water-absorbing resin particles are mixed at a high speed. Mixing at a high speed means that the period of time from the time of contact between the aqueous liquid and the water-absorbing resin particles to generation of water-absorbing resin granules, i.e., a mixing time, is short in mixing the aqueous liquid and the water-absorbing resin particles. The mixing time is preferably three minutes or less, more preferably one minute or less, and most preferably from one to 60 seconds.

The mixing time of three minutes or less makes it easy to mix the aqueous liquid and the water-absorbing resin particles uniformly and suppresses generation of huge agglomerate. As a result, it is possible to obtain water-absorbing resin granules which are desired in the present invention. Further, when mixing is continued for a long time after the completion of mixing, the water-absorbing resin may be deteriorated, for example, a water soluble component may be increased or the fluid retention capacity under pressure may be reduced for the water-absorbing resin. As long as the above mixing at a high speed can be achieved, a mixer used is not particularly limited. A container fixed-type mixer is preferable, and a mechanical stirring type mixer is particularly preferable. Examples of such a mechanical stirring type mixer include a turbulizer (manufactured by Hosokawa Micron Corp.), a Lodige mixer (manufactured by Lodige Co., Ltd.), a mortar mixer (manufactured by Nishinihon Shikenki Co., Ltd.), a Henschel mixer (manufactured by Mitsui Mining Co., Ltd.), a turbo sphere mixer (manufactured by Moritz Co. Ltd.), and a multi flux mixer (manufactured by Gercke Co., Ltd.). Either a batch type mixer or a continuous mixer may be used.

The water-absorbing resin granules of the present invention, obtained as described above, particularly preferably the water-absorbing resin granules obtained by a method of granulation by mixing 100 parts by weight of water-absorbing resin particles and 80 to 280 parts by weight of an aqueous liquid after heating the aqueous liquid in advance before mixing, is subsequently dried to improve the granulation strength. By drying the water-absorbing resin granules, fine particles are integrated more firmly and are regenerated so as to have strength at the same level as primary particles.

A drying method is not particularly limited, and a usual dryer or heating furnace can be widely used. Specifically, drying is only required to be performed within the range of the temperature, time, and solids content described in (2-1-5). Drying at such a high temperature is preferable since water-absorbing resin granules are contracted during drying, and results in a firm dry granulate. Only the water-absorbing resin granules obtained in the present invention may be dried, or the water-absorbing resin granules may be dried together with a polymerized gel before drying, obtained by the aqueous solution polymerization or the reverse phase suspension polymerization described above.

The dry water-absorbing resin granules thus obtained are contracted by drying to become firm granules, and may be crushed to adjust the particle size, if necessary. Preferable methods for crushing and adjustment of the particle size are described in (2-1-6) above.

Water-absorbing resin fine particles generated again by crushing and adjustment of the particle size (for example, particles passing through a wire mesh of 150 μm) may be granulated again by using an aqueous liquid as a binder.

(2-3) Step for Adding Surface Crosslinking Agent (Particularly, (b) Surface Crosslinking Step of Granule or Surface Crosslinking Step of Foamed Polymer)

In this step, the above granules or the above foamed polymer is mixed with a surface crosslinking agent to prepare water-absorbing resin particles containing a surface crosslinking agent subjected to a surface crosslinking step. In general, surface crosslinking is performed by addition of an organic surface crosslinking agent described below; polymerization of a monomer (polymerizable surface crosslinking agent) on the surface of water-absorbing resin particles; addition of a radical polymerization initiator (surface crosslinking agent in a broad sense) such as a persulfate and heating or irradiation with an ultraviolet ray, or the like. In the present invention, it is preferable to add an organic surface crosslinking agent to the water-absorbing resin obtained in (2-1) or (2-2) above.

(Organic Surface Crosslinking Agent)

As the organic surface crosslinking agent which can be used in the present invention, from the viewpoint of properties of the resulting water-absorbing resin particles, an organic compound having a reactive group (for example, a hydroxy group and/or an amino group) to perform a dehydration esterification reaction or a dehydration amidation reaction with a carboxyl group as a functional group of a poly (meth)acrylic acid (salt)-based water-absorbing resin particles. The organic compound is not limited to an alcohol compound and an amine compound directly having a hydroxy group or an amino group, and includes even a cyclic compound having a reactive group to generate a hydroxy group or an amino group and/or a reactive group to directly react with the carboxyl group (for example, an alkylene carbonate compound and an oxazolidinone compound).

Examples of the organic surface crosslinking agent include a polyhydric alcohol compound, an epoxy compound, a polyvalent amine compound or a condensate thereof with a haloepoxy compound, an oxazoline compound, a (mono-, di-, or poly-) oxazolidinone compound, an oxetane compound, and an alkylene carbonate compound. A polyhydric alcohol compound, an alkylene carbonate compound, and an oxazolidinone compound are more preferable.

Specific examples of the organic surface crosslinking agent include a polyalcohol compound such as (di-, tri-, tetra-, or poly-) ethylene glycol, (di- or poly-) propylene glycol, 1,3-propanediol, 2,2,4-trimethyl-1,3-pentanediol, (poly) glycerin, 2-butene-1,4-diol, 1,4-butanediol, 1,3-butanediol, 1,5-pentanediol, 1,6-hexanediol, trimethylolpropane, di- or tri-ethanolamine, pentaerythritol, or sorbitol; an epoxy compound such as (poly) ethylene glycol diglycidyl ether, (di- or poly-) glycerol polyglycidyl ether, or glycidol; an oxazoline compound such as 2-oxazolidone, N-hydroxyethyl-2-oxazolidone, or 1,2-ethylene bisoxazoline; an alkylene carbonate compound such as 1,3-dioxolan-2-one, 4-methyl-1,3-dioxolan-2-one, 4,5-dimethyl-1,3-dioxolan-2-one, 4,4-dimethyl-1,3-dioxolan-2-one, 4-ethyl-1,3-dioxolan-2-one, 4-hydroxymethyl-1,3-dioxolan-2-one, 1,3-dioxan-2-one, 4-methyl-1,3-dioxan-2-one, 4,6-dimethyl-1,3-dioxan-2-one, or 1,3-dioxopan-2-one; a haloepoxy compound such as epichlorohydrin, epibromohydrin, or α-methyl epichlorohydrin and a polyvalent amine adduct thereof (for example, Kaimen manufactured by Hercules Inc.; registered trademark); a silane coupling agent such as γ-glycidoxypropyltrimethoxysilane or γ-aminopropyltriethoxysilane; an oxetane compound such as 3-methyl-3-oxetane methanol, 3-ethyl-3-oxetane methanol, 3-butyl 3-oxetane methanol, 3-methyl-3-oxetane ethanol, 3-ethyl-3-oxetane ethanol, 3-butyl-3-oxetane ethanol, 3-chloromethyl-3-methyloxetane, 3-chloromethyl-3-ethyloxetane, or a polyvalent oxetane compound; and a cyclic urea compound such as 2-imidazolidinone.

As the polyhydric alcohol, a polyhydric alcohol having 2 to 8 carbon atoms is preferable, a polyhydric alcohol having 3 to 6 carbon atoms is more preferable, and a polyhydric alcohol having 3 or 4 carbon atoms is still more preferable. Furthermore, a diol is preferable, and examples thereof include ethylene glycol, propylene glycol, 1,3-propanediol, and 1,4-butanediol. A polyhydric alcohol selected from propylene glycol, 1,3-propanediol, and 1,4-butanediol is preferable.

Further, as the epoxy compound, a polyglycidyl compound is preferable, and ethylene glycol diglycidyl ether is preferably used. As the oxazoline compound, 2-oxazolidinone is preferably used. As the alkylene carbonate compound, 1,3-dioxolan-2-one (ethylene carbonate) is preferably used.

Furthermore, two or more compounds selected from the polyhydric alcohol compound, the epoxy compound, the oxazoline compound, and the alkylene carbonate compound are preferably used in combination. From the viewpoint of higher properties, a combination of a polyhydric alcohol and an organic surface crosslinking agent other than the polyhydric alcohol is preferable, a combination of a polyhydric alcohol and an epoxy compound or an alkylene carbonate compound is more preferable, and a combination of a polyhydric alcohol and an alkylene carbonate compound is still more preferable.

When combining a plurality of the organic surface crosslinking agents, especially combining the polyhydric alcohol and an organic surface crosslinking agent other than the polyhydric alcohol, the ratio (the weight ratio) is, which is expressed as polyhydric alcohol:any compound other than polyhydric alcohol, preferably from 1:100 to 100:1, more preferably from 1:50 to 50:1, and still more preferably from 1:30 to 30:1.

(Solvent and Concentration)

The total addition amount of the organic surface crosslinking agent is preferably from 0.001 to 15 parts by weight, and more preferably from 0.01 to 5 parts by weight per 100 parts by weight of the water-absorbing resin before addition.

Further, when two kinds of the compounds, that is, a polyhydric alcohol compound and a compound other than the polyhydric alcohol are used as the organic surface crosslinking agent, the total amount of the polyhydric alcohol compound is preferably from 0.001 to 10 parts by weight, and more preferably from 0.01 to 5 parts by weight, and the total amount of the compound other than the polyhydric alcohol is preferably from 0.001 to 10 parts by weight, and more preferably from 0.01 to 5 parts by weight per 100 parts by weight of the water-absorbing resin before addition.

The organic surface crosslinking agent is preferably added as an aqueous solution. The amount of water used for the aqueous solution is preferably from 0.5 to 20 parts by weight, and more preferably from 0.5 to 10 parts by weight as the total amount per 100 parts by weight of the water-absorbing resin before the addition treatment. In the meantime, the amount of water also includes crystal water, hydrated water and the like of a surface crosslinking agent.

Furthermore, a hydrophilic organic solvent may be added to the organic surface crosslinking agent aqueous solution. In this case, the amount of the hydrophilic organic solvent is preferably more than 0 part by weight and 10 parts by weight or less, and more preferably more than 0 part by weight and 5 parts by weight or less per 100 parts by weight of the water-absorbing resin before the addition treatment. Examples of the hydrophilic organic solvent include a primary alcohol having 1 to 4 carbon atoms, especially a primary alcohol having 2 or 3 carbon atoms, and a lower ketone having 4 or less carbon atoms such as acetone. Particularly, a volatile alcohol having a boiling point of lower than 150° C., more preferably lower than 100° C., is preferable because the volatile alcohol evaporates during a surface crosslinking treatment and no residue is left.

Specific examples thereof include a lower alcohol such as methyl alcohol, ethyl alcohol, n-propyl alcohol, isopropyl alcohol, n-butyl alcohol, isobutyl alcohol, or t-butyl alcohol; a ketone such as acetone; an ether such as dioxane, tetrahydrofuran, or methoxy (poly) ethylene glycol; an amide such as ε-caprolactam or N,N-dimethylformamide; a sulfoxide such as dimethyl sulfoxide; and a polyhydric alcohol such as polyoxypropylene or an oxyethylene-oxypropylene block copolymer.

Further, upon mixing a surface crosslinking agent solution to water-absorbing resin particles, water-insoluble fine particles or a surfactant may be present together in an amount of more than 0 part by weight and 10 parts by weight or less, preferably more than 0 part by weight and 5 parts by weight or less, and more preferably more than 0 part by weight and 1 part by weight or less per 100 parts by weight of the water-absorbing resin before the addition treatment and within a range not impairing the effect of the present invention. In this case, a surfactant used and the like is disclosed in U.S. Pat. No. 7,473,739 or the like.

The concentration of the surface crosslinking agent in the surface crosslinking agent aqueous solution is determined appropriately, and is from 1 to 80% by weight, from 5 to 60% by weight, from 10 to 40% by weight, or from 15 to 30% by weight from the viewpoint of properties. As the remnant, the hydrophilic organic solvent and other components are contained.

The temperature of the organic surface crosslinking agent aqueous solution is determined appropriately from the solubility of the organic surface crosslinking agent used, the viscosity of the aqueous solution, and the like, and is preferably from −10 to 100° C., more preferably from 5 to 70° C., still more preferably from 10 to 65° C., and particularly preferably from 25 to 50° C. A high temperature is not preferable because a cyclic compound may be hydrolyzed (for example, decomposition from ethylene carbonate to ethylene glycol or decomposition from oxazolidinone to ethanol amine), water or a hydrophilic organic solvent may evaporate to reduce a mixing property, or the like, before mixing or reaction with water-absorbing resin particles. A too low temperature is not preferable because the surface crosslinking agent solution may be solidified or a surface crosslinking agent may be precipitated.

(Combined Use of Acid or Base in Surface Crosslinking Agent Solution)

In order to accelerate a reaction or uniform mixing of a surface crosslinking agent, the surface crosslinking agent solution may contain an acid or a base in addition to the organic surface crosslinking agent, the hydrophilic organic solvent, the surfactant, and the water-insoluble fine particles. As the acid or the base, an organic acid or a salt thereof, an inorganic acid or a salt thereof, and an inorganic base are used, and are used appropriately in an amount of 0 to 10 parts by weight, preferably of 0.001 to 5 parts by weight, and more preferably of 0.01 to 3 parts by weight per 100 parts by weight of the water-absorbing resin before the addition treatment. Examples of the organic acid include a water-soluble organic acid having 1 to 6 carbon atoms, preferably 2 to 4 carbon atoms, and a water-soluble saturated organic acid, particularly a saturated organic acid having a hydroxyl group.

Other examples thereof include a non-crosslinkable water-soluble inorganic base (preferably, an alkali metal salt, an ammonium salt, an alkali metal hydroxide, and ammonia or a hydroxide thereof) and a non-reducing alkali metal salt pH buffer (preferably a hydrogen carbonate, a dihydrogen phosphate, a hydrogen phosphate, and the like).

(Method for Adding Organic Surface Crosslinking Agent Solution)

The organic surface crosslinking agent is added to water-absorbing resin particles by an addition treatment. A method for the addition treatment is not particularly limited. Examples thereof include a method for immersing a water-absorbing resin in a hydrophilic organic solvent such that the added crosslinking agent is adsorbed thereby and a method for spraying or dropwise adding the added crosslinking agent solution directly to water-absorbing resin particles and mixing. The latter method is preferable from the viewpoint of adding a predetermined amount uniformly. Furthermore, for the uniform addition, the addition treatment is preferably performed while water-absorbing resin particles are stirred, and further the organic surface crosslinking agent solution is preferably sprayed.

In the addition treatment, two or more kinds of the added crosslinking agents having different compositions may be added simultaneously, for example, by using different spraying nozzles. However, a single composition is more preferable from the viewpoint of uniformity and the like. Further, in the case of a single composition, a plurality of spraying nozzles may be used, considering the size of the addition treatment apparatus, the treatment amount thereof, the spraying angle of the spraying nozzle, or the like.

Preferable examples of an apparatus used for the addition treatment (hereinafter, also referred to as a mixing apparatus) include a cylinder type mixer, a double-wall cone type mixer, a V-shaped mixer, a ribbon type mixer, a screw type mixer, a fluidized furnace, a rotary disk mixer, an air current type mixer, a double-arm type kneader, an internal mixer, a crushing type kneader, a rotary mixer, a screw type extruder, a turbulizer, and a ploughshare mixer. In large-scale production such as commercial production, an apparatus which can perform continuous mixing is preferable. Further, each of the addition treatments may be performed using the same apparatus or different apparatuses.

The water-absorbing resin particle subjected to this step is preferably heated and kept warm. The temperature is preferably from 30 to 100° C., more preferably from 35 to 80° C., and still more preferably from 40 to 70° C. This temperature of 30° C. or higher is preferable because precipitation of a surface crosslinking agent, moisture absorption of a water-absorbing resin, or the like is suppressed, and a surface treatment is performed sufficiently and uniformly. Further, this temperature of 100° C. or lower is preferable because evaporation of water from the surface crosslinking agent aqueous solution is suppressed and a risk such as precipitation of the surface crosslinking agent is reduced.

(2-4) Surface Crosslinking Step (Particularly, (b) Surface Crosslinking Step of Granules or Surface Crosslinking Step of Foamed Polymer)

In this step, a heating treatment is conducted to perform a crosslinking treatment on the surface or the vicinity of the surface of the water-absorbing resin particles in order to improve fluid retention capacity under pressure or GCA of the water-absorbing resin particle. In this regard, an excessive surface crosslinking treatment may lower CRC too much. Therefore, it is preferable to conduct a step of performing the surface crosslinking treatment until CRC is 28 g/g or more. The surface crosslinking treatment may be performed simultaneously with or after the step for adding the surface crosslinking agent, and is preferably performed after the step for adding the surface crosslinking agent. Further, this step may be performed once, or may be performed multiple times under the same or different conditions.

(Heating Apparatus)

As the heating apparatus used in the present invention, a continuous or batch type heating apparatus including a known dryer or heating furnace equipped with a gas discharge structure and/or a gas supply structure for obtaining a predetermined atmosphere is advantageous, and a continuous heating apparatus is preferable.

As the heating methods of the heating apparatus, a conduction heat transfer type, a radiation heat transfer type, a hot air heat transfer type, and a dielectric heating type are advantageous. The conduction heat transfer and/or the hot air heat transfer type heating method are more preferable, and the conduction heat transfer type method is still more preferable.

The so-called controlled temperature of the heating apparatus is only required to be able to heat the water-absorbing resin to a temperature described below, and does not need to be constant from the beginning of the step to the end thereof. In this regard, in order to prevent partial overheating or the like, the temperature is preferably from 50 to 300° C. When damage resistance is considered important as the properties of the resulting water-absorbing agent, the temperature is more preferably 250° C. or lower, still more preferably from 70 to 200° C., and particularly preferably from 90 to 180° C. On the other hand, when absorption performance is considered important, the temperature is more preferably from 120 to 280° C., still more preferably from 150 to 250° C., and particularly preferably from 170 to 230° C.

In order to enhance the efficiency of heating and to perform a uniform heating treatment, an apparatus having a structure to stir and/or fluidize the heating object continuously is preferable. As the stirring and/or fluidizing method, a groove stirring type, a screw type, a rotary type, a disk type, a kneading type, and a fluidized tank type are preferable, and a stirring method using a stirring blade (paddle) and a stirring method due to movement of a heat transfer surface itself such as a rotary retort furnace are more preferable. In the meantime, the stirring and/or fluidizing structure aims to perform a uniform heating treatment, and therefore do not have to be used when the treated amount is small, for example, when the thickness of the drying object is less than 1 cm.

When a gas is discharged not only from a discharge outlet but also from an outlet of a product subjected to a heating treatment, the outlet of the product also corresponds to the discharge structure. Further, the amount or pressure of the discharged gas is preferably adjusted using a blower or the like. The position for discharging is not limited to one, and a plurality of positions can be provided, considering the size of the heating apparatus and the adjustment status of the dew point and the temperature.

The heating apparatus can have a gas supply structure, and control the dew point and the temperature of the atmosphere at a heating portion by adjusting the structure, for example, by adjusting the supply amount.

It is preferable that the gas pressure at the heating portion is slightly reduced from a normal pressure. As the range thereof, a differential pressure from the atmospheric pressure is preferably from 0 to −10 kPa, more preferably from 0 to −5 kPa, and still more preferably from 0 to −2 kPa.

In industrial continuous production, a batch treatment type or continuous treatment type heating apparatus having the above-described structure can be used.

When the addition treatment is performed before and after the heating treatment, the addition treatment may be performed using an apparatus the same as or different from that in the above-mentioned addition treatment. Particularly, when a continuous production apparatus is used, it may be preferable to use the same apparatus for the addition treatment before heating and the heating treatment, and to use a different apparatus for the addition treatment after heating from the viewpoint of the production efficiency.

Furthermore, the water-absorbing resin taken out from the heating apparatus, if necessary, may be cooled preferably to lower than 100° C., further 0 to 95° C., or 40 to 90° C. in order to suppress an excessive crosslinking reaction or improve handleability in a subsequent step.

(2-5) Step for Adding Additive (Particularly, (d) Step for Adding Water-Insoluble Inorganic Fine Particles)

In this step, each additive is added in order to impart various functions to the water-absorbing resin, and includes one or more steps. Examples of the additive include a moisture absorption blocking inhibitor for improving a blocking property under moisture absorption, a dust suppressing agent, a surfactant for improving flowability of powder, a coloring preventing agent, and a urine resistance improver.

Among these additives, in the production method of the present invention, water-insoluble inorganic fine particles are essentially added in order to improve the blocking property under moisture absorption. Further, addition of these additives (step (d)) may be performed simultaneously with the surface crosslinking step (step (b)) or the sizing step (step (c)). Addition of these additives (step (d)) may be performed separately from the surface crosslinking step (step (b)) or the sizing step (step (c)) (particularly after the termination of these steps).

(Moisture Absorption Blocking Inhibitor, Particularly Water-Insoluble Inorganic Particles)

A moisture absorption blocking inhibitor is a compound added in order to prevent a water-absorbing resin from forming a lump when the water-absorbing resin absorbs moisture. Among these compounds, in the production method of the present invention, water-insoluble inorganic fine particles for improving a blocking property under moisture absorption are essentially added. As long as the water-absorbing agent of the present invention essentially contains water-insoluble inorganic fine particles, a moisture absorption blocking inhibitor other than the water-insoluble inorganic fine particles may be further used together.

A water-absorbing resin easily absorbs moisture in a humid environment, and easily forms a lump. A water-absorbing resin formed into a lump lacks flowability significantly, and tends to cause a problem that a predetermined amount of water-absorbing resin cannot be supplied in the production of disposable diapers or the like. Therefore, it is necessary to add a moisture absorption blocking inhibitor to a water-absorbing resin.

Examples of the moisture absorption blocking inhibitor include a polyvalent metal salt, water-insoluble fine particles, and a surfactant. As the polyvalent metal salt, preferably a divalent or more, more preferably a trivalent or tetravalent polyvalent metal salt (organic salt or inorganic salt) or a hydroxide, i.e., a polyvalent metal cation, is exemplified. Specific examples of the polyvalent metal include aluminum, zirconium, and calcium. Specific examples of the polyvalent metal salt include aluminum lactate, aluminum sulfate, and tricalcium phosphate.

Examples of the water-insoluble fine particles include water-insoluble inorganic fine particles such as silicon oxide, aluminum oxide, aluminum hydroxide, zinc oxide, hydrotalcite, clay, or kaolin, and water-insoluble organic fine particles such as calcium lactate or metal soap (polyvalent metal salt of a long chain fatty acid). The volume average particle diameter thereof (particularly of the water-insoluble inorganic fine particle) is preferably 10 μm or less, more preferably 3 μm or less, and still more preferably 1 μm or less. On the other hand, the lower limit value of the volume average particle diameter of the water-insoluble fine particles (particularly of the water-insoluble inorganic fine particle) is preferably 0.01 μm or more.

The kind or the amount of the moisture absorption blocking inhibitor used is determined appropriately. The used amount is preferably 10% by weight or less, and 5% by weight or less, 3% by weight or less, and 1% by weight or less are preferable in this order. The lower limit is preferably 0.01% by weight or more, and more preferably 0.05% by weight or more.

(Surfactant)

By coating the surface of the water-absorbing resin of the present invention with a surfactant, a water-absorbing resin having a high water absorbent speed and a high liquid permeability can be obtained. In the meantime, as the surfactant, the compound described in (2-1) above is similarly applied.

The water-absorbing resin of the present invention is a foamed body or a granulated body, and therefore tends to have low impact resistance, and the properties thereof may be deteriorated due to damage particularly by pneumatic transportation or the like during or after the surface crosslinking. The larger the production amount is, the more significant this tendency is. For example, as the production amount per line becomes 0.5 [t/h] or more, 1 [t/h] or more, 5 [t/h] or more, and 10 [t/h] or more in order, this tendency becomes more significant.

In order to obtain a particulate water-absorbing agent having high GCA, particularly in the above continuous production at a huge scale, it is preferable to perform surface crosslinking after drying and to coat the surface of the water-absorbing resin with a surfactant simultaneously with or separately from the surface crosslinking.

The water-absorbing agent of the present invention is a foamed body or a granulated body having a large specific surface area, and therefore the bulk specific gravity thereof tends to be easily lowered. When the bulk specific gravity is small, filling in a predetermined amount becomes difficult during a filling operation for transporting the water-absorbing resin. As a result, a vibration operation or the like is necessary during the filling, and the water-absorbing resin is damaged. So, it is preferable to use a surfactant.

The kind or the amount of the surfactant used is determined appropriately. The used amount is preferably more than 0% by weight and 2% by weight or less, and more than 0% by weight and 0.03% by weight or less, more than 0% by weight and 0.015% by weight or less, more than 0% by weight and 0.01% by weight or less, and more than 0% by weight and 0.008% by weight or less are preferable in this order. The lower limit is preferably 0.1 ppm by weight or more, and 1 ppm by weight or more, 5 ppm by weight or more, and 10 ppm by weight or more are preferable in this order. Furthermore, a type of the surfactant or an amount thereof is used such that the below described surface tension (preferably 60 [mN/m] or more, more preferably within the range described in "(3-5) Surface tension" below) is maintained.

Further, from the viewpoint of the water absorbent speed or the impact resistance, water is preferably contained together with the surfactant. The water is used or contained in an amount preferably of 0.1 to 10% by weight, more preferably of 1 to 8% by weight, and still more preferably of 2 to 7% by weight per the water-absorbing resin.

(Dust Suppressing Agent)

A dust suppressing agent is a compound used in order to reduce the amount of dust generated from a water-absorbing agent. The water-absorbing resin of the present invention is a foamed body or a granulated body, and therefore tends to have low impact resistance, and may generate a dust due to damage particularly by pneumatic transportation or the like during or after surface crosslinking. Generation of a dust causes problems that the working environment is deteriorated, and that the amount of a water-absorbing agent removed from the absorbent material during the production of the absorbent material is increased and the liquid absorption time of the absorbent material is increased. Therefore, it is preferable to coat the surface of the water-absorbing resin with a dust suppressing agent.

Examples of the dust suppressing agent include polyvinyl alcohol, polyethylene oxide, polyethylene glycol, polypropylene glycol, polyacrylamide, polyacrylic acid, sodium polyacrylate, polyethylene imine, methyl cellulose, carboxymethyl cellulose, hydroxyethyl cellulose, hydroxypropyl cellulose, dextrin, sodium alginate, and starch disclosed in Patent Literature 5. Above all, polyethylene glycol is preferable.

The amount of the dust suppressing agent used is preferably 0.01 parts by weight or more, more preferably 0.05 parts by weight or more, still more preferably 0.1 parts by weight or more, and particularly preferably 0.15 parts by weight or more per 100 parts by weight of the water-absorbing resin. Further, the used amount is preferably 5.0 parts by weight or less, more preferably 4.0 parts by weight or less, still more preferably 3.0 parts by weight or less, and particularly preferably 2.5 parts by weight or less.

(Chelating Agent, α-Hydroxy Carboxylic Acid, and Inorganic or Organic Reducing Agent)

In the present invention, for the purpose of preventing coloring or deterioration, it is preferable to further incorporate a coloring preventing agent or a urine resistance (weather resistance) improver selected from a chelating agent (particularly an organic phosphorus chelating agent and an amino carboxylic acid chelating agent), α-hydroxy carboxylic acid (particularly lactic acid (salt)), and an inorganic or organic reducing agent (particularly sulfur-containing inorganic reducing agent). In the meantime, a water-absorbing resin having a large surface area tends to be easily colored or deteriorated, in general.

The amount of the coloring preventing agent or the urine resistance (weather resistance) improver such as the chelating agent used is preferably from 0 to 3 parts by weight, more preferably from 0.001 to 1 part by weight, and particularly preferably from 0.05 to 0.5 parts by weight per 100 parts by weight of the solids content of the water-absorbing resin. The coloring preventing agent or the urine resistance (weather resistance) improver is added to a monomer, a hydrogel, a dry polymer, a water-absorbing resin, or the like. Therefore, the addition step is determined appropriately on the polymerization step or later (for example, one or more periods of time selected from the group consisting of (i) during polymerization, (ii) during granulation, and (iii) after surface crosslinking). The inorganic or organic reducing agent is consumed in the polymerization step, and therefore is preferably added after the polymerization step, more preferably after the drying step, and particularly preferably after the surface crosslinking step.

Examples of the chelating agent include chelating agents disclosed in U.S. Pat. No. 6,599,989, U.S. Pat. No. 6,469,080, and EP 2163302 B, particularly a non-polymer chelating agent, and further an organic phosphorus chelating agent and an amino carboxylic acid chelating agent. Examples of the α-hydroxy carboxylic acid include malic acid (salt), succinic acid (salt), and lactic acid (salt) disclosed in US 2009/0312183 A, and the like. Examples of the inorganic or organic reducing agent include a sulfur reducing agent disclosed in US 2010/0062252 A, particularly a sulfite and a bisulfite.

Further, depending on the purpose, water, inorganic fine particles, a cationic polymer compound, a water-soluble polyvalent metal cation-containing compound, a deodorant, a perfume, an antibacterial agent, a foaming agent, a pigment, a dye, a fertilizer, an oxidizing agent, a reducing agent, or the like may be added to the water-absorbing resin in an amount of more than 0% by weight and 3% by weight or less, preferably more than 0% by weight and 1% by weight or less.

(2-6) Another Step

In the present invention, as a preferable example, (2-1) exemplifies particles having a foamed structure, and (2-2) exemplifies particles having a granulated structure. These particles may be used singly or in mixture thereof. When these particles are used in mixture thereof, the mixing ratio (weight ratio) thereof is preferably from 1:99 to 99:1, more preferably from 5:95 to 95:5, still more preferably from 10:90 to 90:10, and particularly preferably from 20:80 to 80:20. The timing for mixing these particles is not particularly limited. Examples of a preferable mixing method include a method for mixing particles having a granulated structure between a step for obtaining a foamed polymer and the surface crosslinking step, a method for mixing a foamed polymer and granules after the foamed polymer and the granules are individually surface crosslinked, and a method for mixing a foamed polymer and granules after the foamed polymer and the granules are individually added with water-insoluble inorganic fine particles. Particles having a foamed structure and particles having a granulated structure may be produced and mixed in the same production line or in different production lines. More specifically, if the production method 1 and the production method 2 are used together, when "granules obtained by granulating the water-absorbing resin having an average particle diameter of 10 to 180 μm" obtained by subjecting a water-absorbing resin obtained through the steps (a2) and (a3) of the production method 2 to the step (a1) in the production method 1 is referred to as Granule (I), "granules obtained by surface crosslinking the Granule (I)" obtained in the step (b) in the production method 1 is referred to as Granule (II), "granules obtained by sizing the Granule (II)" obtained in the step (c) in the production method 1 is referred to as Granule (III), and "an water-absorbing agent obtained by adding water-insoluble inorganic fine particles to the granule (III)" obtained in the step (d) in the production method 1 is referred to as water-absorbing agent (IV), at least one of the following <1> to <4> is included:

<1> a step for mixing the granule (I) between the (a3) polymerization step and the (b) surface crosslinking step in the production method 2;

<2> a step for mixing the granule (II) between the (b) surface crosslinking step and the (c) sizing step in the production method 1 or 2;

<3> a step for mixing the granule (III) between the (c) sizing step and the (d) adding step of the water-insoluble inorganic fine particles in the production method 1 or 2; and <4> a step for mixing the water-absorbing agent (IV) after the (d) adding step of the water-insoluble inorganic fine particles.

[3] Properties of Poly (Meth)Acrylic Acid (Salt)-Based Particulate Water-Absorbing Agent (3-1) Fluid Retention Capacity without Pressure (CRC)

The fluid retention capacity without pressure (CRC) of the particulate water-absorbing agent of the present invention is preferably 10 [g/g] or more, and controlled more preferably to 20 [g/g] or more, still more preferably to 25 [g/g] or more, still more preferably to 28 [g/g] or more, still more preferably to 30 [g/g] or more, and most preferably to 32 [g/g] or more. A higher CRC is more preferable and the upper limit value thereof is not particularly limited. From the viewpoint of a balance with other properties (particularly liquid permeability), CRC is preferably 50 [g/g] or less, more preferably 45 [g/g] or less, and still more preferably 42 [g/g] or less. CRC can be controlled by the amount of a crosslinking agent or the like. In order to achieve the range of GCA according to the present invention, it is preferable to control the fluid retention capacity without pressure (CRC) within the above range.

(3-2) Fluid Retention Capacity Under Pressure (AAP)

As described in the Examples below, the fluid retention capacity under pressure of the particulate water-absorbing agent of the present invention is specified as an fluid retention capacity relative to 0.90% by weight of aqueous sodium chloride solution under 2.06 kPa, and is controlled preferably to 25 [g/g] or more, more preferably to 28 [g/g] or more, still more preferably to 30 [g/g] or more, particularly preferably to 31 [g/g] or more, and most preferably to 32 [g/g] or more. A higher upper limit of AAP is more preferable, but the upper limit of AAP is usually preferably about 40 [g/g] from the viewpoint of a balance with other properties. If GCA is improved within the range specified in the present invention and the fluid retention capacity under pressure (AAP) can be controlled within the above range, performance of a disposable diaper can be further improved.

(3-3) Water Absorption Time (Vortex Method)

The water absorption time (Vortex method) of the particulate water-absorbing agent of the present invention is preferably 40 seconds or less, more preferably 35 seconds or less, and still more preferably 30 seconds or less. If GCA is improved within the range specified in the present invention and the water absorption time (Vortex method) can be controlled within the above range, performance of a disposable diaper can be further improved.

(3-4) Particle Size (PSD)

The particle size described in (2-1-6) above is also applied to the water-absorbing agent. By adjusting the particle size within the above range, dusting is reduced, and flowability under moisture absorption is improved, and therefore, handling is easier, GCA is improved, and the fluid retention capacity under pressure is improved.

(3-5) Surface Tension

The surface tension (specified by the measurement method in the Examples) of the particulate water-absorbing agent of the present invention is preferably 60 [mN/m] or more, more preferably 65 [mN/m] or more, still more preferably 67 [mN/m] or more, particularly preferably 70 [mN/m] or more, and most preferably 72 [mN/m] or more. The surface tension is not reduced substantially. Usually, as the upper limit, 75 [mN/m] is enough.

Conventionally, in order to improve the water absorbent speed, foaming polymerization of water-absorbing resin particles has been known. However, a large amount of surfactant (for example, from 0.1 to 10% by weight) is used for foaming as in Patent Literatures 31 and 32. Therefore, there have been problems that the surface tension of the resulting water-absorbing resin particles is lowered (particularly less than 60 [mN/m], furthermore less than 55 [mN/m]), that fine powder is generated due to excessive foaming (particularly 10% by weight or more), and that the re-wet amount of a disposable diaper is increased. In the present invention, it is particularly important to control the surface tension within the above range.

(3-6) GCA (Gel Capillary Absorption)

GCA is a parameter newly introduced in the present invention, and evaluates liquid absorption ability for 10 minutes while there is a difference in height of 10 cm between the upper surface of a glass filter and the meniscus of the lower portion of a Mariotte tube. GCA evaluates absorption ability for as short time as 10 minutes. The conventionally known fluid retention capacity under pressure (AAP) or FHA described in U.S. Pat. No. 7,108,916 evaluates absorption ability in a saturation state for one hour, and therefore is an evaluation method based on a different idea from GCA according to the present invention. A higher value of GCA of a particulate water-absorbing agent improves the ability of absorbing urea from pulp in a disposable diaper, can reduce a re-wet amount, and can suppress skin rash or urine leakage.

The value of GCA of the particulate water-absorbing agent of the present invention is calculated by the method described in the Examples below. A higher value thereof indicates better performance, and the value is preferably 28.0 g/g or more, and more preferably 30.0 g/g or more. A higher upper limit of GCA is more preferable. However, the upper limit of GCA is usually preferably about 50.0 [g/g] from the viewpoint of a balance with other properties.

In the present invention, it is particularly important that GCA is within the above range. In addition, it is preferable that the fluid retention capacity under pressure is high, and the water absorbent speed is high (i.e., the water absorption time by Vortex method is short).

(3-7) Blocking Ratio after Moisture Absorption

A blocking ratio after moisture absorption of the particulate water-absorbing agent according to the present invention is calculated by the method described in the Examples below. A lower blocking ratio after moisture absorption is more preferable, and it is preferably 20% by weight or less, more preferably 15% by weight or less, and still more preferably 10% by weight or less. The lower limit value is 0% by weight from the calculation principle. The blocking ratio after moisture absorption can be controlled to be a low value by mixing the moisture absorption blocking inhibitor described in (2-5) above in a proper amount. By controlling the blocking ratio after moisture absorption to be a low value, a particulate water-absorbing agent can be used stably in any working environment or under any use conditions of a user destination (for example, an operation condition of a production process of diapers). In the present invention, it is particularly important to control the blocking ratio after moisture absorption to be a value within the above range.

(3-8) Moisture Content

The moisture content of the particulate water-absorbing agent of the present invention is calculated by the method described in the Examples below, and is preferably from 1 to 15% by weight, more preferably from 2 to 12% by weight, and still more preferably from 3 to 10% by weight. The moisture content of 15% by weight or less is preferable because the decrease in the fluid retention capacity without pressure or the fluid retention capacity under pressure is suppressed and handleability is excellent. The moisture content of 1% by weight or more is preferable because the decrease in the fluid retention capacity under pressure due to mechanical damage caused by transportation or the like is suppressed.

[4] Absorbent Article

An application of the particulate water-absorbing agent of the present invention is not particularly limited. The particulate water-absorbing agent of the present invention is preferably used for an absorbent material used for disposable diapers or sanitary napkins.

In the present invention, an absorbent material means an absorbing agent formed by using the particulate water-absorbing agent of the present invention and a hydrophilic fiber as a main component. In the absorbent material of the present invention, the particulate water-absorbing agent content (core concentration) is preferably from 20 to 95% by weight, more preferably from 30 to 95% by weight, and particularly preferably from 35 to 90% by weight per the total weight of the particulate water-absorbing agent and the hydrophilic fiber.

When the absorbent material of the present invention is thin, the thickness of the absorbent material is preferably as thin as 0.1 to 5 mm. A thin absorbent article can be obtained by using such a thin absorbent material. For example, an absorbent article including the above-mentioned thin absorbent material of the present invention, a surface sheet having liquid permeability, and a back sheet having liquid impermeability is obtained.

A method for producing a thin absorbent article according to the present invention is as follows. An absorbent article, particularly a disposable diaper or a sanitary napkin, may be formed, for example, by forming an absorbent material (absorbent core) by blending or sandwiching a fiber substrate and a particulate water-absorbing agent, sandwiching the absorbent material with a substrate such as a surface sheet having liquid permeability and a substrate such as a back sheet having liquid impermeability, and providing an elastic member, a diffusion layer, an adhesive tape, or the like, if necessary. Such an absorbent article is compressed and shaped so as to have a density of 0.06 to 0.50 g/cc and a weight per square centimeter of 0.01 to 0.20 g/cm$^2$. Examples of the fiber substrate used include a hydrophilic fiber such as a crushed wood pulp, a cotton linter, a cross-linked cellulose fiber, rayon, cotton, wool, acetate, and vinylon. An air-laid substrate thereof is preferable.

The particulate water-absorbing agent of the present invention exhibits an excellent absorption characteristic. Therefore, specific examples of the absorbent article of the present invention include a hygienic material such as disposable diapers for adults, which are significantly growing recently, diapers for children, and sanitary napkins and a so-called incontinence pads. The leakage amount or skin rash is reduced due to the particulate water-absorbing agent of the present invention which is present in the absorbent article. Therefore, burden on a person wearing the absorbent article and nursing people can be largely reduced.

EXAMPLES

Hereinafter, the invention will be described according to the Examples, but the present invention should not be construed as being limited to the Examples. Properties described in the claims of the present invention or the Examples were determined according to the following measurement methods (a) to (k). In the meantime, unless otherwise specified, each step in each Example was performed substantially at a normal pressure (±5% of the atmospheric pressure, preferably within 1% thereof), and was performed without pressure change by intentionally increasing or reducing the pressure in the same step.

(a) Fluid Retention Capacity without Pressure (CRC) (ERT441.1-02)

The fluid retention capacity without pressure (CRC) of the particulate water-absorbing agent according to the present invention was measured in conformity with ERT441.2-02.

0.200 g (weight W0 [g]) of the particulate water-absorbing agent was weighed, uniformly put into a nonwoven fabric bag (60×85 mm), and heat-sealed. Thereafter, the bag was immersed in 500 mL of 0.90% by weight of aqueous sodium chloride solution the temperature of which was adjusted to 23±2° C. After 30 minutes, the bag was pulled up, and draining was performed using a centrifuge (centrifuge manufactured by Kokusan Co., Ltd.: type H-122) under conditions of 250 G and three minutes. Thereafter, the weight of the bag (W1 [g]) was measured.

A similar operation was performed without adding a particulate water-absorbing agent, and the weight of the bag (W2 [g]) at this time was measured. The fluid retention capacity without pressure (CRC) was calculated according to the following (formula 1) from W0 [g], W1 [g], and W2 [g] obtained.

$$CRC\ (g/g) = \{(W1-W2)/W0\} - 1 \quad \text{(formula 1)}$$

(b) Fluid Retention Capacity Under Pressure (AAP) (ERT442.2-02)

The fluid retention capacity under pressure (AAP) of the particulate water-absorbing agent according to the present invention was measured in conformity with ERT442.2-02.

0.900 g (weight W3 [g]) of the particulate water-absorbing agent was put into a measurement apparatus, and the weight of the whole measurement apparatus (weight W4 [g]) was measured. As a next step, 0.90% by weight of aqueous sodium chloride solution, a temperature of which was adjusted to 23±2° C., was absorbed under a load of 2.06 kPa (0.3 psi, 21 g/cm$^2$). After one hour, the weight of the whole measurement apparatus (weight W5 [g]) was measured, and the fluid retention capacity under pressure (AAP) was calculated according to the following (formula 2) based upon the obtained W3 [g], W4 [g], and W5 [g].

$$AAP\ (g/g) = (W5-W4)/W3 \quad \text{(formula 2)}$$

(c) Water Absorption Time (Vortex Method)

0.02 parts by weight of Food Blue No. 1, which is a food additive, was added to 1000 parts by weight of 0.90% by weight of aqueous sodium chloride solution prepared in advance, and the liquid temperature was adjusted to 30° C. 50 ml of 0.90% by weight of aqueous sodium chloride solution colored in blue was measured and was put into a 100 ml beaker. 2.00 g of the particulate water-absorbing agent was put thereinto while the aqueous sodium chloride solution was stirred at 600 rpm with a cylindrical stirrer having a length of 40 mm and a thickness of 8 mm. The water absorption time (second) was measured. The end point was in conformity with a standard described in JIS K 7224-1996 fiscal year "Testing method for water absorbent speed of water-absorbing resins". A period of time until the water-absorbing agent absorbs the physiological saline solution and the test liquid covers the stirrer chip was measured as the water absorption time (second).

(d) Particle Size (PSD, σζ)

The particle size (PSD) and the logarithmic standard deviation (σζ) in the particle size distribution of the particulate water-absorbing agent according to the present invention were measured in conformity with the measurement method disclosed in US 2006/204755 A.

That is, 10.00 g of the particulate water-absorbing agent was classified using a JIS standard sieve (The IIDA TESTING SIEVE: inner diameter 80 mm; JIS Z 8801-1 (2000)) having an opening of 850 μm, 710 μm, 600 μm, 500 μm, 425 μm, 300 μm, 212 μm, 150 μm, 106 μm, or 75 μm or a sieve corresponding to the JIS standard sieve. After the classification, the weight of each sieve was measured, and the weight percent (% by weight) of particles having a particle diameter of less than 150 μm was calculated. In the meantime, the term "weight percent of particles having a particle diameter of less than 150 μm" refers to the weight ratio (%) of particles passing through a JIS standard sieve having an opening of 150 μm per the whole water-absorbing agent.

Further, the residual percentage R of each particle size was plotted on a logarithmic probability paper and the particle diameter corresponding to R=50% by weight was read as the weight average particle diameter (D50) from this graph. The weight average particle diameter (D50) means a particle diameter corresponding to 50% by weight of the whole particulate water-absorbing agent. Further, the logarithmic standard deviation (σζ) in the particle size distribution is represented by the following (formula 3). A smaller σζ value means a narrower particle size distribution.

$$\sigma\zeta = 0.5 \times \ln(X2/X1)\ (X1 \text{ represents the particle diameter at } R=84.1\%, \text{ and } X2 \text{ represents the particle diameter at } R=15.9\%) \quad \text{(formula 3)}$$

(e) Surface Tension 50 ml of 0.90% by weight of aqueous sodium chloride solution, a temperature of which was adjusted to 20° C., was put into a 100 ml beaker sufficiently washed. First, the surface tension of 0.90% by weight of aqueous sodium chloride solution was measured using a surface tension meter (K11 automatic surface tension meter manufactured by KRUSS GmbH). In this measurement, the surface tension must be within the range of 71 to 75 [mN/m]. Subsequently, a sufficiently washed cylindrical stirrer having a length of 25 mm and 0.500 g of a particulate water-absorbing agent were put into a beaker containing 0.90% by weight of aqueous sodium chloride solution after the measurement of the surface tension, the temperature of which was adjusted to 20° C. The resulting mixture was stirred at 500 rpm for four minutes. After the four minutes, stirring was stopped. After the water-containing particulate water-absorbing agent was precipitated, a similar operation was performed again, and the surface tension of the supernatant was measured. The present invention employs a plate method using a platinum plate. The plate was sufficiently washed with deionized water and was heated and washed with a gas burner before each measurement, and used.

(f) Blocking Ratio after Moisture Absorption (Also Known as Caking Ratio in High Humidity)

About 2 g of a particulate water-absorbing agent was uniformly scattered in an aluminum cup having a diameter of 52 mm, and then was left for one hour at a constant temperature and constant humidity chamber (manufactured by Espec Co., Ltd.; MODEL: SH-641), a temperature of which was adjusted to 25° C., and the relative humidity of which was adjusted to 90±5% RH.

Thereafter, the particulate water-absorbing agent in the aluminum cup was transferred gently onto a JIS standard sieve (The IIDA TESTING SIEVE/inner diameter 80 mm) having an opening of 2000 μm (8.6 mesh). Then, classification was performed for eight seconds at a temperature of 20 to 25° C. at a relative humidity of 50% RH using a low tap sieve shaker (manufactured by Sieve Factory Iida Co., Ltd.; ES-65 sieve shaker/rotation speed 230 rpm, impact number 130 rpm).

Subsequently, the weight of the particulate water-absorbing agent remaining on the JIS standard sieve (W6 [g]) and the weight of the particulate water-absorbing agent which had passed through the JIS standard sieve (W7 [g]) were measured, and moisture absorption flowability (blocking ratio after moisture absorption) was calculated according to the following (formula 4). A lower blocking ratio after moisture absorption exhibits better flowability under moisture absorption.

$$\text{blocking ratio after moisture absorption (\%)} = \{W6/(W6+W7)\} \times 100 \quad \text{(formula 4)}$$

(g) Solid Content and Moisture Content

About 1 g (weight W9 [g]) of a water-absorbing resin (water-absorbing agent) was measured and put into an aluminum cup (weight W8 [g]) having a diameter of the bottom surface of about 5 cm, and was left for three hours in a dryer without wind at 180° C. and then dried. The total weight (W10 [g]) of the aluminum cup and the water-absorbing resin (water-absorbing agent) after drying was measured, and the solids content was determined by the following (formula 5). Further, the moisture content is determined by the following (formula 6).

$$\text{solids content [\% by weight]} = \{(W10-W8)/W9\} \times 100 \quad \text{(formula 5)}$$

$$\text{moisture content [\% by weight]} = 100 - \text{solids content [\% by weight]} \quad \text{(formula 6)}$$

(h) GCA (Gel Capillary Absorption)

Figure 11:
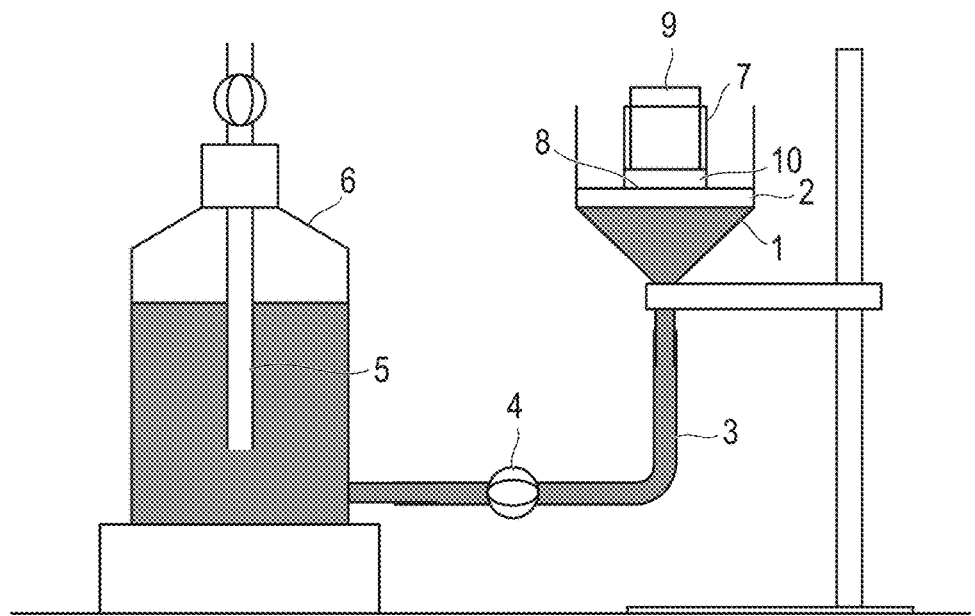
FIG. 11 is a schematic diagram of an apparatus used for GCA measurement of the present invention.

An apparatus and a method for measuring GCA will be described with reference to FIG. 11. A glass filter 2 used in this measurement method is a 500 ml glass filtration apparatus as specified by ISO 4793 (1980), has a pore diameter of P40 (16 to 40 μm) and a thickness of 7 mm, and is, for example, a Duran grade 3 glass filtration apparatus manufactured by Schott Inc. Further, the filter having a radius of 30 cm must have a water flowing ability of 50 ml/min at 20° C. at a pressure difference of 50 mbar. A silicone tube 3 is connected to the lower part of the filtration apparatus 1 with the glass filter, and is further connected to the lower part of a tank 6 provided with a glass tube 5 and a stop cock 4. At this time, the upper surface of the glass filter is fixed at a position 10 cm higher than the meniscus of the lower part of the glass tube in the tank. The system is filled with 0.90% by weight of aqueous sodium chloride solution. A high humidity strength cellulose tissue 8 cut into a 8 cm square is fixed to the bottom of a plastic support cylinder 7 having an inner diameter of 60 mm with a metal ring. The tissue has a maximum basis weight of 24.6 g/m² and a minimum humidity tensile strength of 0.32 N/cm (CD direction) and 0.8 N/cm (MD direction) (The flowing direction when paper is produced by a paper machine is referred to as MD direction, and a direction perpendicular thereto is referred to as CD direction), and is available from Fripa Inc. in Germany, for example. 0.2 g (weight W11 [g]) of the particulate water-absorbing agent 10 was scattered uniformly on the tissue at a room temperature (20 to 25° C.) at a humidity of 50% RH. A piston 9 adjusted so as to apply a load of 0.39 kPa (0.05 psi) to the water-absorbing agent, having an outer diameter of slightly less than 60 mm, not causing a gap with the support cylinder, and capable of moving vertically without being hindered, was put on the particulate water-absorbing agent. The weight of the whole measurement apparatus (W12 [g]) was measured.

The whole measurement apparatus was put on a glass filter. A valve of the fluid tank with a Mariotte tube was opened for absorption for ten minutes. Thereafter, the whole measurement apparatus was pulled up, and the weight thereof (W13 [g]) was measured. GCA (g/g) was calculated according to the following (formula 7) from W11, W12, and W13.

$$\text{GCA (g/g)} = (W13-W12)/W11 \quad \text{(formula 7)}$$

(i) Method for Evaluating Absorbent Material

In order to evaluate the performance of the water-absorbing agent according to the present invention as an absorbent material, the following absorbent material (the concentration of the water-absorbing agent: 40% by weight) was produced. The liquid absorption time (first time, second time, and third time) and the re-wet amount (first time, second time, and third time) were measured and evaluated as a micturition model thereof in multiple stages.

A pulp sheet of 12 cm×38 cm was produced in advance using 8.5 g of crushed wood pulp. 11.3 g of the particulate water-absorbing agent obtained in the present Example was sprayed uniformly on the pulp sheet. A pulp sheet having the same size and the same weight was put thereon, and a pressure of 3.8 kg/cm² was applied thereto for one minute. An absorption sheet having a size of 12 cm×38 cm and 5.5 mm in thickness was thereby produced. Subsequently, the absorption sheet was extended in a planar shape, and a resin cylinder (outer diameter: 100 mm, inner diameter: 25 mm, height: 220 mm, weight: 3.6 kg, inner volume: 108 cm³) was put in the center of the sheet.

In the first time of liquid injection, 100 g of 0.90% by weight of aqueous sodium chloride solution was poured into the resin cylinder at 7 ml/s. A period of time required for the aqueous sodium chloride solution to be absorbed completely by an absorbent article was used as the first liquid absorption time. Ten minute after the addition of the liquid, the resin cylinder was removed. 10 g (weight W14 [g]) of a filter paper (Advantec Toyo Kaisha, Ltd., product name: (JIS P 3801, No. 2), thickness: 0.26 mm, pore size: 5 μm, diameter: 90 mm) was disposed on the center, and 2.5 kg of a cylindrical weight (diameter: 8 cm) was placed on the upper surface of the filter paper. After two minutes, the cylindrical weight was removed. The weight of the filter paper W15 [g] was measured, and the first re-wet amount was determined according to the following (formula 8).

$$\text{re-wet amount (g)} = W15-W14 \quad \text{(formula 8)}$$

In the second time of liquid injection, the same procedure to the first time of liquid injection was performed except that 50 g of 0.90% by weight of aqueous sodium chloride solution was used and 20 g of the filter paper was used. The second liquid absorption time and the second re-wet amount were measured.

In the third time of liquid injection, the same procedure to the first time of liquid injection was performed except that 50 g of 0.90% by weight of aqueous sodium chloride solution was used and 30 g of the filter paper was used. The third liquid absorption time and the third re-wet amount were measured.

Total Explanation of Examples

Production Example 1 is a production example of a water-absorbing resin in the form other than a foamed polymer (the results are indicated in Table 1).

Production Examples 2 and 3 are production examples of a water-absorbing resin in the form of a foamed polymer (the results are indicated in Tables 1 and 2).

Production Examples 4 and 5 are production examples of a water-absorbing resin in a granulated form (the results are indicated in Table 1).

Examples 1 to 6 are examples of a water-absorbing agent by the production method 1 using a water-absorbing resin in the form of granules.

Examples 7 to 12 are examples of a water-absorbing agent by the production method 2 using a water-absorbing resin in the form of a foamed polymer.

Comparative Examples 1 to 6 are comparative examples of a water-absorbing agent by a production method not using a water-absorbing resin in the form of a foamed polymer or in the form of granules.

Comparative Examples 7 and 11 are comparative examples of a water-absorbing agent described in Examples of Patent Literatures.

Comparative Examples 8 and 9 are comparative examples of a water-absorbing agent in which a surfactant was further added in the Comparative Example 7.

Comparative Example 10 is a comparative example of a water-absorbing agent by a production method not using water-insoluble inorganic fine particles.

Experimental Results and Tables

Hereinafter, the results of Production Examples 1 to 3, Examples 1 to 12, and Comparative Examples 1 to 11 will be indicated in the following Tables 1 to 4. Table 1 indicates the particle size (particle size distribution, D50) and properties (CRC, moisture content) of the water-absorbing resin particles obtained in Production Examples 1 to 5, which are raw materials of a water-absorbing agent. Tables 2 and 3 indicate the particle sizes and properties of the water-absorbing agents and the comparative water-absorbing agents. Table 4 indicates the evaluation results of the absorbent articles containing a water-absorbing agent or a comparative water-absorbing agent.

(Production Example of Water-Absorbing Resin)

(Production Example 1) Production Example of Water-Absorbing Resin in the Form Other than Foamed Polymer By dissolving 4.4 parts by weight of polyethylene glycol diacrylate (n=9) in 5500 parts by weight of 38% by weight of aqueous sodium acrylate (rate of neutralization: 75 mol %) solution, an aqueous monomer solution was obtained. Subsequently, the reaction liquid was degassed for 30 minutes under a nitrogen gas atmosphere. Subsequently, this reaction liquid was supplied to a jacketed stainless steel twin-arm kneader with an openable lid and two sigma type blades, and the system was replaced with nitrogen gas while the reaction liquid was kept at 30° C. Subsequently, while the reaction liquid was stirred, 2.8 parts by weight of sodium persulfate and 0.12 parts by weight of L-ascorbic acid were added. After about 1 minute, polymerization was initiated. Polymerization was performed at 30 to 90° C., and a hydrogel-forming crosslinked polymer was taken out 60 minutes after the initiation of the polymerization.

The resulting hydrogel-forming crosslinked polymer was fragmented so as to have a diameter of about 5 mm. This fragmented hydrogel-forming crosslinked polymer was spread on a wire mesh of 50 mesh, and was dried with hot air at 160° C. for 60 minutes. Subsequently, the dried product was crushed using a roll mill (manufactured by Inokuchi Giken Limited Company, WML type roll crusher) to obtain water-absorbing resin particles (A). By further classifying the water-absorbing resin particles (A) with a wire mesh having an opening of 850 μm and a wire mesh of 180 μm, water-absorbing resin particles (A1) as a fraction which had passed through the wire mesh of 850 μm but had not passed through the wire mesh of 180 μm and water-absorbing resin fine particles (A2) as a fraction which had passed through the wire mesh of 180 μm were obtained. At this time, the ratio of particles having a particle diameter of less than 150 μm in the water-absorbing resin particles (A) was 10.5% by weight. The ratio of particles having a particle diameter of less than 150 μm in the water-absorbing resin particles (A1) obtained by the classification could be reduced to 1.9% by weight. CRC, moisture content, particle size distribution, and D50 of the resulting water-absorbing resin particles (A1) and the water-absorbing resin fine particles (A2) are indicated in Table 1.

(Production Example 2) Production Example (1) of Water-Absorbing Resin in the Form of Foamed Polymer Into a 2 liter polypropylene container, 422.0 g of acrylic acid, 1.38 g of polyethylene glycol diacrylate (molecular weight 523) as an internal crosslinking agent, 5.68 g of 2% by weight of aqueous trisodium diethylenetriamine pentaacetate solution, 173.9 g of 48.5% by weight of aqueous sodium hydroxide solution, 4.39 g of 1.0% by weight of aqueous polyoxyethylene (20) sorbitan monostearate (manufactured by Kao Corporation) solution as a surfactant, and 401.27 g of deionized water (ion-exchanged water) were added and dissolved (mixed) to prepare an aqueous monomer solution (1'). The temperature of the aqueous monomer solution (1') rose to 65° C. due to neutralization heat in the first stage immediately after preparation. Since the solubility of a gas was lowered due to the rise in the temperature, the appearance of the aqueous monomer solution (1') containing the surfactant was cloudy due to the introduction of very fine bubbles.

Subsequently, the aqueous monomer solution (1') was cooled while being stirred. When the liquid temperature became 53° C., 178.7 g of 48.5% by weight of aqueous sodium hydroxide solution the temperature of which had been adjusted to 30° C. was added thereto and mixed therewith to prepare an aqueous monomer solution (1). At this time, the temperature of the aqueous monomer solution (1) rose to 83.5° C. due to neutralization heat in the second stage immediately after preparation. Since the solubility of a gas was lowered due to the rise in the temperature, the appearance of the aqueous monomer solution (1) containing the surfactant was cloudy due to the introduction of very fine bubbles.

Subsequently, within one minute after the addition of the aqueous sodium hydroxide solution in the second stage, 17.6 g of 4.0% by weight of aqueous sodium persulfate solution was added to the aqueous monomer solution (1) while the monomer solution was stirred. Immediately thereafter, the resulting mixture was poured into a stainless steel tray type container (bottom surface: 340×340 mm, height: 25 mm, inner surface: Teflon (registered trademark) was stuck) in an atmosphere open system. In the meantime, the tray type container was heated using a hot plate (manufactured Iuchi Seieido Co.; NEO HOTPLATE HI-1000), and was adjusted such that the surface temperature was 40° C. 25 seconds after the aqueous monomer solution (1) was poured into the tray type container, a polymerization reaction was initiated. The polymerization reaction proceeded while generating water vapor and expanding and foaming vertically and horizontally, and then was contracted to a size slightly larger than the tray type container. The expansion and contraction were terminated within about one minute. Three minutes after the initiation of the polymerization reaction, a hydrogel-forming crosslinked polymer (hydrogel) was taken out. These series of operations were performed in an atmosphere open system, and the peak temperature during the polymerization was 108° C.

The hydrogel-forming crosslinked polymer (hydrogel) obtained by the polymerization reaction was subjected to gel-crushing using a meat chopper (manufactured by Iizuka Corporation, MEAT-CHOPPER TYPE: 12VR-400KSOX, die hole diameter: 7.5 mm, the number of hole: 38, thickness of die: 8 mm) to obtain a fragmented hydrogel-forming crosslinked polymer. At this time, the addition amount of the hydrogel was 450 [g/min]. The gel-crushing was performed while deionized water the temperature of which had been adjusted to 90° C. was added at 50 [g/min] in parallel with the addition of the hydrogel.

The fragmented hydrogel-forming crosslinked polymer obtained by the gel-crushing operation was spread on a stainless steel wire mesh having an opening of 850 μm, and was dried with hot air at 190° C. for 30 minutes. Subsequently, the dried product obtained by the drying operation was crushed using a roll mill to obtain water-absorbing resin particles (B). By further classifying the water-absorbing resin particles (B) with a wire mesh having an opening of 850 μm and a wire mesh of 150 μm, foamed water-absorbing resin particles (B1) as a fraction which had passed through the wire mesh of 850 μm but had not passed through the wire mesh of 150 μm and water-absorbing resin fine particles (B2) as a fraction which had passed through the wire mesh of 150 μm were obtained. At this time, the ratio of particles having a particle diameter of less than 150 μm in the water-absorbing resin particles (B) was 12.4% by weight. The ratio of particles having a particle diameter of less than 150 μm in the water-absorbing resin particles (B1) obtained by the classification could be reduced to 1.9% by weight. By observing a particle of the water-absorbing resin particles (B1) using SEM, it was confirmed that a large number of crater-like depressions derived from the bubbles were present and therefore a foamed shape was formed effectively. On the other hand, in the water-absorbing resin fine particles (B2), presence of the crater-like depressions derived from the bubbles was clearly confirmed although the number thereof was reduced since the particle shape was fine. CRC, moisture content, particle size distribution, and D50 of the resulting water-absorbing resin particles (B1) and the water-absorbing resin fine particles (B2) are indicated in Table 1.

(Production Example 3) Production Example (2) of Water-Absorbing Resin in the Form of Foamed Polymer The same reaction and operation as the Production Example 2 was performed except that the amount of polyethylene glycol diacrylate was changed from 1.38 g to 0.67 g in the Production Example 2 to obtain water-absorbing resin particles (C) corresponding to the water-absorbing resin particles (B). Furthermore, from the water-absorbing resin particles (C), foamed water-absorbing resin particles (C1) as a fraction which had passed through the wire mesh of 850 μm but had not passed through the wire mesh of 150 μm and water-absorbing resin fine particles (C2) as a fraction which had passed through the wire mesh of 150 μm were obtained. At this time, the ratio of particles having a particle diameter of less than 150 μm in the water-absorbing resin particles (C) was 11.5% by weight. The ratio of particles having a particle diameter of less than 150 μm in the water-absorbing resin particles (C1) obtained by the classification could be reduced to 1.4% by weight. By observing a particle of the water-absorbing resin particles (C1) using SEM, it was confirmed that a large number of crater-like depressions derived from the bubbles were present and therefore a foamed shape was formed effectively. On the other hand, in the water-absorbing resin fine particles (C2), presence of the crater-like depressions derived from the bubbles was clearly confirmed although the number thereof was reduced since the particle shape was fine. CRC, moisture content, particle size distribution, and D50 of the resulting water-absorbing resin particles (C1) and the water-absorbing resin fine particles (C2) are indicated in Table 1.

(Production Example 4) Production Example (1) of Water-Absorbing Resin in the Form of Granules 300 g of the water-absorbing resin fine particles (A2) obtained in the Production Example 1 was put into a 5 L mortar mixer manufactured by Nishinihon Shikenki Co., Ltd. (the 5 L container was kept warm in a bath at 80° C.). 300 g of deionized water heated to 90° C. was added thereto at once while a stirring blade of the mortar mixer was rotated at a high speed of 60 Hz/100 V.

The water-absorbing resin fine particles (A2) and the deionized water were mixed within 10 seconds, and the whole content became hydrogel-forming granules having a particle diameter of about 3 to 10 mm. In the mortar mixer, the hydrogel-forming granules were in a separated state, and there was no sign that the hydrogel-forming granules would be kneaded by the mixing of the stirring blade. Stirring at a high speed was performed in the mortar mixer for one minute. Thereafter, the resulting hydrogel-forming granules in a separated state were spread on a wire mesh of 50 mesh, and were dried with hot air at 150° C. for 60 minutes. Subsequently, the dried granules were crushed using a roll mill to obtain water-absorbing resin granules (A3'). By further classifying the water-absorbing resin granules (A3') with a wire mesh having an opening of 850 μm and a wire mesh of 150 μm, water-absorbing resin granules (A3) as a fraction which had passed through the wire mesh of 850 μm but had not passed through the wire mesh of 150 μm was obtained. At this time, the ratio of particles having a particle diameter of less than 150 μm in the water-absorbing resin granules (A3') was 21.8% by weight. The ratio of particles having a particle diameter of less than 150 μm in the water-absorbing resin granules (A3) obtained by the classification could be reduced to 2.0% by weight. By observing the shape of the water-absorbing resin granules (A3) using SEM, it was found that the water-absorbing resin fine particles used as a raw material was granulated into a large particle while the shape thereof was maintained partially and that the particle had a large surface area with many irregularities on the surface of the particles. CRC, moisture content, particle size distribution, and D50 of the resulting water-absorbing resin granules (A3) are indicated in Table 1.

(Production Example 5) Production Example (2) of Water-Absorbing Resin in the Form of Granules 300 g of the water-absorbing resin fine particles (B2) obtained in the Production Example 2 was put into a 5 L mortar mixer manufactured by Nishinihon Shikenki Co., Ltd. (the 5 L container was kept warm in a bath at 80° C.). 300 g of deionized water heated to 90° C. was added thereto at once while a stirring blade of the mortar mixer was rotated at a high speed of 60 Hz/100 V.

The water-absorbing resin fine particles (B2) and the deionized water were mixed within 10 seconds, and the whole content became hydrogel-forming granules having a particle diameter of about 3 to 10 mm. In the mortar mixer, the hydrogel-forming granules were in a separated state, and there was no sign that the hydrogel-forming granules would be kneaded by the mixing of the stirring blade. Stirring at a high speed was performed in the mortar mixer for one minute. Thereafter, the resulting hydrogel-forming granules in a separated state were spread on a wire mesh of 50 mesh, and were dried with hot air at 150° C. for 60 minutes. Subsequently, the dried granules were crushed using a roll mill to obtain water-absorbing resin granules (B3'). By further classifying the water-absorbing resin granules (B3') with a wire mesh having an opening of 850 μm and a wire mesh of 150 μm, water-absorbing resin granules (B3) as a fraction which had passed through the wire mesh of 850 μm but had not passed through the wire mesh of 150 μm was obtained. At this time, the ratio of particles having a particle diameter of less than 150 μm in the water-absorbing resin particles (B3') was 11.4% by weight. The ratio of particles having a particle diameter of less than 150 μm in the water-absorbing resin granules (B3) obtained by the classification could be reduced to 2.4% by weight. CRC, moisture content, particle size distribution, and D50 of the resulting water-absorbing resin granules (B3) are indicated in Table 1.

(Example 1) Water-Absorbing Agent by Production Method 1 Using Water-Absorbing Resin in the Form of Granules To 100 parts by weight of the water-absorbing resin granules (A3) obtained in the Production Example 4, a surface crosslinking agent solution including 0.025 parts by weight of ethylene glycol diglycidyl ether, 0.3 parts by weight of ethylene carbonate, 0.5 parts by weight of propylene glycol, and 2.0 parts by weight of deionized water was mixed. The above mixture was heated at 200° C. for 35 minutes to obtain surface crosslinked water-absorbing resin granules (A4).

The surface crosslinked water-absorbing resin granules (A4) were swelled with 0.90% by weight of aqueous sodium chloride solution and were observed with an optical microscope. At this time, it was confirmed that, as a result of surface crosslinking, the shape of the particles could be maintained even after water absorption.

To 100 parts by weight of the surface crosslinked water-absorbing resin granules (A4), one part by weight of 1% by weight of aqueous DTPA solution was added while being stirred, and was mixed therewith for one minute. Subsequently, the resulting mixture was left in a hot air dryer at 60° C. for 30 minutes, and then was made to pass through a wire mesh having an opening of 850 μm to obtain water-absorbing resin granules (A4'). Further, to 100 parts by weight of the resulting water-absorbing resin granules (A4'), 0.3 parts by weight of hydrotalcite (product name: DHT-6 manufactured by Kyowa Chemical Industry Co., Ltd.) was mixed. Mixing was performed by putting 30 g of the water-absorbing resin and the hydrotalcite into a mayonnaise jar of 225 ml volume and vibrating the jar using a paint shaker (No. 488/manufactured by Toyo Seiki Seisaku-Sho, Ltd.) at 800 cycle/min (CPM) for three minutes to obtain a particulate water-absorbing agent (EX-1).

Example 2

The same reaction and operation as the Example 1 except that 0.3 parts by weight of the hydrotalcite was changed to 0.3 parts by weight of Aerosil 200 (manufactured by NIPPON AEROSIL Co., Ltd.) in the Example 1 to obtain a particulate water-absorbing agent (EX-2).

Example 3

To 100 parts by weight of the water-absorbing resin granules (A4') obtained in the Example 1, a mixed solution of 3.3 parts by weight of colloidal silica (manufactured by AZ Electronic Materials Co., Klebsol 30B12) and 1.0 part by weight of propylene glycol was added uniformly and mixed while being stirred. The resulting mixture was left in a hot air dryer at 60° C. for 60 minutes, and then was made to pass through a wire mesh having an opening of 850 μm to obtain a particulate water-absorbing agent (EX-3).

Examples 4 to 6

The same reaction and operation as the Example 1 except that 0.3 parts by weight of the hydrotalcite was changed to 0.3 parts by weight of the following water-insoluble inorganic fine particles in the Example 1, particulate water-absorbing agents (EX-4) to (EX-6) were obtained.
Changed to 0.3 parts by weight of zinc oxide (manufactured by ALDRICH, Co.) (Example 4)
Changed to 0.3 parts by weight of tricalcium phosphate (manufactured by Wako Pure Chemical Industries, Ltd.) (Example 5)
Changed to 0.3 parts by weight of aluminum hydroxide (manufactured by Nippon Light Metal Company, Ltd., particle diameter 1.6 μm) (Example 6)

(Example 7) Water-Absorbing Agent by Production Method 2 Using Water-Absorbing Resin in the Form of Foamed Polymer To 100 parts by weight of the water-absorbing resin particles (B1) obtained in the Production Example 2, a surface crosslinking agent solution including 0.025 parts by weight of ethylene glycol diglycidyl ether, 0.3 parts by weight of ethylene carbonate, 0.5 parts by weight of propylene glycol, and 2.0 parts by weight of water was mixed.

The above mixture was heated at 200° C. for 35 minutes to obtain surface crosslinked water-absorbing resin particles (B5).

To 100 parts by weight of the surface crosslinked water-absorbing resin particles (B5), one part by weight of 1% by weight of aqueous DTPA solution was added while being stirred, and was mixed therewith for one minute. Subsequently, the resulting mixture was left in a hot air dryer at 60° C. for 30 minutes, and then was made to pass through a wire mesh having an opening of 850 μm to obtain water-absorbing resin particles (B5'). Further, to 100 parts by weight of the resulting water-absorbing resin particles (B5'), 0.3 parts by weight of hydrotalcite (product name: DHT-6 manufactured by Kyowa Chemical Industry Co., Ltd.) was mixed. Mixing was performed by putting 30 g of the water-absorbing resin and the hydrotalcite into a mayonnaise jar of 225 ml volume and vibrating the jar using a paint shaker (No. 488/manufactured by Toyo Seiki Seisaku-Sho, Ltd.) at 800 cycle/min (CPM) for three minutes to obtain a particulate water-absorbing agent (EX-7). The internal cell rate of the resulting particulate water-absorbing agent (EX-7) was 3.1%.

(Example 8) Water-Absorbing Agent by Production Method 1 and 2 Using Granules of Water-Absorbing Resin in the Form of Foamed Polymer To 100 parts by weight of the water-absorbing resin granule (B3), a surface crosslinking agent solution including 0.025 parts by weight of ethylene glycol diglycidyl ether, 0.3 parts by weight of ethylene carbonate, 0.5 parts by weight of propylene glycol, and 2.0 parts by weight of deionized water was mixed. The above mixture was heated at 200° C. for 35 minutes to obtain surface crosslinked water-absorbing resin granules (B4). 50 parts by weight of the surface crosslinked water-absorbing resin granules (B4) and 50 parts by weight of the surface crosslinked water-absorbing resin particles (B5) obtained in the Example 7 were mixed to obtain a water-absorbing resin (E1).

To 100 parts by weight of the water-absorbing resin (E1), one part by weight of 1% by weight of aqueous DTPA solution was added while being stirred, and was mixed therewith for one minute. Subsequently, the resulting mixture was left in a hot air dryer at 60° C. for 30 minutes, and then was made to pass through a wire mesh having an opening of 850 μm to obtain a water-absorbing resin (E1'). Further, to 100 parts by weight of the resulting water-absorbing resin (E1'), 0.3 parts by weight of hydrotalcite (product name: DHT-6 manufactured by Kyowa Chemical Industry Co., Ltd.) was mixed. Mixing was performed by putting 30 g of the water-absorbing resin and the hydrotalcite into a mayonnaise jar of 225 ml volume and vibrating the jar using a paint shaker for three minutes to obtain a particulate water-absorbing agent (EX-8).

(Example 9) Water-Absorbing Agents by Production Methods 1 and 2 Using Granules in Different Production Lines with Foamed Polymer of Water-Absorbing Resin 50 parts by weight of the water-absorbing resin granules (A3) obtained in the Production Example 4 and 50 parts by weight of the water-absorbing resin particles (B1) obtained in the Production Example 2 were mixed to obtain water-absorbing resin particles (E2).

The same reaction and operation as the Example 7 except that the water-absorbing resin particles (B1) were changed to the water-absorbing resin particles (E2) in the Example 7, a particulate water-absorbing agent (EX-9) was obtained.

(Example 10) Water-Absorbing Agent by Production Methods 1 and 2 Using Granules in the Same Production Line with Foamed Polymer of Water-Absorbing Resin 50 parts by weight of the water-absorbing resin granules (B3) obtained in the Production Example 5 and 50 parts by weight of the water-absorbing resin particles (B1) obtained in the Production Example 2 were mixed to obtain water-absorbing resin particles (E3).

The same reaction and operation as the Example 7 except that the water-absorbing resin particles (B1) were changed to the water-absorbing resin particles (E3) in the Example 7, a particulate water-absorbing agent (EX-10) was obtained.

(Example 11) Water-Absorbing Agent by Production Method 2 Using Water-Absorbing Resin in the Form of Foamed Polymer To 100 parts by weight of the water-absorbing resin particles (C1) obtained in the Production Example 3, a surface crosslinking agent solution including 0.03 parts by weight of ethylene glycol diglycidyl ether, 1.5 parts by weight of propylene glycol, and 3.5 parts by weight of water was mixed. The above mixture was heated at 100° C. for 45 minutes to obtain surface crosslinked water-absorbing resin particles (C3).

Further, to 100 parts by weight of the surface crosslinked water-absorbing resin particles (C3), one part by weight of 1% by weight of aqueous DTPA solution was added while being stirred, and was mixed therewith for one minute. Subsequently, the resulting mixture was left in a hot air dryer at 60° C. for 30 minutes, and then was made to pass through a wire mesh having an opening of 850 μm to obtain water-absorbing resin particles (C3'). Further, to 100 parts by weight of the resulting water-absorbing resin particles (C3'), 0.3 parts by weight of hydrotalcite (product name: DHT-6 manufactured by Kyowa Chemical Industry Co., Ltd.) was mixed. Mixing was performed by putting 30 g of the water-absorbing resin and the hydrotalcite into a mayonnaise jar of 225 ml volume and vibrating the jar using a paint shaker (No. 488/manufactured by Toyo Seiki Seisaku-Sho, Ltd.) at 800 cycle/min (CPM) for three minutes to obtain a particulate water-absorbing agent (EX-11).

Example 12

The same reaction and operation as the Example 11 except that the amount of ethylene glycol diglycidyl ether was changed from 0.03 parts by weight to 0.015 parts by weight in the Example 11, a particulate water-absorbing agent (EX-12) was obtained.

(Comparative Example 1) Comparative Water-Absorbing Agent by Production Method not Using Foamed Polymer or Granules The same reaction and operation as the Example 7 except that the water-absorbing resin particles (B1) in the form of a foamed polymer was changed to the water-absorbing resin particles (A1) in the Example 7 to obtain a comparative particulate water-absorbing agent (COMP-1) containing 0.3 parts by weight of hydrotalcite.

Comparative Example 2

The same reaction and operation as the Comparative Example 1 except that 0.3 parts by weight of the hydrotalcite was changed to 0.3 parts by weight of Aerosil 200 (manufactured by NIPPON AEROSIL Co., Ltd.) in the Comparative Example 1 to obtain a comparative particulate water-absorbing agent (COMP-2).

Comparative Example 3

To 100 parts by weight of the water-absorbing resin particles (A1) obtained in the Production Example 1, a surface crosslinking agent solution including 0.025 parts by weight of ethylene glycol diglycidyl ether, 0.3 parts by weight of ethylene carbonate, 0.5 parts by weight of propylene glycol, and 2.0 parts by weight of deionized water was mixed. The above mixture was heated at 200° C. for 40 minutes to obtain surface crosslinked water-absorbing resin particles (A5). To 100 parts by weight of the surface crosslinked water-absorbing resin particles (A5), one part by weight of 1% by weight of aqueous DTPA solution was added while being stirred, and was mixed therewith for one minute. Subsequently, the resulting mixture was left in a hot air dryer at 60° C. for 30 minutes, and then was made to pass through a wire mesh having an opening of 850 μm. A mixed solution of 3.3 parts by weight of colloidal silica (manufactured by AZ Electronic Materials Co., Klebsol 30B12) and 1.0 part by weight of propylene glycol was added uniformly thereto and mixed while being stirred. The resulting mixture was left in a hot air dryer at 60° C. for 60 minutes, and then was made to pass through a wire mesh having an opening of 850 μm to obtain a comparative particulate water-absorbing agent (COMP-3).

Comparative Examples 4 to 6

The same reaction and operation as the Comparative Example 1 except that 0.3 parts by weight of the hydrotalcite was changed to 0.3 parts by weight of the following water-insoluble inorganic fine particles in the Comparative Example 1 to obtain comparative particulate water-absorbing agents (COMP-4) to (COMP-6).

Changed to 0.3 parts by weight of zinc oxide (manufactured by ALDRICH, Co.) (Comparative Example 4)

Changed to 0.3 parts by weight of tricalcium phosphate (manufactured by Wako Pure Chemical Industries, Ltd.) (Comparative Example 5)

Changed to 0.3 parts by weight of aluminum hydroxide (manufactured by Nippon Light Metal Company, Ltd., particle diameter: 1.6 μm) (Comparative Example 6)

(Comparative Example 7) Reworking of Patent Literature (U.S. Pat. No. 6,071,976)

A water-absorbing agent was produced in conformity with the Example 17 of Patent Literature 17, which does not include the (d) step for mixing water-insoluble inorganic fine particles according to the present invention.

That is, according to the description in Patent Literature 17, into 5500 parts by weight of 33% by weight of aqueous sodium acrylate solution (rate of neutralization: mol %), 2.9 parts by weight of polyethylene glycol diacrylate (n=8) as an internal crosslinking agent was dissolved to obtain a reaction liquid. Polymerization was performed at 30° C. to 80° C. 60 minutes after the initiation of the polymerization, a hydrogel-forming polymer was taken out. The resulting hydrogel-forming polymer was spread on a wire mesh having an opening of 300 μm, and was dried with hot air at 150° C. for 90 minutes. Subsequently, the dried product was crushed using a roll granulator type crusher. By further classifying the resulting particles with a wire mesh having an opening of 850 μm and a wire mesh of 150 μm, water-absorbing resin particles (D1) as a fraction which had passed through the wire mesh of 850 μm but had not passed through the wire mesh of 150 μm and water-absorbing resin fine particles (D2) as a fraction which had passed through the wire mesh of 150 μm were obtained. CRC, moisture content, particle size distribution, and D50 of the resulting water-absorbing resin particles (D1) and water-absorbing resin fine particles (D2) are indicated in Table 1.

Subsequently, according to the description in Patent Literature 17, the water-absorbing resin fine particles (D2) were put into a continuous extrusion type mixer at a rate of 2 kg/minute, and 163 parts by weight of ion-exchanged water having 0.1 parts by weight of glycerin dissolved therein was put from a liquid supply port having a diameter of 5 mm and provided in the continuous extrusion type mixer per 100 parts by weight of the water-absorbing resin fine particles (D2). The water-absorbing resin fine particles (D2) and ion-exchanged water containing glycerin were thereby mixed continuously. As a result, uniform particulate hydrogel-forming granules were discharged continuously from a discharge port. The resulting particulate hydrogel-forming granules were aggregates of individual particles, and most of the granules were uniform hydrogel-forming granules each having a particle diameter of about 1 mm to 5 mm.

Subsequently, the hydrogel-forming granules were spread on a wire mesh having an opening of 300 μm so as to have a thickness of about 5 cm, and were dried with a hot air circulation type dryer at 160° C.

Subsequently, the dried granules were crushed using a roll granulator type crusher. Thereafter, by classifying the resulting granules with a wire mesh having an opening of 850 μm, water-absorbing resin granules (D3) were obtained. CRC, moisture content, particle size distribution, and D50 of the resulting water-absorbing resin granules (D3) are indicated in Table 1.

Further, to 100 parts by weight of the water-absorbing resin granules (D3), a surface crosslinking agent including 0.05 parts by weight of ethylene glycol diglycidyl ether, 0.75 parts by weight of glycerin, 3 parts by weight of water, 0.75 parts by weight of isopropyl alcohol, and 0.5 parts by weight of lactic acid was mixed. The resulting mixture was heated at 200° C. for 40 minutes to obtain a comparative particulate water-absorbing agent (COMP-7).

Comparative Example 8

To 100 parts by weight of the comparative particulate water-absorbing agent (COMP-7) obtained in the Comparative Example 7, an additive solution including 0.01 parts by weight of sorbitan monolaurate and 0.09 parts by weight of methanol was mixed. The resulting mixture was heated at 80° C. for 40 minutes to obtain a comparative particulate water-absorbing agent (COMP-8).

Comparative Example 9

To 100 parts by weight of the comparative particulate water-absorbing agent (COMP-7) obtained in the Comparative Example 7, an additive solution including 0.1 parts by weight of sorbitan monolaurate and 0.4 parts by weight of methanol was mixed. The resulting mixture was heated at 80° C. for 40 minutes to obtain a comparative particulate water-absorbing agent (COMP-9).

(Comparative Example 10) Comparative Water-Absorbing Agent by Production Method not Using Water-Insoluble Inorganic Particles To the surface crosslinked water-absorbing resin particles (B5) obtained in the Example 7, one part by weight of 1% by weight of aqueous DTPA solution was added while being stirred, and was mixed therewith for one minute. Subsequently, the resulting mixture was left in a hot air dryer at 60° C. for 30 minutes, and then was made to pass through a wire mesh having an opening of 850 μm to obtain water-absorbing resin particles (B6).

To 100 parts by weight of the water-absorbing resin particles (B6), a mixed liquid containing 0.80 parts by weight of 27% by weight of aqueous aluminum sulfate solution (8% by weight in terms of aluminum oxide), 0.134 parts by weight of 60% by weight of aqueous sodium lactate solution, and 0.016 parts by weight of propylene glycol was added. After the addition, the resulting mixture was dried under a condition of no wind at 60° C. for one hour. Subsequently, the resulting particles were made to pass through a JIS standard sieve having an opening of 850 μm to obtain a comparative particulate water-absorbing agent (COMP-10).

(Comparative Example 11) Reworking of Patent Literature 52

A water-absorbing agent was produced in conformity with the Example 5 of Patent Literature 52 (WO 2013/002387 A) not including the (a2) step for obtaining aqueous sodium acrylate solution having bubbles dispersed therein in advance before polymerization according to the present invention. In the meantime, in this example, the resulting hydrogel includes cells due to the boiling during polymerization, but the amount thereof (the number of cells) is small. Further, this example does not include the (a1) granulation step for obtaining granules by granulating a water-absorbing resin according to the present invention.

That is, according to the description in Patent Literature 52, an aqueous monomer solution (2) containing 193.3 parts by weight of acrylic acid, 64.4 parts by weight of 48% by weight of aqueous sodium hydroxide solution, 0.88 parts by weight of polyethylene glycol diacrylate (average n number: 9), 52 parts by weight of 0.1% by weight of aqueous pentasodium ethylenediamine tetra (methylene phosphonate) solution, 134 parts by weight of deionized water, and 700 ppm of p-methoxyphenol (relative to acrylic acid) was prepared.

Subsequently, the aqueous monomer solution (2) the temperature of which had been adjusted to 40° C. was supplied continuously using a metering pump, and then 97.1 parts by weight of 48% by weight of aqueous sodium hydroxide solution was further subjected to line mixing continuously. In the meantime, at this time, the liquid temperature of the aqueous monomer solution (2) rose to 85° C. due to neutralization heat.

Further, 8.05 parts by weight of 4% by weight of aqueous sodium persulfate solution was further subjected to line mixing continuously, and then was supplied continuously to a continuous polymerization machine having a planar polymerization belt with a weir at each end so as to have a thickness of about 7.5 mm. Thereafter, polymerization (polymerization time: three minutes) was performed continuously to obtain a belt-like hydrogel-forming crosslinked polymer (3). The hydrogel-forming crosslinked polymer (3) included cells due to the boiling during polymerization. The hydrogel-forming crosslinked polymer (3) was continuously cut at regular intervals such that the cut length was about 200 mm in a width direction relative to the traveling direction of the polymerization belt.

According to the description in Patent Literature 52, the fragmented hydrogel-forming crosslinked polymer (4) was scattered on a through-flow belt within one minute after the termination of gel-crushing (at this time, the temperature of the fragmented hydrogel-forming crosslinked polymer (4) was 80° C.), and was dried at 185° C. for 30 minutes to obtain 246 parts by weight of a dried product (5). The moving speed of the through-flow belt was 1 [m/min], and the average speed of hot air was 1.0 [m/s] in a direction perpendicular to the moving direction of the through-flow belt.

Subsequently, the total amount of the dried product (5) at about 60° C. obtained in the drying step was continuously supplied to a three-stage roll mill and was crushed (crushing step). Thereafter, by further classifying the crushed particle with JIS standard sieves having an opening of 710 μm and 175 μm to obtain irregularly-crushed shaped water-absorbing resin particles (V). For the water-absorbing resin particles (V), the weight average particle diameter (D50) was 350 μm, the logarithmic standard deviation (σζ) in particle size distribution was 0.33, CRC was 42.1 [g/g], water soluble component (Ext specified by ERT470.2-02) was 14.1% by weight, and the ratio of 150 μm passing particles (ratio of particles passing through a sieve having an opening of 150 μm) was 0.6% by weight.

Subsequently, to 100 parts by weight of the water-absorbing resin particles (V), a (covalently bonded) surface crosslinking agent solution containing 0.3 parts by weight of 1,4-butane diol, 0.6 parts by weight of propylene glycol, and 3.0 parts by weight of deionized water was mixed uniformly, and the resulting mixture was heated at 208° C. for about 40 minutes. Thereafter, the particles were broken (sizing step) until the particles passed through a JIS standard sieve having an opening of 710 μm to obtain water-absorbing resin particles (VI) having an internal cell rate of 2.40%.

Further, by further mixing 0.5 parts by weight of water-insoluble inorganic fine particles (Aerosil 200, manufactured by NIPPON AEROSIL Co., Ltd.) to 100 parts by weight of the water-absorbing resin particles (VI) by dry stirring, a comparative particulate water-absorbing agent (COMP-11) was obtained.

TABLE 1

|  | CRC g/g | moisture content wt % | 850 μm or more % | particle size distribution 500 μm or more and less than 850 μm % | 300 μm or more and less than 500 μm % | 150 μm or more and less than 300 μm % | less than 150 μm % | D50 μm | sz |
|---|---|---|---|---|---|---|---|---|---|
| water-absorbing resin particles (A1) | 45.0 | 3.5 | 0.0 | 11.9 | 55.5 | 30.7 | 1.9 | 346 | 0.344 |
| water-absorbing resin fine particles (A2) | 43.4 | 4.2 | 0.0 | 0.0 | 0.0 | 11.9 | 88.1 | 106 | 0.41 |
| water-absorbing resin granules (A3) | 43.5 | 3.8 | 0.0 | 9.8 | 58.2 | 30.0 | 2.0 | 344 | 0.329 |
| water-absorbing resin particles (B1) | 45.2 | 4.7 | 0.0 | 10.9 | 56.1 | 30.2 | 2.8 | 343 | 0.352 |
| water-absorbing resin fine particles (B2) | 43.0 | 4.9 | 0.0 | 0.0 | 0.0 | 11.7 | 88.3 | 102 | 0.408 |
| water-absorbing resin granules (B3) | 42.9 | 4.9 | 0.0 | 10.2 | 57.1 | 30.3 | 2.4 | 343 | 0.34 |
| water-absorbing resin particles (C1) | 52.9 | 4.8 | 0.0 | 14.2 | 54.9 | 29.5 | 1.4 | 353 | 0.346 |
| water-absorbing resin fine particles (C2) | 51.7 | 5.1 | 0.0 | 0.0 | 0.0 | 12.5 | 87.5 | 104 | 0.423 |
| water-absorbing resin particles (D1) | 42.0 | 3.7 | 0.0 | 6.0 | 43.7 | 50.3 | 0.0 | 300 | 0.231 |
| water-absorbing resin fine particles (D2) | 42.0 | 4.2 | 0.0 | 0.0 | 0.0 | 0.0 | 100.0 | 100 | 0.381 |
| water-absorbing resin granules (D3) | 42.0 | 4.1 | 0.0 | 14.1 | 55.8 | 20.3 | 9.8 | 354 | 0.458 |

TABLE 2

|  |  | additive | addition amount wt % | CRC g/g | AAP g/g | Vortex sec. | surface tension mN/m | GCA g/g | blocking ratio after moisture absorption % |
|---|---|---|---|---|---|---|---|---|---|
| Example 1 | EX-1 | HT | 0.3 | 33.5 | 30.2 | 26 | 72 | 32.3 | 0 |
| Example 2 | EX-2 | Aerosil 200 | 0.3 | 33.8 | 25.7 | 24 | 72 | 28.3 | 18 |
| Example 3 | EX-3 | colloidal silica Klebsol 30B12 | 3.3 | 33.3 | 29.4 | 27 | 72 | 30.1 | 1 |
| Example 4 | EX-4 | zinc oxide | 0.3 | 33.6 | 30.2 | 29 | 72 | 33.2 | 1 |
| Example 5 | EX-5 | tricalcium phosphate | 0.3 | 33.4 | 30.1 | 29 | 72 | 32.3 | 3 |
| Example 6 | EX-6 | aluminum hydroxide | 0.3 | 33.9 | 30.5 | 29 | 72 | 32.8 | 8 |
| Example 7 | EX-7 | HT | 0.3 | 39.5 | 33.4 | 32 | 68 | 31.1 | 0 |
| Example 8 | EX-8 | HT | 0.3 | 36.0 | 31.0 | 30 | 70 | 31.5 | 0 |
| Example 9 | EX-9 | HT | 0.3 | 34.7 | 31.5 | 28 | 70 | 31.6 | 0 |
| Example 10 | EX-10 | HT | 0.3 | 35.5 | 31.0 | 29 | 68 | 31.2 | 0 |
| Example 11 | EX-11 | HT | 0.3 | 37.8 | 31.2 | 26 | 68 | 30.0 | 0 |
| Example 12 | EX-12 | HT | 0.3 | 41.1 | 27.9 | 24 | 68 | 30.7 | 0 |
| Comparative Example 1 | COMP-1 | HT | 0.3 | 34.0 | 31.3 | 50 | 72 | 25.7 | 0 |
| Comparative Example 2 | COMP-2 | Si | 0.3 | 33.5 | 29.0 | 45 | 71 | 25.2 | 0 |
| Comparative Example 3 | COMP-3 | colloidal silica Klebsol 30B12 | 3.3 | 34.0 | 30.5 | 44 | 72 | 26.6 | 0 |
| Comparative Example 4 | COMP-4 | zinc oxide | 0.3 | 34.0 | 32.0 | 47 | 72 | 27.7 | 4 |
| Comparative Example 5 | COMP-5 | tricalcium phosphate | 0.3 | 33.8 | 32.1 | 45 | 72 | 26.7 | 0 |

TABLE 2-continued

|  |  | additive | addition amount wt % | CRC g/g | AAP g/g | Vortex sec. | surface tension mN/m | GCA g/g | blocking ratio after moisture absorption % |
|---|---|---|---|---|---|---|---|---|---|
| Comparative Example 6 | COMP-6 | aluminum hydroxide | 0.3 | 34.0 | 31.8 | 48 | 72 | 27.6 | 1 |
| Comparative Example 7 | COMP-7 | — | — | 30.0 | 31.0 | 25 | 72 | 28.2 | 100 |
| Comparative Example 8 | COMP-8 | sorbitan monolaurate | 0.01 | 30.2 | 30.8 | 25 | 63 | 28.0 | 80 |
| Comparative Example 9 | COMP-9 | sorbitan monolaurate | 0.1 | 30.3 | 30.7 | 25 | 40 | 26.2 | 0 |
| Comparative Example 10 | COMP-10 | mixed liquid of aluminum sulfate | 0.95 | 39.1 | 32.5 | 33 | 68 | 30.2 | 85 |
| Comparative Example 11 | COMP-11 | Aerosil 200 | 0.5 | 32.3 | 27.8 | 33 | 72 | 27.6 | 0 |

TABLE 3

|  |  | particle size distribution | | | | | | |
|---|---|---|---|---|---|---|---|---|
|  |  | 850 μm or more % | 500 μm or more and less than 850 μm % | 300 μm or more and less than 500 μm % | 150 μm or more and less than 300 μm % | less than 150 μm % | D50 μm | sz |
| Example 1 | EX-1 | 0.0 | 10.9 | 56.8 | 29.3 | 3.1 | 345 | 0.352 |
| Example 2 | EX-2 | 0.0 | 11.1 | 55.8 | 30.1 | 3.0 | 343 | 0.356 |
| Example 3 | EX-3 | 0.0 | 10.8 | 57.1 | 29.6 | 2.5 | 345 | 0.344 |
| Example 4 | EX-4 | 0.0 | 11.3 | 56.9 | 29.1 | 2.7 | 346 | 0.349 |
| Example 5 | EX-5 | 0.0 | 11.2 | 56.4 | 29.6 | 2.8 | 345 | 0.352 |
| Example 6 | EX-6 | 0.0 | 10.5 | 57.1 | 30.1 | 2.3 | 344 | 0.340 |
| Example 7 | EX-7 | 0.0 | 10.9 | 55.5 | 30.9 | 2.7 | 342 | 0.353 |
| Example 8 | EX-8 | 0.0 | 11.5 | 57.1 | 28.4 | 3.0 | 347 | 0.353 |
| Example 9 | EX-9 | 0.0 | 10.8 | 58.1 | 27.9 | 3.2 | 347 | 0.350 |
| Example 10 | EX-10 | 0.0 | 11.1 | 55.8 | 30.2 | 2.9 | 343 | 0.355 |
| Example 11 | EX-11 | 0.0 | 11.5 | 57.0 | 29.4 | 2.0 | 347 | 0.341 |
| Example 12 | EX-12 | 0.0 | 13.2 | 55.8 | 29.1 | 2.0 | 351 | 0.348 |
| Comparative Example 1 | COMP-1 | 0.0 | 11.4 | 59.0 | 27.2 | 2.4 | 351 | 0.337 |
| Comparative Example 2 | COMP-2 | 0.0 | 11.6 | 58.8 | 26.9 | 2.7 | 351 | 0.342 |
| Comparative Example 3 | COMP-3 | 0.0 | 11.5 | 58.5 | 27.4 | 2.6 | 350 | 0.342 |
| Comparative Example 4 | COMP-4 | 0.0 | 10.9 | 58.9 | 27.1 | 3.1 | 340 | 0.345 |
| Comparative Example 5 | COMP-5 | 0.0 | 11.8 | 59.1 | 26.1 | 3.0 | 353 | 0.345 |
| Comparative Example 6 | COMP-6 | 0.0 | 11.7 | 58.7 | 26.7 | 2.9 | 352 | 0.346 |
| Comparative Example 7 | COMP-7 | 0.0 | 14.1 | 55.8 | 20.3 | 9.8 | 354 | 0.458 |
| Comparative Example 8 | COMP-8 | 0.0 | 14.0 | 56.9 | 19.3 | 9.8 | 356 | 0.453 |
| Comparative Example 9 | COMP-9 | 0.0 | 13.6 | 56.4 | 19.9 | 10.1 | 354 | 0.459 |
| Comparative Example 10 | COMP-10 | 0.0 | 11.5 | 56.4 | 30.1 | 2.0 | 346 | 0.341 |
| Comparative Example 11 | COMP-11 | 0.0 | 10.1 | 57.5 | 31.8 | 0.6 | 343 | 0.306 |

TABLE 4

|  |  | liquid absorption time | | | Re-wet amount | | |
|---|---|---|---|---|---|---|---|
|  |  | first time s | second time s | third time s | first time g/g | second time g/g | third time g/g |
| Example 1 | EX-1 | 134 | 144 | 161 | 1.1 | 10.6 | 15.6 |
| Example 2 | EX-2 | 136 | 143 | 155 | 1.2 | 11 | 17 |
| Example 3 | EX-3 | 133 | 146 | 165 | 0.9 | 11.1 | 16.8 |
| Example 4 | EX-4 | 136 | 147 | 164 | 1 | 11.5 | 16.4 |
| Example 5 | EX-5 | 133 | 148 | 163 | 1.1 | 11 | 16.2 |
| Example 6 | EX-6 | 136 | 151 | 166 | 0.9 | 10.9 | 16.5 |

TABLE 4-continued

| | | liquid absorption time | | | Re-wet amount | | |
|---|---|---|---|---|---|---|---|
| | | first time s | second time s | third time s | first time g/g | second time g/g | third time g/g |
| Example 7 | EX-7 | 112 | 133 | 155 | 0 | 8 | 15 |
| Example 8 | EX-8 | 123 | 139 | 158 | 0.8 | 10 | 15 |
| Example 9 | EX-9 | 123 | 137 | 160 | 0.6 | 9.2 | 15.3 |
| Example 10 | EX-10 | 120 | 140 | 162 | 0.7 | 9.6 | 15.2 |
| Example 11 | EX-11 | 116 | 136 | 150 | 0.8 | 9.1 | 16.2 |
| Example 12 | EX-12 | 122 | 143 | 157 | 1.1 | 9.9 | 16.6 |
| Comparative Example 1 | COMP-1 | 130 | 145 | 160 | 1 | 12 | 18.5 |
| Comparative Example 2 | COMP-2 | 131 | 141 | 156 | 1 | 13 | 20 |
| Comparative Example 3 | COMP-3 | 132 | 151 | 165 | 1.1 | 14 | 19 |
| Comparative Example 4 | COMP-4 | 135 | 147 | 155 | 0.9 | 13.4 | 19.2 |
| Comparative Example 5 | COMP-5 | 133 | 148 | 160 | 1.4 | 13.1 | 19.5 |
| Comparative Example 6 | COMP-6 | 133 | 144 | 158 | 1.4 | 13 | 18.8 |
| Comparative Example 7 | COMP-7 | 140 | 160 | 180 | 1 | 10 | 15 |
| Comparative Example 8 | COMP-8 | 138 | 165 | 188 | 1 | 12 | 18 |
| Comparative Example 9 | COMP-9 | 145 | 175 | 201 | 1 | 17 | 24 |
| Comparative Example 10 | COMP-10 | 120 | 145 | 160 | 1 | 10 | 17 |
| Comparative Example 11 | COMP-11 | 125 | 143 | 159 | 1 | 11 | 17.5 |

(Summary)

(Explanation on Tables 2 and 3)

Comparison between the Examples 1 to 6 and the Comparative Examples 1 to 6 indicates that the novel water-absorbing agent of the present invention can be obtained by the production method 1 of the present invention using a water-absorbing resin in the form of granules.

Comparison between the Examples 7 to 12 and the Comparative Examples 1 to 6 indicates that the novel water-absorbing agent of the present invention can be obtained by the production method 2 of the present invention using a water-absorbing resin in the form of a foamed polymer.

Comparison between the Example 7 and the Comparative Example 10 indicates that the novel water-absorbing agent of the present invention can be obtained by the production method of the present invention using water-insoluble inorganic fine particles.

The result of the Comparative Example 7 indicates that the granules of the water-absorbing resin described in Patent Literature 17, which does not use water-insoluble inorganic fine particles, have a poor blocking ratio after moisture absorption, that is 100% blocking, suggesting that the novel water-absorbing agent according to the present invention is not to be obtained by the method of granulating a water-absorbing resin as described in Patent Literature 17.

The results of the Comparative Examples 8 and 9 indicate that, even by additional using a surfactant as a blocking inhibitor in the granules of the water-absorbing resin described in Patent Literature 17, only GCA or the surface tension is lowered and the novel water-absorbing agent of the present invention cannot be obtained.

The result of the Comparative Example 11 indicates the following. That is, in the water-absorbing agent described in Patent Literature 52, the resulting hydrogel includes cells due to the boiling during polymerization, but the amount thereof (the number of cells) is small. Further, polymerization does not include the (a2) step for obtaining an aqueous sodium acrylate solution having bubbles dispersed therein in advance before polymerization, or a granulation step for obtaining granules by granulating a water-absorbing resin. Therefore, the novel water-absorbing agent of the present invention cannot be obtained.

(Explanation on Table 4)

Tables 2 and 3 indicate that the particle size distribution of the particulate water-absorbing agent in the Examples 1 to 12 is almost the same as that of the comparative particulate water-absorbing agent in the Comparative Examples 1 to 11. However, the evaluation results of the absorbent articles containing a water-absorbing agent in Table 4 indicate the following. That is, the second re-wet amount (Re-Wet) of the particulate water-absorbing agents in the Examples 1 to 12 according to the present invention was as small as 8 to 11.5 g and the third re-wet amount thereof was as small as 15 to 17 g. The re-wet amount was remarkably improved compared to the re-wet amount of the comparative particulate water-absorbing agents in the Comparative Examples 1 to 6, which are related art (13 to 14 g at the second time, 18.8 to 20 g at the third time).

In the meantime, the re-wet amount of the water-absorbing agent in Patent Literature 17 (Comparative Example 7) (10 g at the second time, 15 g at the third time) or the re-wet amount of the water-absorbing agent in Patent Literature 52 (Comparative Example 11) partially overlapped with the re-wet amount of the particulate water-absorbing agent according to the present invention. However, the water-absorbing agent in Patent Literature 17 (Comparative Example 7) had a poor blocking ratio after moisture absorption (that is, 100% blocking) (refer to Table 2), and thus poor handleability including mixing with a fiber during the production of an absorbent material. The third re-wet amount of the water-absorbing agent in Patent Literature 52 (Comparative Example 11) (17.5 g) was inferior to that of the water-absorbing agent of the present invention (15 to 17 g).

As described above and also from the Examples, it is found that the production method of the present invention provides a novel water-absorbing agent having better GCA and provides an excellent absorbent article having a smaller re-wet amount (Re-Wet).

(5) Comparison with Related Art

Patent Literatures 1 to 52 do not disclose gel capillary absorption (GCA), which is a novel parameter provided by the present application. The technique for imparting flowability after moisture absorption of a water-absorbing polymer described in Patent Literatures 47 to 52 does not disclose the production method of the present application. Further, the technique for improving the water absorbent speed due to granulation described in Patent Literatures 8 and 11 to 18 does not disclose the production method of the present application (for example, the above Comparative Example 7 showing the Example 17 in Patent Literature 17). Moreover, a technique for improving the water absorbent speed due to foaming described in Patent Literatures 21 to 46 does not disclose the production method of the present application.

The present application provides a novel water-absorbing agent specified by GCA, which is a novel parameter of the present application, and the like by an unconventional novel production method (production method 1 or production method 2). The novel water-absorbing agent specified by GCA and the like reduces the re-wet amount of an absorbent article during actual use.

INDUSTRIAL APPLICABILITY

Use of the particulate water-absorbing agent of the present invention makes it possible to easily produce a disposable diaper having a re-wet amount smaller than related art.

The present application is based on the Japanese patent application No. 2014-039599 filed on Feb. 28, 2014. The disclosed contents thereof are incorporated herein by reference as a whole.

The invention claimed is:

1. A particulate water-absorbing agent comprising a poly(meth)acrylic acid (salt)-based water-absorbing resin as a main component, wherein
the particulate water-absorbing agent has:
a weight average particle diameter (D50) of 300 to 500 μm,
a blocking ratio after moisture absorption when left for one hour at 25° C. and 90% relative humidity of 20% or less,
a surface tension of 60 mN/m or more, and
a gel capillary absorption (GCA) of 28.0 g/g or more.

2. The particulate water-absorbing agent according to claim 1, wherein the particulate water-absorbing aunt is surface crosslinked.

3. The particulate water-absorbing agent according to claim 1, wherein the particulate water-absorbing agent has a fluid retention capacity without pressure (CRC) of 28 g/g or more.

4. The particulate water-absorbing agent according to claim 1, wherein the particulate water-absorbing agent has a fluid retention capacity under pressure (AAP) of 25 g/g or more.

5. The particulate water-absorbing agent according to claim 1, wherein the particulate water-absorbing agent has a water absorption time by Vortex method of 40 seconds or less.

6. The particulate water-absorbing agent according to claim 1, wherein the particulate water-absorbing agent has a surface tension of 65 mN/m or more.

7. The particulate water-absorbing agent according to claim 1, wherein the particulate water-absorbing agent has a gel capillary absorption (GCA) of 30.0 g/g or more.

8. The particulate water-absorbing agent according to claim 1, comprising water-insoluble inorganic fine particles.

9. The particulate water-absorbing agent according to claim 8, wherein the water-insoluble inorganic fine particles content is from 0.01 to 1.0% V by weight per 100% by weight of the poly(meth)acrylic acid (salt)-based water-absorbing resin (solid content).

10. The particulate water-absorbing agent according to claim 8, wherein the volume average particle diameter of the water-insoluble inorganic fine particles is from 0.01 to 3 μm.

11. The particulate water-absorbing agent according to claim 1, comprising a chelating agent.

12. The particulate water-absorbing agent according to claim 11, wherein the chelating agent content is from 0.001 to 1 part by weight per 100 parts by weight of the poly(meth)acrylic acid (salt)-based water-absorbing resin (solid content).

13. The particulate water-absorbing agent according to claim 11, wherein the chelating agent is a compound selected from the group consisting of an organic phosphorus chelating agent and an amino carboxylic acid chelating agent.

14. The particulate water-absorbing agent according to claim 1, wherein the shape of the water-absorbing agent is an irregularly-crushed shape or granules thereof.

15. An absorbent article formed by including the particulate water-absorbing agent according to claim 1 and a hydrophilic fiber.

* * * * *